United States Patent
Ichiyanagi et al.

(10) Patent No.: US 11,384,381 B2
(45) Date of Patent: *Jul. 12, 2022

(54) REACTION ACCELERATING AGENT

(71) Applicant: Kikkoman Corporation, Noda (JP)

(72) Inventors: Atsushi Ichiyanagi, Chiba (JP);
Kazuhiko Shimoji, Chiba (JP)

(73) Assignee: Kikkoman Corporation, Chiba (JP)

( * ) Notice: Subject to any disclaimer, the term of this patent is extended or adjusted under 35 U.S.C. 154(b) by 306 days.

This patent is subject to a terminal disclaimer.

(21) Appl. No.: 16/317,216

(22) PCT Filed: Jul. 13, 2017

(86) PCT No.: PCT/JP2017/025622
§ 371 (c)(1),
(2) Date: Jan. 11, 2019

(87) PCT Pub. No.: WO2018/012607
PCT Pub. Date: Jan. 18, 2018

(65) Prior Publication Data
US 2019/0316174 A1    Oct. 17, 2019

(30) Foreign Application Priority Data

Jul. 13, 2016  (JP) .............. JP2016-138547

(51) Int. Cl.
*C12Q 1/26* (2006.01)
*C07C 245/10* (2006.01)
*C07D 231/46* (2006.01)

(52) U.S. Cl.
CPC .............. *C12Q 1/26* (2013.01); *C07C 245/10* (2013.01); *C07D 231/46* (2013.01)

(58) Field of Classification Search
None
See application file for complete search history.

(56) References Cited

U.S. PATENT DOCUMENTS

| | | | |
|---|---|---|---|
| 5,055,195 A | 10/1991 | Trasch et al. | |
| 5,370,990 A | 12/1994 | Staniford et al. | |
| 6,228,626 B1 | 5/2001 | Ichikawa et al. | |
| 7,070,948 B1 | 7/2006 | Sakaue et al. | |
| 2001/0046688 A1* | 11/2001 | Giri ..................... | C12Q 1/66 435/25 |
| 2003/0089472 A1* | 5/2003 | Cheng ................... | C12N 9/96 162/65 |
| 2005/0026265 A1 | 2/2005 | Furukawa et al. | |
| 2005/0037509 A1* | 2/2005 | Geisler ................. | G01N 21/82 436/164 |
| 2005/0287624 A1 | 12/2005 | Furukawa et al. | |
| 2007/0010000 A1 | 1/2007 | Sakaue et al. | |
| 2008/0113381 A1 | 5/2008 | Matsuoka et al. | |
| 2008/0233605 A1 | 9/2008 | Taniguchi et al. | |
| 2008/0295259 A1 | 12/2008 | Ueda et al. | |
| 2009/0239239 A1* | 9/2009 | Hirokawa ............ | C12N 9/0032 435/7.1 |
| 2010/0112622 A1 | 5/2010 | Yonehara et al. | |
| 2010/0178659 A1* | 7/2010 | Yonehara ............. | G01N 33/721 435/23 |
| 2015/0118700 A1 | 4/2015 | Ichiyanagi et al. | |
| 2016/0123999 A1 | 5/2016 | Ogawa et al. | |
| 2016/0138073 A1 | 5/2016 | Ogawa et al. | |
| 2016/0222432 A1* | 8/2016 | Lee ...................... | G01N 33/558 |
| 2016/0251695 A1 | 9/2016 | Masakari et al. | |

FOREIGN PATENT DOCUMENTS

| | | |
|---|---|---|
| JP | 60-036961 A | 2/1985 |
| JP | 05-033997 B2 | 5/1993 |
| JP | 06-169765 A | 6/1994 |
| JP | 07-503277 A | 4/1995 |
| JP | 11-127895 A | 5/1999 |
| JP | 2000-175685 A | 6/2000 |
| JP | 2001-095598 A | 4/2001 |
| JP | 2001-204495 A | 7/2001 |
| JP | 2005-168487 A | 6/2005 |
| JP | 2005-176828 A | 7/2005 |
| JP | 2007-014329 A | 1/2007 |
| JP | 2008-201968 A | 9/2008 |
| JP | 2011-229526 A | 11/2011 |
| WO | WO 93/15175 A1 | 8/1993 |
| WO | WO 97/13872 A1 | 4/1997 |
| WO | WO 03/023134 A1 | 3/2003 |
| WO | WO 2004/104203 A1 | 12/2004 |
| WO | WO 2005/049857 A1 | 6/2005 |
| WO | WO 2008/093722 A1 | 8/2008 |
| WO | WO 2008/108385 A1 | 9/2008 |
| WO | WO 2011/015325 A1 | 2/2011 |
| WO | WO 2013/162035 A1 | 10/2013 |
| WO | WO 2015/005257 A1 | 1/2015 |

(Continued)

OTHER PUBLICATIONS

Sunset Yellow dye downloaded from heeps://www.chemsrc.com/en/baike/583639.html on Feb. 3, 2021 (Year: 2010).*
Tartazine downloaded from https://www.chemspider.com/Chemical-Structure.10606981.html on Feb. 3, 2021 (Year: 2021).*
RN 915-67-3 printout downloaded from the Registry file from CAS Feb. 3, 2021 (Year: 2021).*
Zhao et al. Biocatal. Biotransformation (2014) 32(4): 214-221 (Year: 2014).*
RN 2243-76-7 printout downloaded from the Registry file from CAS Feb. 3, 2021 (Year: 2021).*
Diaz et al. J. Photochem. And Photobiol. (1998) 113: 27-33 (Year: 1998).*
Sanchez et al. (J. Photochem. And Photobiol. (1997) 105: 11-14 (Year: 1997).*

(Continued)

*Primary Examiner* — Susan M Hanley
(74) *Attorney, Agent, or Firm* — Foley & Lardner LLP

(57) ABSTRACT

Provided is a compound which accelerates the enzymatic reaction catalyzed by an oxidase. The present invention provides an oxidase reaction accelerating agent comprising a compound represented by formula (I) and a method using the same.

9 Claims, 1 Drawing Sheet
Specification includes a Sequence Listing.

(56) References Cited

FOREIGN PATENT DOCUMENTS

| WO | WO 2015/005258 A1 | 1/2015 | |
|---|---|---|---|
| WO | WO 2015/060429 A1 | 4/2015 | |
| WO | WO-2015050366 A1 * | 4/2015 | ........... G01N 33/558 |

OTHER PUBLICATIONS

International Search Report dated Aug. 29, 2017, in PCT/JP2017/025622.
Rubens A. Silva et al., "Enzymatic activity of cholesterol oxidase immobilized onto polymer nanoparticles mediated by Congo red," Colloids and Surfaces B: Biointerfaces, 2013, 110:347-355.

* cited by examiner

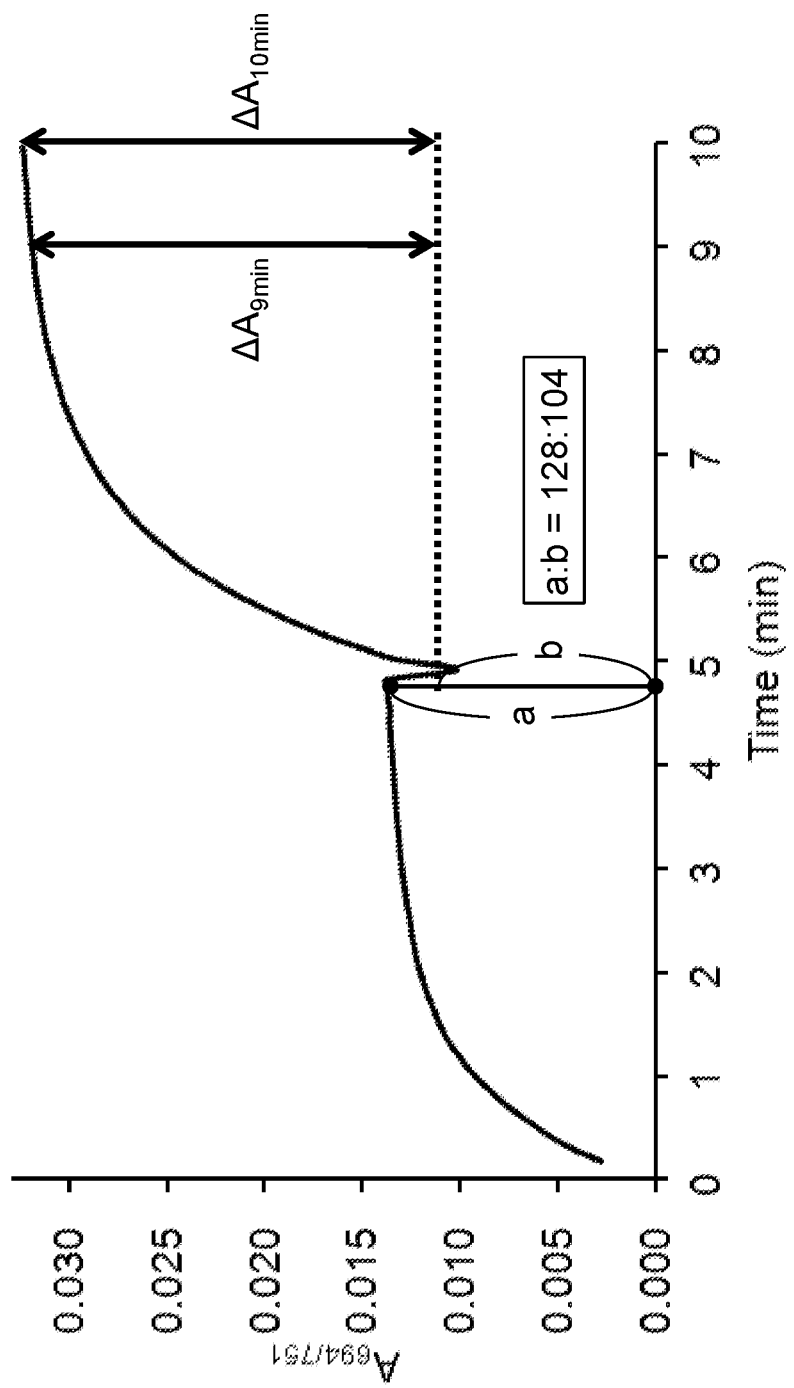

SEQUENCE LISTING

```
<160> NUMBER OF SEQ ID NOS: 8

<210> SEQ ID NO 1
<211> LENGTH: 434
<212> TYPE: PRT
<213> ORGANISM: Coniochaeta sp.

<400> SEQUENCE: 1

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
                20                  25                  30

Ala Pro Ala Asn Ile Thr Val Leu Asp Thr Phe Pro Ile Pro Ser Ala
            35                  40                  45

Gln Ser Ala Gly His Asp Leu Asn Lys Ile Met Gly Ile Asp His Arg
        50                  55                  60

Asn Lys Val Asn Leu Gln Met Ser Leu Glu Ala Arg Gln Met Trp Lys
65                  70                  75                  80

Glu Asp Glu Leu Phe Gln Pro Phe His Asn Thr Gly Arg Met Asp
                85                  90                  95

Cys Glu His Thr Pro Lys Gly Ile Glu Lys Leu Lys Lys Leu Tyr Gln
                100                 105                 110
```

```
Lys Leu His Asp Ala Gly Ala Gly Leu Glu Lys Thr His Ala Trp Leu
            115                 120                 125
Asp Asn Glu Asp Ala Ile Leu Ser Lys Met Pro Leu Leu Gln Arg Asp
        130                 135                 140
Gln Ile Gln Gly Trp Lys Ala Ile Trp Ser Gln Asp Gly Gly Trp Leu
145                 150                 155                 160
Ala Ala Ala Lys Ala Ile Asn Ala Ile Gly Gln Phe Leu Lys Glu Arg
                165                 170                 175
Gly Val Lys Phe Gly Phe Gly Ala Gly Ser Phe Lys Gln Pro Leu
            180                 185                 190
Phe Asp Asp Glu Gly Thr Thr Cys Ile Gly Val Glu Thr Ala Asp Gly
        195                 200                 205
Thr Lys Tyr Tyr Ala Asp Lys Val Leu Ala Ala Gly Ala Trp Ser
    210                 215                 220
Pro Thr Leu Val Asp Leu Glu Asp Gln Cys Cys Ser Lys Ala Trp Val
225                 230                 235                 240
Tyr Ala His Ile Gln Leu Thr Pro Glu Glu Ala Ala Lys Tyr Lys Gly
                245                 250                 255
Cys Pro Val Val Tyr His Gly Glu Phe Gly Phe Phe Glu Pro Asp
            260                 265                 270
Glu Phe Gly Val Ile Lys Val Cys Asp Glu Phe Pro Gly Phe Ser Arg
        275                 280                 285
Phe Lys Glu His Gln Pro Tyr Gly Ala Pro Ser Pro Lys Arg Ile Ser
    290                 295                 300
Val Pro Arg Ser His Ala Lys His Pro Thr Asp Thr Tyr Pro Asp Ala
305                 310                 315                 320
Ser Glu Val Ser Ile Lys Lys Ala Ile Ala Thr Phe Leu Pro Arg Phe
                325                 330                 335
Lys Asp Lys Pro Leu Phe Asn Arg Ala Leu Cys Trp Cys Thr Asp Thr
            340                 345                 350
Ala Asp Ser Thr Leu Leu Met Cys Glu His Pro Lys Trp Lys Asn Phe
        355                 360                 365
Ile Leu Ala Thr Gly Asp Ser Gly His Ser Phe Lys Ile Leu Pro Asn
    370                 375                 380
Val Gly Lys Tyr Val Val Glu Leu Ile Glu Gly Arg Leu Pro Glu Glu
385                 390                 395                 400
Met Ala Tyr Gln Trp Arg Trp Arg Pro Gly Asp Ala Leu Lys Ser
                405                 410                 415
Arg Arg Ala Ala Pro Pro Lys Asp Leu Ala Asp Met Pro Gly Trp Lys
            420                 425                 430
His Asp

<210> SEQ ID NO 2
<211> LENGTH: 1305
<212> TYPE: DNA
<213> ORGANISM: Coniochaeta sp.

<400> SEQUENCE: 2
atgacctcaa accgtgctga tacccgtgtt attgttgttg gtggtggtgg tacgattggc      60
tcctcgaccg ctctgcatct ggtgcgtagt ggctatgctc cggcgaacat taccgtcctg     120
gatacgtttc cgatcccgag cgcccagtct gcaggccatg atctgaataa aattatgggt     180
atcgaccacc gtaacaaagt taatctgcag atgagcctgg aagcgcgcca aatgtggaaa     240
gaagatgaac tgttccagcc gttttttccat aacaccggcc gtatggactg cgaacacacg     300
```

```
ccgaaaggta tcgaaaaact gaaaaaactg taccaaaaac tgcatgatgc cggcgcaggt    360
ctggaaaaaa cccacgcctg gctggataac gaagacgcaa ttctgagcaa aatgccgctg    420
ctgcagcgtg atcagattca aggttggaaa gccatctggt ctcaagacgg cggttggctg    480
gcagcagcaa aagctattaa tgcgatcggc cagtttctga agaacgcgg cgtgaaattc    540 ggttttggcg gtgcaggttc ttttaaacaa ccgctgttcg atgacgaagg caccacgtgt    600
atcggtgttg aaaccgctga tggcacgaaa tattacgcgg acaaagtggt tctggctgca    660
ggtgcatgga gtccgaccct ggtcgatctg aagaccagt gctgttccaa agcgtgggtg    720
tatgcgcata ttcaactgac gccgaagaa gccgcaaaat ataaaggctg cccggtcgtg    780
taccacggcg aatttggctt tttctttgaa ccggatgaat ttggcgtgat caaagtttgt    840
gacgaatttc cgggtttttc acgtttcaaa gaacatcagc cgtatggtgc gccgtcgccg    900
aaacgtatta gcgttccgcg ctctcatgcc aaacacccga ccgatacgta cccggacgca    960
agtgaagtct ccattaagaa agcgatcgcg acctttctgc gcgtttcaa agataaaccg   1020 ctgtttaatc gcgcactgtg ctggtgtacc gatacggccg acagcacact gctgatgtgc   1080
gaacatccga atggaaaaa ctttattctg gcgaccggcg attcaggtca ctcgttcaaa   1140
atcctgccga atgtgggcaa atatgttgtc gaactgattg aaggtcgcct gccggaagaa   1200
atggcttacc agtggcgttg gcgtccgggc ggtgatgccc tgaaaagtcg ccgtgctgct   1260
ccgccgaaag acctggctga tatgccgggc tggaaacatg actaa              1305
```

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
gtggtcgata cccataattt tattcagatc                                    30

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
tgggtatcga ccacggtaac aaagttaatc                                    30

<210> SEQ ID NO 5
<211> LENGTH: 434
<212> TYPE: PRT
<213> ORGANISM: Coniochaeta sp.

<400> SEQUENCE: 5

Met Thr Ser Asn Arg Ala Asp Thr Arg Val Ile Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Pro Ile Pro Ser Ala
        35                  40                  45

Gln Ser Ala Gly His Asp Leu Asn Lys Ile Met Gly Ile Asp His Gly
    50                  55                  60

```
Asn Lys Val Asn Leu Gln Met Ser Leu Glu Ala Arg Gln Met Trp Lys
 65                  70                  75                  80

Glu Asp Glu Leu Phe Gln Pro Phe Phe His Asn Thr Gly Arg Met Asp
                 85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Ala Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
            195                 200                 205

Thr Lys Tyr Tyr Ala Asp Lys Val Val Leu Ala Ala Gly Ala Trp Ser
210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Lys Tyr Lys Gly
                245                 250                 255

Cys Pro Val Val Tyr His Gly Glu Phe Gly Phe Phe Glu Pro Asp
            260                 265                 270

Glu Phe Gly Val Ile Lys Val Cys Asp Glu Phe Pro Gly Phe Ser Arg
            275                 280                 285

Phe Lys Glu His Gln Pro Tyr Gly Ala Pro Ser Pro Lys Arg Ile Ser
            290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Thr Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp

<210> SEQ ID NO 6
<211> LENGTH: 29
<212> TYPE: DNA
<213> ORGANISM: Artificial
<220> FEATURE:
<223> OTHER INFORMATION: primer
```

```
<400> SEQUENCE: 6 tttttttcagt ttttcgatac ctttcggcg                                    29

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
aaaaactgaa aaatattac caaaaactgc                                     30

<210> SEQ ID NO 8
<211> LENGTH: 434
<212> TYPE: PRT
<213> ORGANISM: Coniochaeta sp.

<400> SEQUENCE: 8
```

Met Thr Ser Asn Arg Ala Asp Thr Arg Val Ile Val Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Pro Ile Pro Ser Ala
        35                  40                  45

Gln Ser Ala Gly His Asp Leu Asn Lys Ile Met Gly Ile Asp His Gly
    50                  55                  60

Asn Lys Val Asn Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Tyr Tyr Gln
            100                 105                 110

Lys Leu His Asp Ala Gly Ala Gly Leu Glu Lys Thr His Ala Trp Leu
        115                 120                 125

Asp Asn Glu Asp Ala Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Lys Tyr Lys Gly
                245                 250                 255

Cys Pro Val Val Tyr His Gly Glu Phe Gly Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser

```
                290              295              300
Val Pro Arg Ser His Ala Lys His Pro Thr Asp Thr Tyr Pro Asp Ala
305             310              315              320

Ser Glu Val Ser Ile Lys Lys Ala Ile Ala Thr Phe Leu Pro Arg Phe
                325              330              335

Lys Asp Lys Pro Leu Phe Asn Arg Ala Leu Cys Trp Cys Thr Asp Thr
                340              345              350

Ala Asp Ser Thr Leu Leu Met Cys Glu His Pro Lys Trp Lys Asn Phe
                355              360              365

Ile Leu Ala Thr Gly Asp Ser Gly His Ser Phe Lys Ile Leu Pro Asn
        370              375              380

Val Gly Lys Tyr Val Val Glu Leu Ile Glu Gly Arg Leu Pro Glu Glu
385             390              395              400

Met Ala Tyr Gln Trp Arg Trp Arg Pro Gly Gly Asp Ala Leu Lys Ser
                405              410              415

Arg Arg Ala Ala Pro Pro Lys Asp Leu Ala Asp Met Pro Gly Trp Lys
            420              425              430

His Asp
```

REACTION ACCELERATING AGENT

CROSS-REFERENCE TO RELATED APPLICATIONS

This application is the U.S. National Stage of PCT/JP2017/025622, filed Jul. 13, 2017, which claims priority to JP 2016-138547, filed Jul. 13, 2016.

The instant application contains a Sequence Listing which has been submitted in ASCII format via EFS-WEB and is hereby incorporated by reference in its entirety. Said ASCII copy, created on Jan. 8, 2019, is named sequence.txt and is 14 KB.

TECHNICAL FIELD

The present invention relates to a reaction accelerating agent for an oxidase (examples thereof include, but are not limited to, a reaction accelerating agent for amadoriase, a reaction accelerating agent for sarcosine oxidase, and a reaction accelerating agent for cholesterol oxidase).

BACKGROUND ART

Oxidases are enzymes that catalyze oxidation reactions, and are applied to various fields. For example, in the clinical diagnostic field of diabetes mellitus, hemoglobin A1c (HbA1c) and glycated albumin (GA) have received attention as blood glucose control markers important for the diagnosis or symptom management of diabetes mellitus patients. Methods for rapidly and conveniently measuring HbA1c and GA include enzymatic methods using amadoriase, which is one type of oxidase.

The amadoriase catalyzes the reaction of oxidizing iminodiacetic acid or a derivative thereof (also referred to as an "amadori compound") in the presence of oxygen to produce glyoxylic acid or α-ketoaldehyde, an amino acid or a peptide and hydrogen peroxide. Examples of amadoriase include fructosyl amino acid oxidase, fructosyl peptide oxidase, and A1c oxidase (A1cOX) and the like.

As a method for measuring HbA1c using amadoriase, a method which involves degrading HbA1c with protease or the like, and quantifying a glycated substrate released from the β-chain amino terminus of HbA1c is known (e.g., Patent Literatures 1 to 11). Some amadoriases (A1cOXs) that act directly on HbA1c without the need of a protease are also known (Patent Literatures 12 and 13).

For the measurement of HbA1c, it is desirable to complete the reaction in a short time on the order of about 10 minutes. On the other hand, the types of A1cOXs known to date are limited and, therefore, in some cases it was necessary to incorporate the same in large amounts into the measurement reagent to complete the reaction in a short time on the order of about 10 minutes. However, enzymes are generally expensive and there is a need for decrease in the amount of A1cOX formulated into an HbA1c measurement reagent.

Patent Literature 14 describes a compound which shifts the detection wavelength of a phenothiazine derivative in a method for detection of a phenothiazine derivative dye in a reaction system by measuring the absorbance.

Sarcosine oxidase (EC 1.5.3.1) is an enzyme having catalytic ability of hydrolyzing sarcosine to produce glycine and formaldehyde. This enzyme can be used for the measurement of the amount of creatinine in human serum or urine and can be utilized as a diagnostic drug for various diseases including kidney disease. Sarcosine oxidases are known from the genus *Corynebacterium*, the genus *Bacillus*, the genus *Cylindrocarpon*, the genus *Pseudomonas*, the genus *Arthrobacter*, and the like. For modified sarcosine oxidases or various origins of sarcosine oxidase, see, for example, Patent Literatures 15 to 17.

Cholesterol oxidase (EC 1.1.3.6) is an oxidative enzyme that catalyzes the reaction between 33-hydroxysteroid and oxygen to produce the corresponding 3-oxosteroid and hydrogen peroxide. Cholesterol oxidase is subjected to research and development for the purpose of utilizing the same in the measurement of cholesterol concentrations in body fluids (Patent Literature 18), etc. Cholesterol oxidase is known to be produced by *Streptomyces, Brevibacterium, Rhodococcus, Pseudomonas, Burkholderia cepacia*, and the like. For cholesterol oxidase or various origins thereof, see, for example, Patent Literature 19.

As a method for measuring glycated albumin (GA) using amadoriase, for example, a method which involves degrading GA with protease or the like, and quantifying the released glycated substrate ε-fructosyl lysine (ε-FK) is known. See, for example, Patent Literature 20.

CITATION LIST

Patent Literature

Patent Literature 1: International Publication No. WO 2004/104203
Patent Literature 2: International Publication No. WO 2005/49857
Patent Literature 3: JP Patent Publication (Kokai) No. 2001-95598 A (2001)
Patent Literature 4: JP Patent Publication (Kokoku) No. 05-33997 B (1993)
Patent Literature 5: JP Patent Publication (Kokai) No. 11-127895 A (1999)
Patent Literature 6: International Publication No. WO 97/13872
Patent Literature 7: JP Patent Publication (Kokai) No. 2011-229526 A (2011)
Patent Literature 8: International Publication No. WO 2011/015325
Patent Literature 9: International Publication No. WO 2008/108385
Patent Literature 10: International Publication No. WO 2015/005258
Patent Literature 11: International Publication No. WO 2013/162035
Patent Literature 12: International Publication No. WO 2015/060429
Patent Literature 13: International Publication No. WO 2015/005257
Patent Literature 14: International Publication No. WO 2008/093722
Patent Literature 15: JP Patent Publication (Kokai) No. 2005-176828 A (2005)
Patent Literature 16: JP Patent Publication (Kokai) No. 2005-168487 A (2005)
Patent Literature 17: JP Patent Publication (Kokai) No. 2000-175685 A (2000)
Patent Literature 18: JP Patent Publication (Kokai) No. 6-169765 A (1994)
Patent Literature 19: JP Patent Publication (Kokai) No. 2007-014329 A (2007)
Patent Literature 20: JP Patent Publication (Kokai) No. 2001-204495 A (2001)

SUMMARY OF INVENTION

Technical Problem

In light of the problems as mentioned above, the present invention provides a compound accelerating (facilitating) enzymatic reaction catalyzed by an oxidase (examples thereof include, but are not limited to, amadoriase), i.e., an oxidase reaction accelerating agent (accelerant) (examples thereof include, but are not limited to, an amadoriase reaction accelerating agent). The present invention further provides a composition comprising the oxidase reaction accelerating agent (examples thereof include, but are not limited to, an amadoriase reaction accelerating agent). The present invention further provides a method using an oxidase and the oxidase reaction accelerating agent (examples thereof include, but are not limited to, a method for measuring HbA1c using amadoriase and an amadoriase reaction accelerating agent).

Solution to Problem

While there is scant information on compounds capable of accelerating the reaction of oxidases including amadoriases, the present inventors have conducted studies and, as a result, surprisingly found a compound capable of accelerating (enhancing) the reaction of an oxidase, thereby completing the present invention. That is, the present invention encompasses the following embodiments.

[1] A method using oxidase reaction, comprising the step of using an oxidase and an oxidase reaction accelerating agent represented by the following formula (I):

[Formula 1]

$$R^1\text{—}N\text{=}N\text{—}R^2 \quad (I)$$

wherein
$R^1$ and $R^2$ are each independently an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents, wherein said substituent(s) is selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, —CO—$NH_2$, —$R^3$, —NH—$R^4$, —NHCO—NH—$R^5$—N=N—$R^6$, —$SO_3X$, —COOX, Y, and Z;
X is selected from the group consisting of —H, —Na, —K, and —Li;
Y is selected from the group consisting of —H, —$SO_3X$, and —COOX;
Z is selected from the group consisting of —H, —$C_{1-6}$ alkyl, —O—$C_{1-6}$ alkyl, and —$SO_3X$;
each X, Y, and Z may be the same or different;
—$R^3$ is —H, or is an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, and —$SO_3X$;

—$R^4$ is an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, —$SO_3X$, —COOX, Y, and Z; and —$R^5$ and —$R^6$ are each independently an aromatic 5- or 6-membered monocyclic carbocyclic ring or heterocyclic ring containing at least one nitrogen atom, sulfur atom or oxygen atom, or a 9- or 10-membered fused ring containing the aromatic 5- to 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —O—$CH_3$, —$CONH_2$, —$NO_2$, —$NH_2$, —$SO_3X$, —COOX, Y, and Z, provided that when $R^1$ or $R^2$ is an aromatic 5-membered monocyclic carbocyclic ring or heterocyclic ring containing at least one nitrogen atom, sulfur atom or oxygen atom, the heterocyclic ring is not substituted with —COOX.

[2] The method according to 1, wherein regarding the reaction accelerating agent represented by formula (I), $R^1$ and $R^2$ are each independently an aromatic 6-membered monocyclic carbocyclic ring, or a 10-membered fused ring containing the aromatic 6-membered monocyclic carbocyclic ring, wherein the ring may optionally be substituted with one or more substituents.

[3] The method according to 1 or 2, wherein regarding the reaction accelerating agent represented by formula (I), $R^1$ and $R^2$ are each independently selected from the group consisting of

[Formula 2]

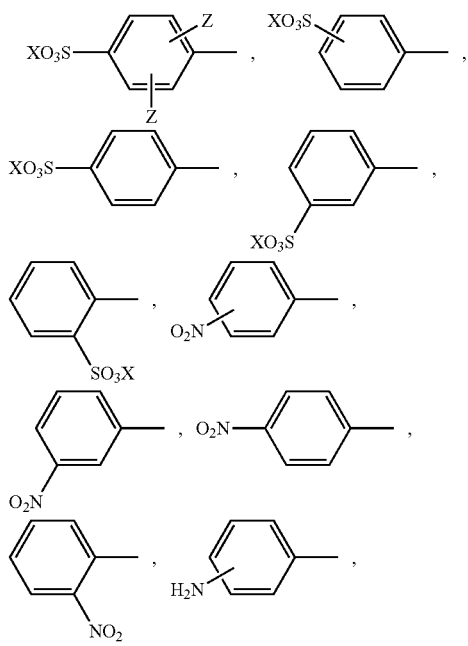

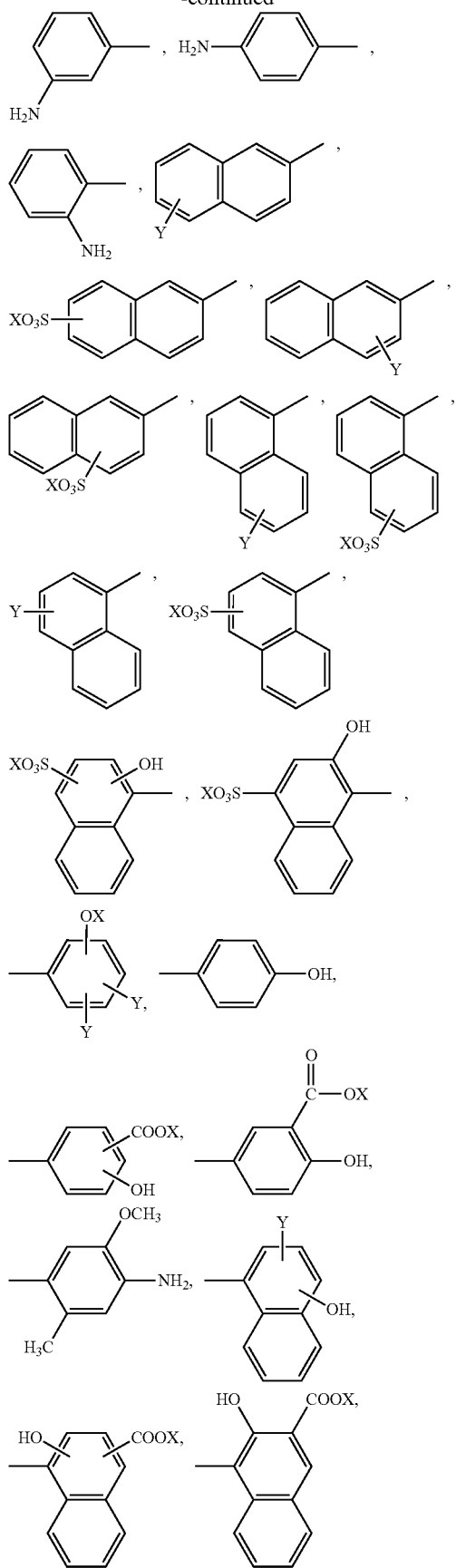
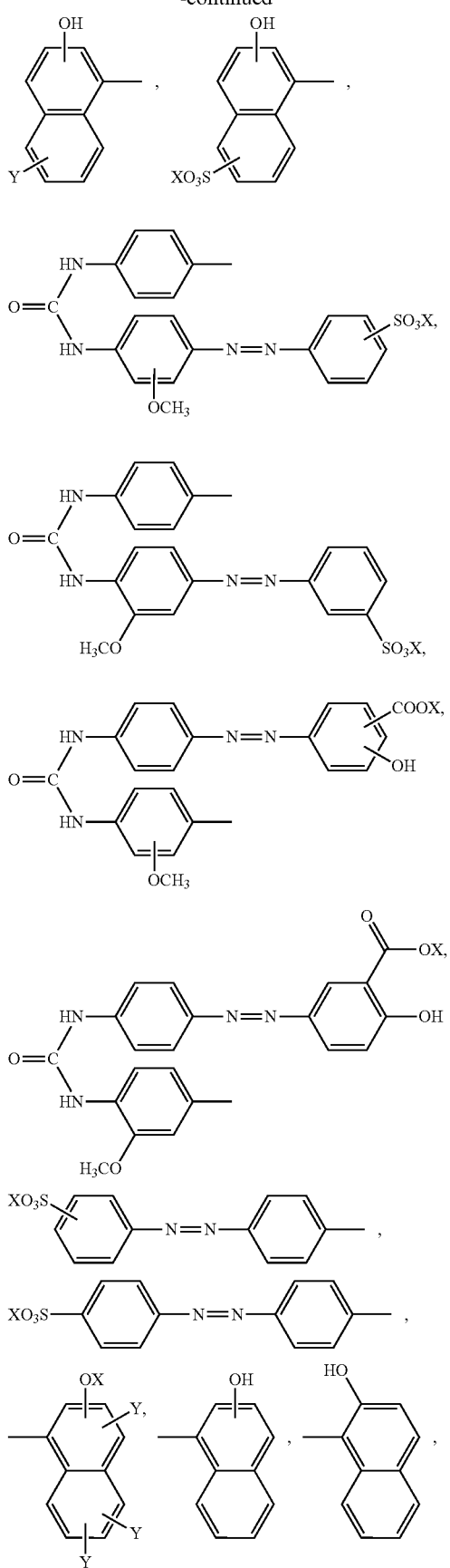

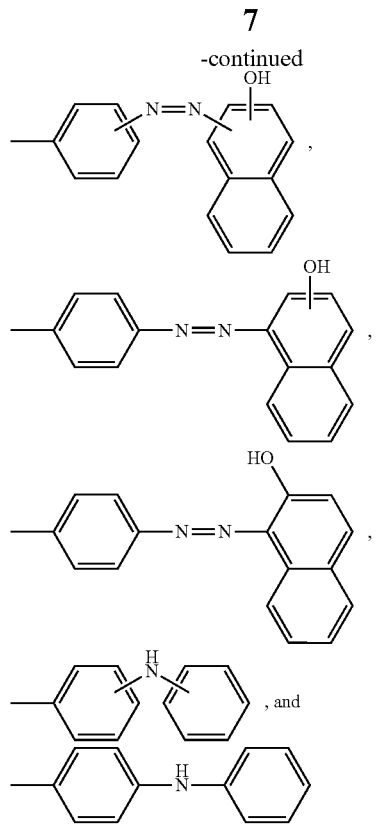
wherein X, Y, and Z are as defined in 1.
[4] The method according to 1, 2 or 3, wherein regarding the reaction accelerating agent represented by formula (I), $R^1$ is selected from the group consisting of
[Formula 3]
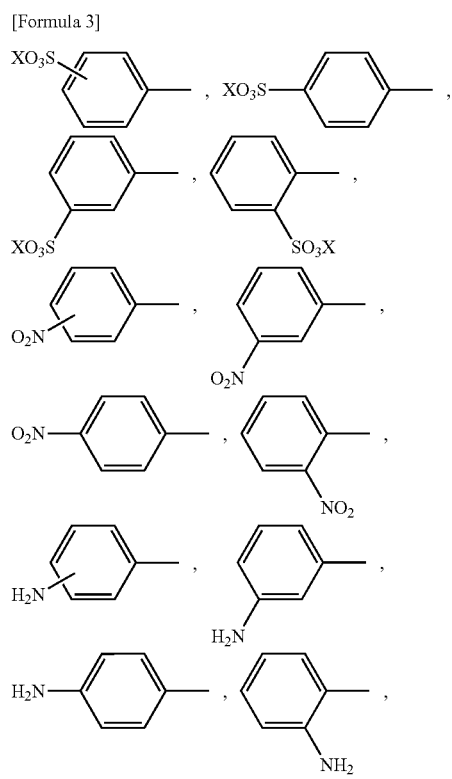
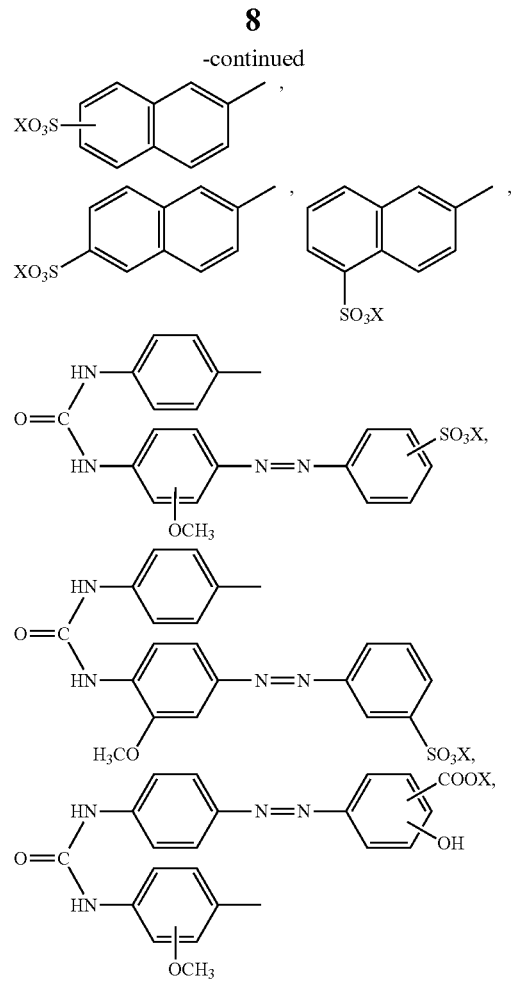
and $R^2$ is selected from the group consisting of
[Formula 4]

-continued

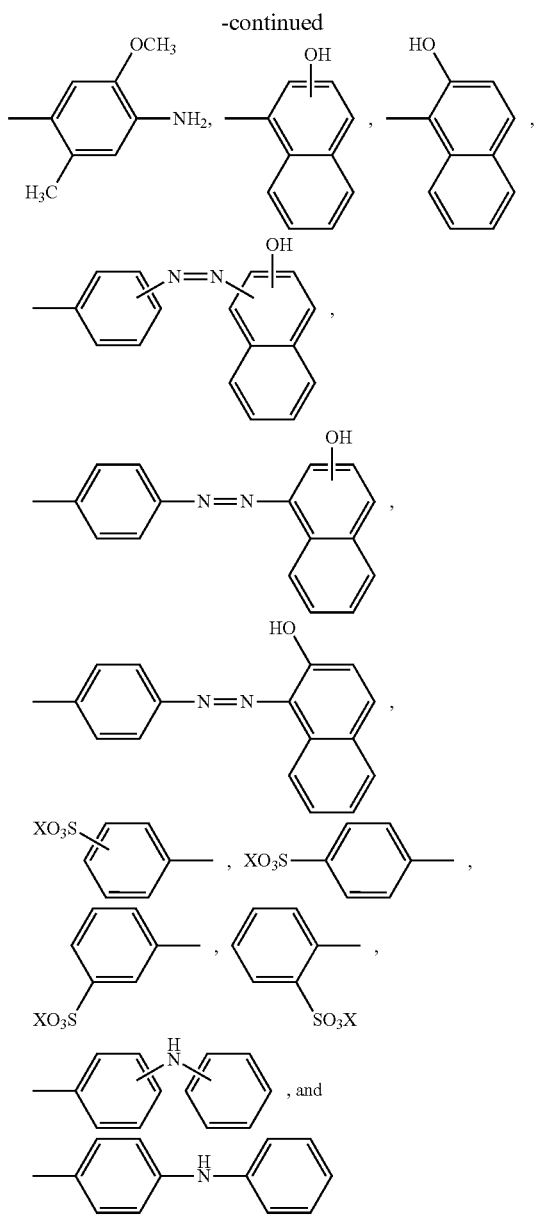

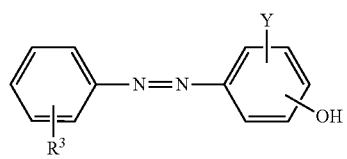

wherein X is as defined in 1.

[5] The method according to 1, wherein the reaction accelerating agent represented by formula (I) is a reaction accelerating agent represented by the following formula:

[Formula 5]

(II)

(structure with R³ and Y, OH)

wherein
X is selected from the group consisting of —H, —Na, —K, and —Li;
Y is selected from the group consisting of —H, —SO₃X, and —COOX;
each X and Y may be the same or different;
—R³ is —H or —NHCO—NH—R⁵—N=N—R⁶, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C$_{1-6}$ alkyl, —C$_{2-6}$ alkenyl, —C$_{2-6}$ alkynyl, =O, —OH, —O—C$_{1-6}$ alkyl, —CONH$_2$, —NO$_2$, —NH$_2$, and —SO$_3$X; and
—R⁵ and —R⁶ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C$_{1-6}$ alkyl, —C$_{2-6}$ alkenyl, —C$_{2-6}$ alkynyl, =O, —OH, —O—C$_{1-6}$ alkyl, —O—CH$_3$, —CONH$_2$, —NO$_2$, —NH$_2$, and —SO$_3$X.

[6] The method according to 1, wherein the reaction accelerating agent represented by formula (I) is a reaction accelerating agent represented by any of the following formulae:

[Formula 6]

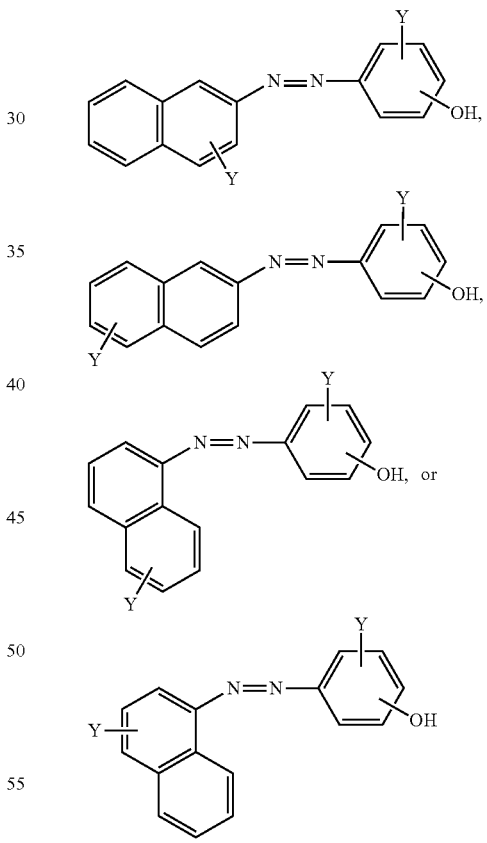

wherein
X is selected from the group consisting of —H, —Na, —K, and —Li;
Y is selected from the group consisting of —H, —SO₃X, and —COOX; and
each X and Y may be the same or different.

[7] The method according to 1, wherein the reaction accelerating agent represented by formula (I) is a reaction accelerating agent represented by the following formula:

[Formula 7]

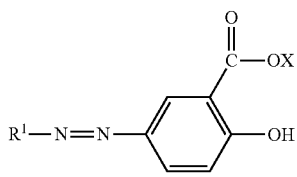

(III)

wherein
R¹ is a benzene ring or a naphthalene ring which may optionally be substituted with one or more substituents, wherein
said substituent(s) is selected from the group consisting of —NO₂, —SO₃X, and

[Formula 8]

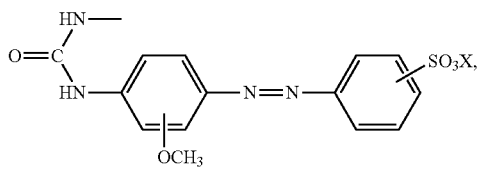

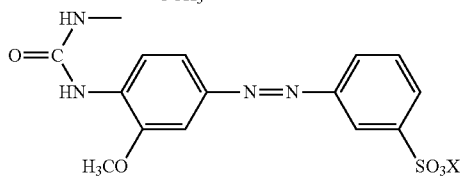

and
X is selected from the group consisting of —H, —Na, —K, and —Li.

[8] The method according to 1, wherein regarding the reaction accelerating agent represented by formula (I), R¹ is an aromatic 6-membered monocyclic carbocyclic ring which may optionally be substituted with one or more substituents, and R² is an aromatic 5-membered monocyclic heterocyclic ring containing at least one nitrogen atom, sulfur atom or oxygen atom optionally substituted with one or more substituents.

[9] The method according to 1 or 8, wherein R² is an aromatic 5-membered monocyclic heterocyclic ring containing two nitrogen atoms wherein said ring may optionally be substituted with one or more substituents, and the heterocyclic ring is substituted with

[Formula 9]

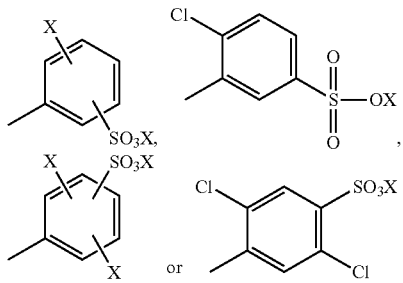

wherein X is as defined in 1, and each X may be the same or different.

[10] The method according to 1, 8 or 9, wherein R² is

[Formula 10]

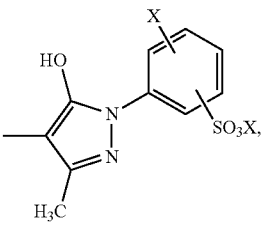

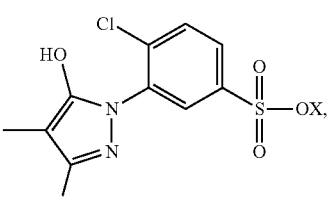

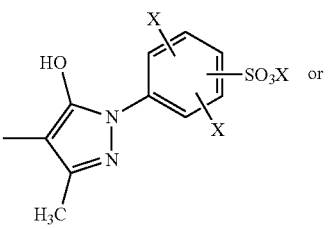

or

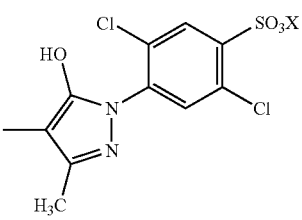

wherein X is as defined in 1, and each X may be the same or different.

[11] The method according to any of 1 to 10, wherein the compound represented by formula (I) is selected from the group consisting of a compound represented by the following formula:

[Formula 11]

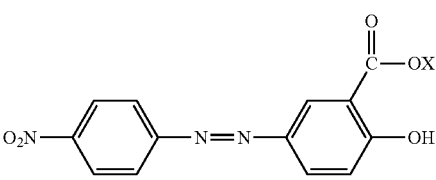

(IV)

wherein X is selected from the group consisting of —H, —Na, —K, and —Li, a compound represented by the following formula:

[Formula 12]

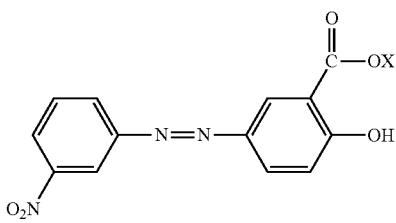
V wherein X is selected from the group consisting of —H, —Na, —K, and —Li, a compound represented by the following formula:

[Formula 13]

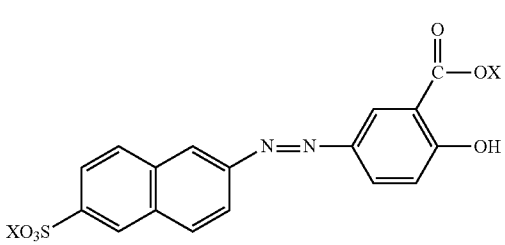
VI wherein X is selected from the group consisting of —H, —Na, —K, and —Li, and each X may be the same or different, a compound represented by the following formula:

[Formula 14]

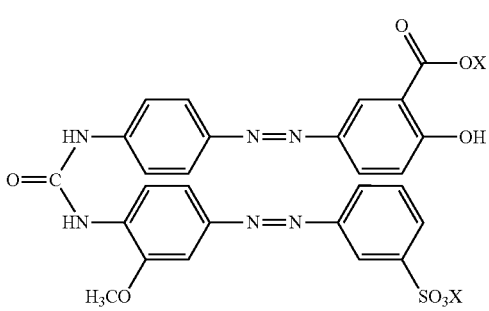
VII wherein X is selected from the group consisting of —H, —Na, —K, and —Li, and each X may be the same or different, a compound represented by the following formula:

[Formula 15]

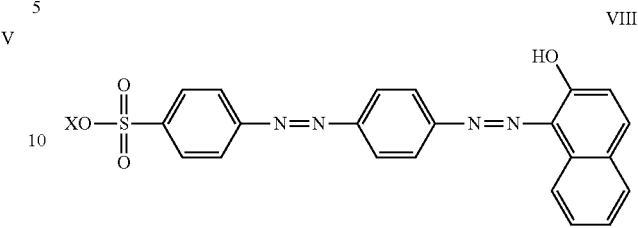
VIII wherein X is selected from the group consisting of —H, —Na, —K, and —Li, a compound represented by the following formula:

[Formula 16]

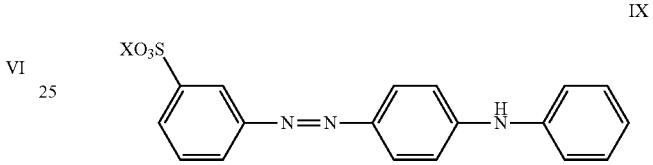
IX wherein X is selected from the group consisting of —H, —Na, —K, and —Li, a compound represented by the following formula:

[Formula 17]

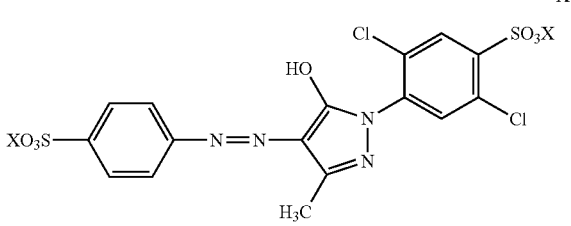
X wherein X is selected from the group consisting of —H, —Na, —K, and —Li, and each X may be the same or different, a compound represented by the following formula:

[Formula 18]

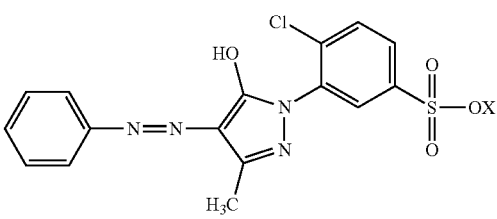
XI wherein X is selected from the group consisting of —H, —Na, —K, and —Li, and a compound represented by the following formula:

[Formula 19]

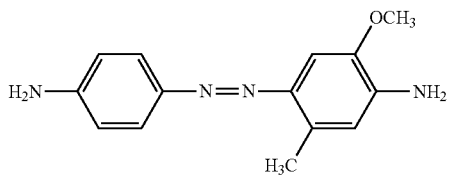

[12] The method according to any of 1 to 11, wherein the oxidase is an oxidase selected from the group consisting of amadoriase, sarcosine oxidase, and cholesterol oxidase.

[13] An oxidase reaction accelerating agent comprising a compound represented by formula (I):

[Formula 20]

wherein
$R^1$ and $R^2$ are each independently an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents, wherein
said substituent(s) is selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —CONH$_2$, —NO$_2$, —NH$_2$, —CO—NH$_2$, —$R^3$, —NH—$R^4$, —NHCO—NH—$R^5$—N=N—$R^6$, —SO$_3$X, —COOX, Y, and Z;
X is selected from the group consisting of —H, —Na, —K, and —Li;
Y is selected from the group consisting of —H, —SO$_3$X, and —COOX;
Z is selected from the group consisting of —H, —$C_{1-6}$ alkyl, —O—$C_{1-6}$ alkyl, and —SO$_3$X;
each X, Y, and Z may be the same or different;
—$R^3$ is —H, or is an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —CONH$_2$, —NO$_2$, —NH$_2$, and —SO$_3$X;
—$R^4$ is an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —CONH$_2$, —NO$_2$, —NH$_2$, —SO$_3$X, —COOX, Y, and Z; and
—$R^5$ and —$R^6$ are each independently an aromatic 5- or 6-membered monocyclic carbocyclic ring or heterocyclic ring containing at least one nitrogen atom, sulfur atom or oxygen atom, or a 9- or 10-membered fused ring containing the aromatic 5- to 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —O—CH$_3$, —CONH$_2$, —NO$_2$, —NH$_2$, —SO$_3$X, —COOX, Y, and Z,
provided that when $R^1$ or $R^2$ is an aromatic 5-membered monocyclic carbocyclic ring or heterocyclic ring containing at least one nitrogen atom, sulfur atom or oxygen atom, the heterocyclic ring is not substituted with —COOX.

[14] The reaction accelerating agent according to 13, wherein regarding the reaction accelerating agent represented by formula (I), $R^1$ and $R^2$ are each independently an aromatic 6-membered monocyclic carbocyclic ring, or a 10-membered fused ring containing the aromatic 6-membered monocyclic carbocyclic ring, wherein the ring may optionally be substituted with a substituent(s).

[15] The reaction accelerating agent according to 13 or 14, wherein regarding the compound represented by formula (I), $R^1$ and $R^2$ are each independently selected from the group consisting of

[Formula 21]

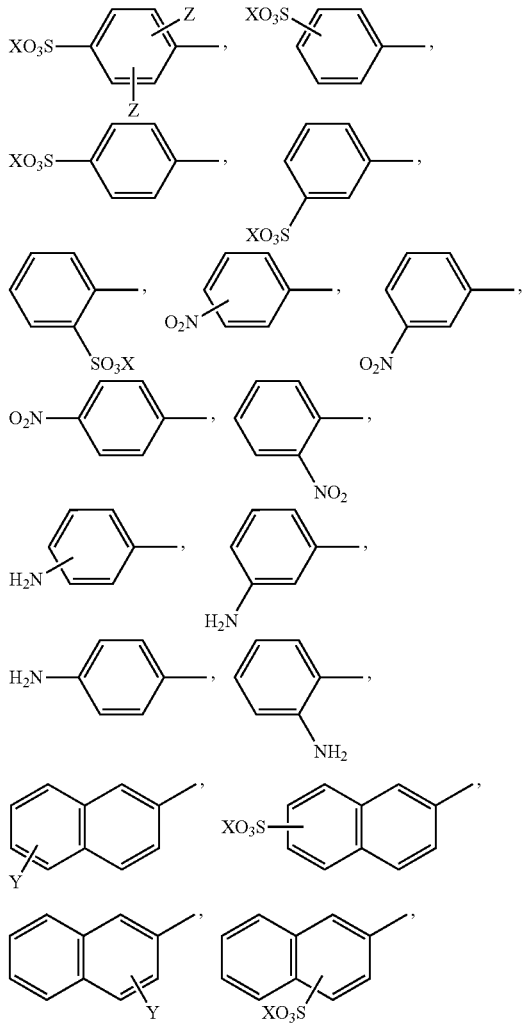

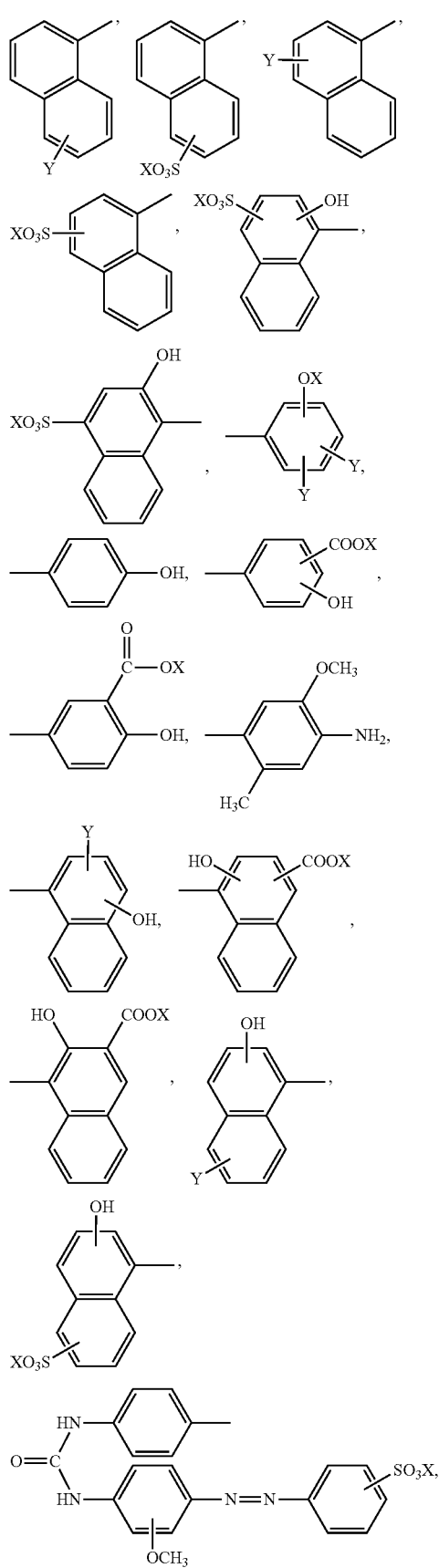
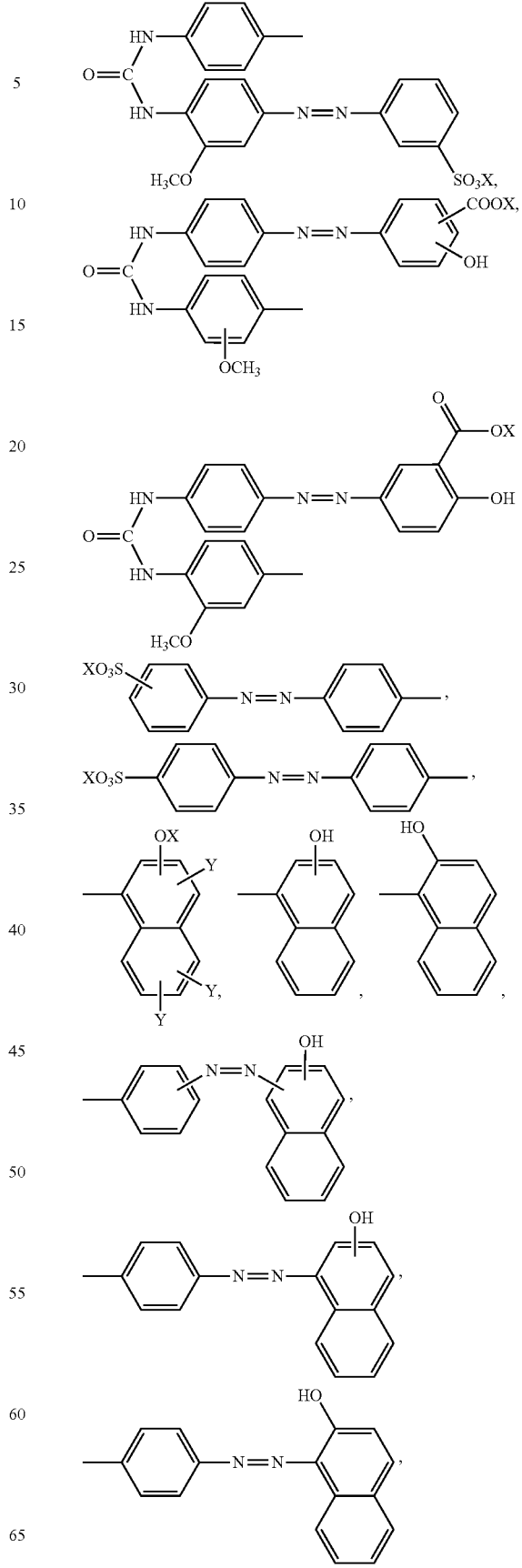

-continued
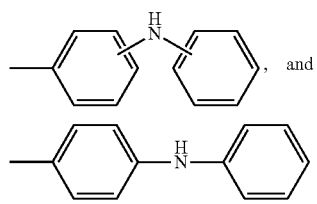, and
wherein X, Y, and Z are as defined in 13.
[16] The reaction accelerating agent according to any of 13 to 15, wherein regarding the reaction accelerating agent represented by formula (I), $R^1$ is selected from the group consisting of
[Formula 22]
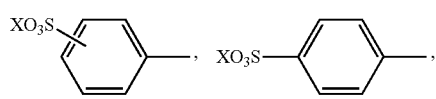
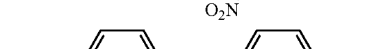
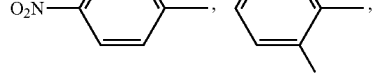
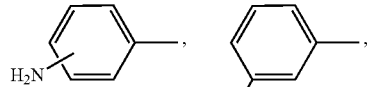
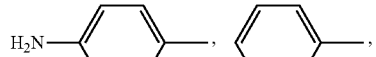
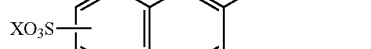
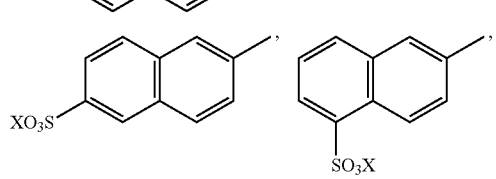
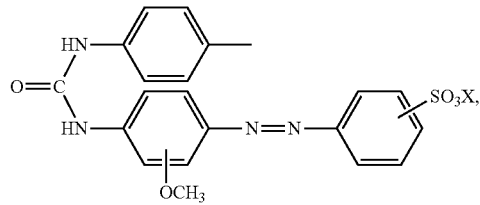
-continued
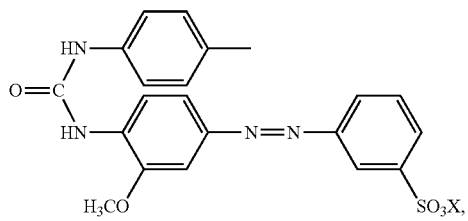
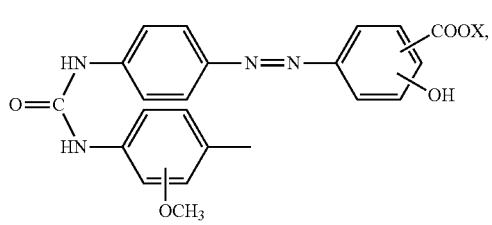
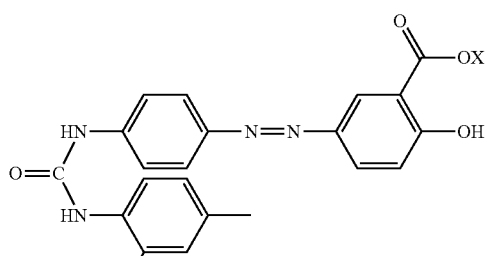
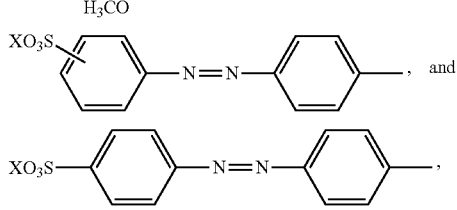
and $R^Z$ is selected from the group consisting of
[Formula 23]
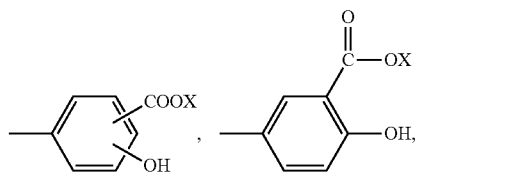
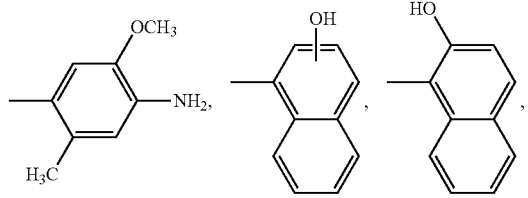
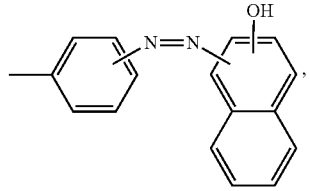

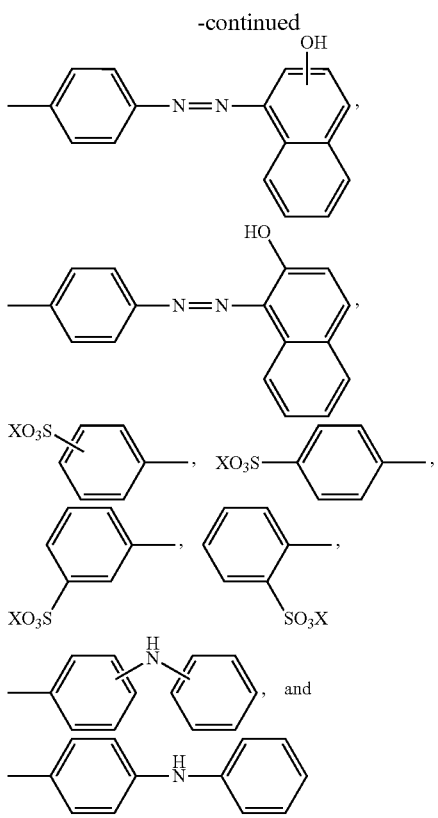

wherein X is as defined in 13.

[17] The reaction accelerating agent according to any of 13 to 16, wherein the reaction accelerating agent represented by formula (I) is a reaction accelerating agent represented by the following formula:

[Formula 24]

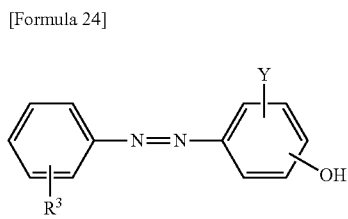

(II)

wherein
X is selected from the group consisting of —H, —Na, —K, and —Li;
Y is selected from the group consisting of —H, —$SO_3X$, and —COOX;
each X and Y may be the same or different;
—$R^3$ is —H or —NHCO—NH—$R^5$—N=N—$R^6$, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, and —$SO_3X$; and
—R and —$R^6$ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —O—$CH_3$, —$CONH_2$, —$NO_2$, —$NH_2$, and —$SO_3X$.

[18] The reaction accelerating agent according to any of 13 to 17, wherein the reaction accelerating agent represented by formula (I) is a reaction accelerating agent represented by any of the following formulae:

[Formula 25]

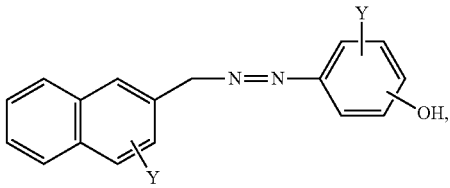

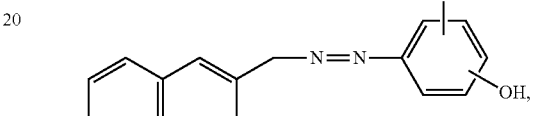

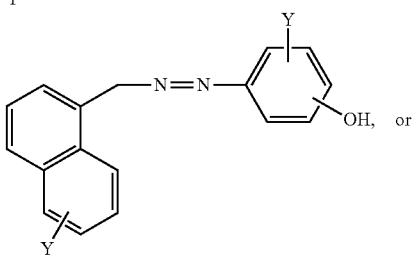

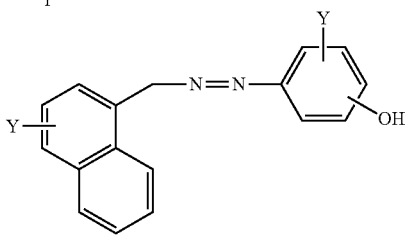

wherein
X is selected from the group consisting of —H, —Na, —K, and —Li;
Y is selected from the group consisting of —H, —$SO_3X$, and —COOX; and
each X, Y, and Z may be the same or different.

[19] The reaction accelerating agent according to any of 13 to 17, wherein the reaction accelerating agent represented by formula (I) is a reaction accelerating agent represented by the following formula:

[Formula 26]

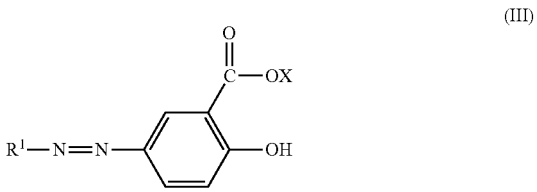

(III)

wherein
R[1] is a benzene ring or a naphthalene ring which may optionally be substituted with one or more substituents, wherein
said substituent(s) is selected from the group consisting of —NO$_2$, —SO$_3$X, and

[Formula 27]

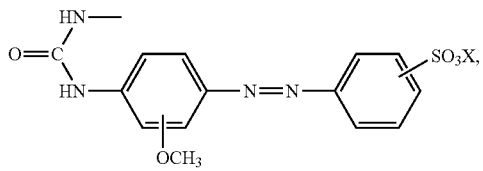

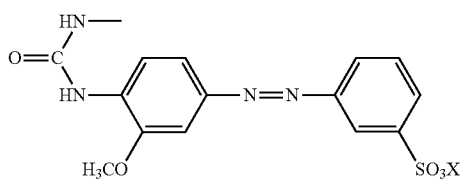

and

X is selected from the group consisting of —H, —Na, —K, and —Li.

[20] The reaction accelerating agent according to 13, wherein regarding the reaction accelerating agent represented by formula (I), R[1] is an aromatic 6-membered monocyclic carbocyclic ring which may optionally be substituted with one or more substituents, and R[2] is an aromatic 5-membered monocyclic heterocyclic ring containing at least one nitrogen atom, sulfur atom or oxygen atom optionally substituted with one or more substituents.

[21] The reaction accelerating agent according to 13 or 20, wherein R[2] is an aromatic 5-membered monocyclic heterocyclic ring containing two nitrogen atoms wherein said ring may optionally be substituted with one or more substituents, and the heterocyclic ring is substituted with

[Formula 28]

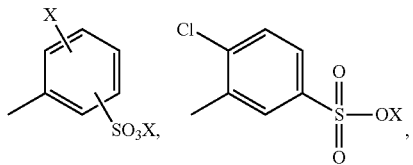

wherein X is as defined in 13, and each X may be the same or different.

[22] The reaction accelerating agent according to 13, 20 or 21, wherein R[2] is

[Formula 29]

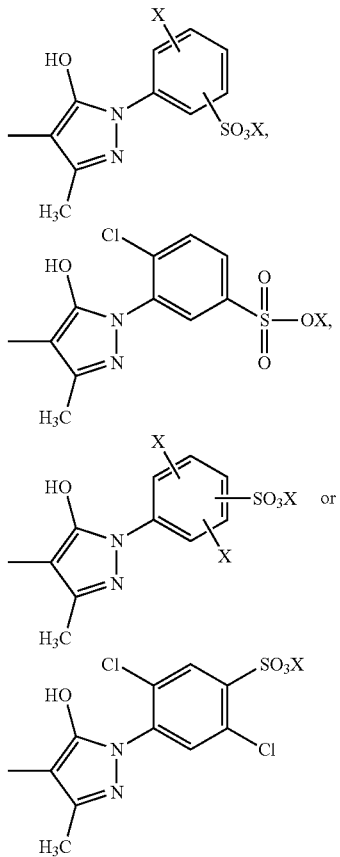

wherein X is as defined in 13, and each X may be the same or different.

[23] The reaction accelerating agent according to any of 13 to 22, wherein the compound represented by formula (I) is selected from the group consisting of a compound represented by the following formula:

[Formula 30]

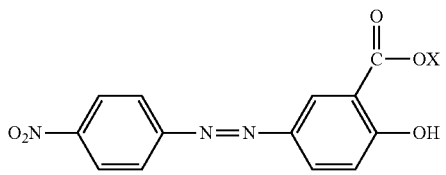

IV a compound represented by the following formula:

[Formula 31]

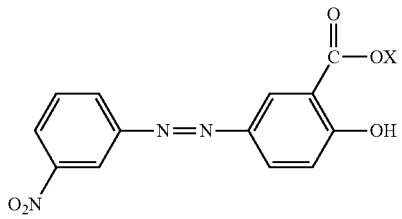

V wherein X is selected from the group consisting of —H, —Na, —K, and —Li,
a compound represented by the following formula:

[Formula 32]

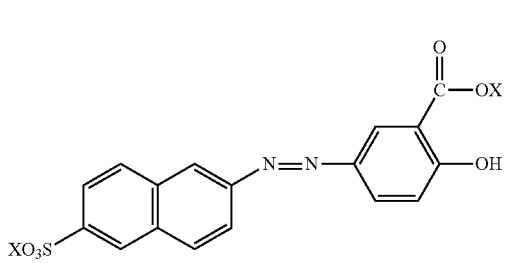

VI wherein X is selected from the group consisting of —H, —Na, —K, and —Li, and each X may be the same or different,
a compound represented by the following formula:

[Formula 33]

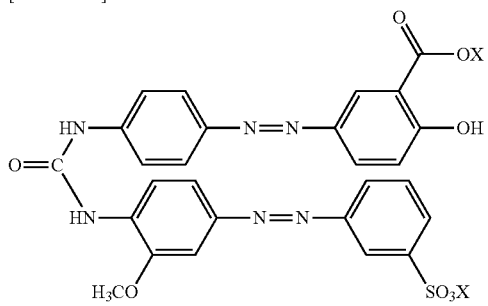

VII wherein X is selected from the group consisting of —H, —Na, —K, and —Li, and each X may be the same or different,
a compound represented by the following formula:

[Formula 34]

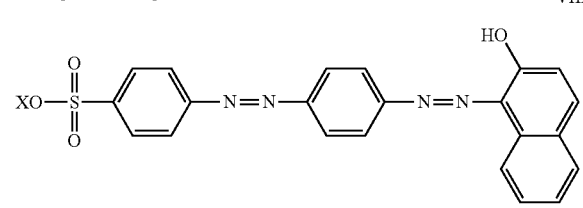

VIII wherein X is selected from the group consisting of —H, —Na, —K, and —Li,
a compound represented by the following formula:

[Formula 35]

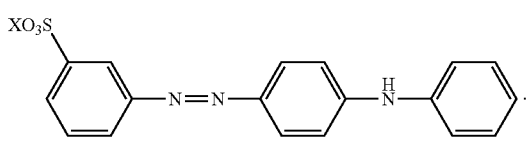

IX a compound represented by the following formula:

[Formula 36]

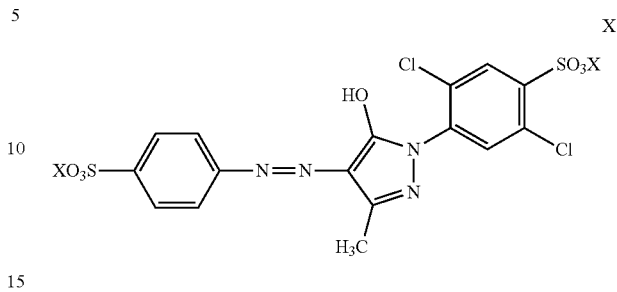

X wherein X is selected from the group consisting of —H, —Na, —K, and —Li, and each X may be the same or different,
a compound represented by the following formula:

[Formula 37]

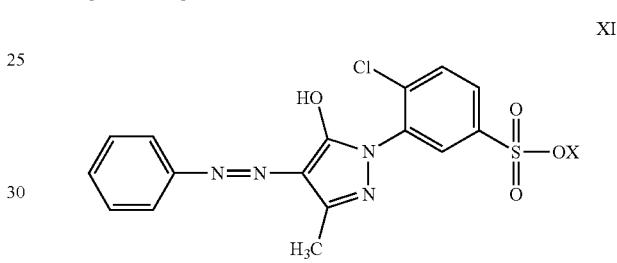

XI wherein X is selected from the group consisting of —H, —Na, —K, and —Li, and
a compound represented by the following formula:

[Formula 38]

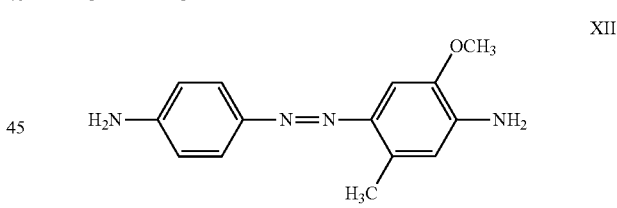

XII

[24] A composition comprising the reaction accelerating agent according to any of 13 to 23 and an oxidase.

[25] The composition according to 24, wherein the oxidase is an oxidase selected from the group consisting of amadoriase, sarcosine oxidase, and cholesterol oxidase.

The present specification encompasses the contents disclosed in Japanese Patent Application No. 2016-138547 on which the priority of the present application is based.

Advantageous Effects of the Invention

As an advantage (effect) of the present invention, it is possible to accelerate the enzymatic reaction catalyzed by an oxidase. This can lead to reduction of the amount of the enzyme necessary for measurement, shortening of reaction time even when using the same amount of enzyme, or enhancement of measurement sensitivity. In one embodiment, for example, the enzymatic reaction catalyzed by amadoriase can be accelerated. This can lead to decrease in the amount of the amadoriase formulated, for example, the amount of A1cOX formulated, into an HbA1c measurement reagent, or the amount of the amadoriase formulated into a GA measurement reagent, as compared with the case of not adding the amadoriase reaction accelerating agent (reaction accelerator) of the present invention. If the same amount of amadoriase is formulated, then since enzymatic reaction is accelerated, higher sensitivity of measurement and/or shortening of reaction time can be achieved. The same goes with other types of oxidases (e.g., sarcosine oxidase and cholesterol oxidase and the like).

BRIEF DESCRIPTION OF THE DRAWINGS

FIG. 1 shows results of measuring the absorbance ($A_{694}$ and $A_{751}$) of a reaction solution for light at wavelengths of 694 nm and 751 nm over time for 10 minutes after mixing of a diluted sample with the first reagent. The abscissa depicts time (min), and the ordinate depicts $A_{694/751}$ ($A_{694}$-$A_{751}$). The relationship between $A_{694/751}$ and $\Delta A_{9min}$ and $\Delta A_{10min}$ is also shown.

DESCRIPTION OF EMBODIMENTS

In one embodiment, the present invention provides an oxidase reaction accelerating agent. The term oxidase reaction accelerating agent refers to a compound capable of accelerating the enzymatic reaction catalyzed by an oxidase. The phrase "accelerate the enzymatic reaction catalyzed by an oxidase" means that a larger amount of product (hydrogen peroxide, and the like) is produced in the same reaction time, or the reaction is completed or almost completed in a shorter time, in the presence of the oxidase reaction accelerating agent of the present invention in a system as compared to the absence of the oxidase reaction accelerating agent in the system.

The oxidase reaction accelerating agent of the present invention is capable of accelerating the reaction of various oxidases. In one embodiment, the oxidase reaction accelerating agent of the present invention is capable of accelerating the reaction of an amadoriase. In this case, the oxidase reaction accelerating agent of the present invention may also be referred to as an amadoriase reaction accelerating agent. In one embodiment, the oxidase reaction accelerating agent of the present invention is capable of accelerating the reaction of a sarcosine oxidase. In this case, the oxidase reaction accelerating agent of the present invention may also be referred to as a sarcosine oxidase reaction accelerating agent. In one embodiment, the oxidase reaction accelerating agent of the present invention is capable of accelerating the reaction of a cholesterol oxidase. In this case, the oxidase reaction accelerating agent of the present invention may also be referred to as a cholesterol oxidase reaction accelerating agent. These names are given merely for the sake of convenience. For example, the same reaction accelerating agent compound may accelerate the reaction of an amadoriase and accelerate the reaction of a sarcosine oxidase. Such reaction accelerating agent falls under an amadoriase reaction accelerating agent and also falls under a sarcosine oxidase reaction accelerating agent. Thus, the designated names such as an amadoriase reaction accelerating agent must not be interpreted as a limiting the reaction accelerating agent of the present invention in any way. In the present specification, the reaction accelerating agent of the present invention means an oxidase reaction accelerating agent unless otherwise specified.

In one embodiment, the oxidase reaction accelerating agent of the present invention is capable of accelerating the reaction of an amadoriase. In one embodiment, examples of the amadoriase whose reaction is to be accelerated include, but are not limited to, amadoriases which recognize α-fructosyl valine (αFV), α-fructosyl valyl histidine (αFVH), and/or α-fructosyl hexapeptide (αF6P) as a substrate. In one embodiment, examples of the amadoriase whose reaction is to be accelerated include amadoriases which recognize ε-fructosyl lysine (ε-FK) as a substrate. In one embodiment, examples of the amadoriase whose reaction is to be accelerated include amadoriases capable of acting directly on hemoglobin A1c, i.e., hemoglobin A1c oxidase (A1cOX). In this case, the amadoriase reaction accelerating agent of the present invention may also be referred to as a hemoglobin A1c oxidase reaction accelerating agent.

In one embodiment, the present invention provides a method comprising the step of using an oxidase and an oxidase reaction accelerating agent. In one embodiment, the present invention provides, for example, a method for measuring an oxidase reaction product, comprising using an oxidase and an oxidase reaction accelerating agent. In another embodiment, the present invention provides a method for synthesizing a product, comprising using an oxidase and an oxidase reaction accelerating agent. In an alternative embodiment, the present invention provides a method for producing hydrogen peroxide, comprising using an oxidase and an oxidase reaction accelerating agent. This method is applicable to, for example, sterilization, washing, or oxidation reaction using the produced hydrogen peroxide.

In one embodiment, the present invention provides a method for measuring a substance to be measured, comprising the step of using an oxidase and an oxidase reaction accelerating agent. In one embodiment, the method of the present invention comprises the steps of: adding a first reagent containing peroxidase and the oxidase reaction accelerating agent to a sample which may contain the substance to be measured, followed by warming; adding thereto a second reagent containing a color developing agent and the oxidase whose reaction is to be accelerated, followed by warming; and measuring the absorbance of the sample. The first reagent containing a peroxidase and the oxidase reaction accelerating agent may be a single reagent or may be a combination of a plurality of reagents containing the individual components respectively. The second reagent containing a color developing agent and the oxidase whose reaction is to be accelerated may be a single reagent or may be a combination of a plurality of reagents containing the individual components respectively. In another embodiment, the measurement method of the present invention comprises the steps of: adding a first reagent containing a peroxidase, a color developing agent and the oxidase reaction accelerating agent to a sample which may contain the substance to be measured, followed by warming; adding thereto a second reagent containing the oxidase whose reaction is to be accelerated, followed by warming; and measuring the absorbance of the sample. Still, each component in the reagent may be a single reagent or may be a combination of a plurality of reagents containing the individual components respectively. The measurement may be qualitative or quantitative.

In an alternative embodiment, the measurement method of the present invention comprises the steps of: adding a measurement reagent containing peroxidase, the oxidase reaction accelerating agent, a color developing agent and the oxidase whose reaction is to be accelerated to a sample which may contain the substance to be measured, followed by warming; and measuring the absorbance of the sample. The measurement reagent containing a peroxidase, the oxidase reaction accelerating agent, a color developing agent and the oxidase whose reaction is to be accelerated may be a single reagent or may be a combination of a plurality of reagents containing the individual components respectively.

In one embodiment, the present invention provides a method for measuring HbA1c, comprising the step of using amadoriase and an amadoriase reaction accelerating agent. In one embodiment, the HbA1c measurement method of the present invention comprises the steps of: adding a first reagent containing a peroxidase and the amadoriase reaction accelerating agent to a sample which may contain HbA1c, followed by warming; adding thereto a second reagent containing a color developing agent and the amadoriase, followed by warming; and measuring the absorbance of the sample. The first reagent containing (comprising) a peroxidase and the amadoriase reaction accelerating agent may be a single reagent or may be a combination of a plurality of reagents containing the individual components respectively. The second reagent containing a color developing agent and the amadoriase may be a single reagent or may be a combination of a plurality of reagents containing the individual components respectively. In another embodiment, the HbA1c measurement method of the present invention comprises the steps of: adding a first reagent containing a peroxidase, a color developing agent and the amadoriase reaction accelerating agent to a sample which may contain HbA1c, followed by warming; adding thereto a second reagent containing the amadoriase, followed by warming; and measuring the absorbance of the sample. Again, each component in the reagent may be a single reagent or may be a combination of a plurality of reagents containing the individual components respectively. The measurement may be qualitative or quantitative. In one embodiment, total hemoglobin in the sample can be further quantified in the step of adding a first reagent containing a peroxidase and the amadoriase reaction accelerating agent, followed by warming. In one embodiment, the ratio of glycated hemoglobin to total hemoglobin, HbA1c %, in the sample can be further calculated from the quantified total hemoglobin and glycated hemoglobin.

In an alternative embodiment, the HbA1c measurement method of the present invention comprises the steps of: adding a measurement reagent containing peroxidase, the amadoriase reaction accelerating agent, a color developing agent and the amadoriase to a sample which may contain HbA1c, followed by warming; and measuring the absorbance of the reagent. The measurement reagent containing peroxidase, the amadoriase reaction accelerating agent, a color developing agent and the amadoriase may be a single reagent or may be a combination of a plurality of reagents containing the individual components respectively.

In one embodiment, an amadoriase capable of acting on a glycated substrate such as αFV, αFVH and/or αF6P can be used as the amadoriase. In this case, the HbA1c measurement method of the present invention may further comprise the step of pretreating HbA1c with protease. Any protease known in the art can be used as the protease. In another embodiment, amadoriase acting on ε-FK can be used as the amadoriase. This can be utilized in a method for measuring glycated albumin (GA). In this case, the GA measurement method may further comprise the step of pretreating GA with a protease. In an alternative embodiment, hemoglobin A1c oxidase (A1cOX) acting directly on HbA1c can be used as the amadoriase. In this case, pretreatment with protease need not be performed.

In one embodiment, the present invention provides a method for measuring sarcosine, comprising the step of using sarcosine oxidase and the reaction accelerating agent of the present invention. This measurement method may additionally comprise, as an upstream step, the step of converting creatinine to creatine with a creatinine amidohydrolase (also referred to as creatininase), and converting the creatine to sarcosine with creatine amidinohydrolase (also referred to as creatinase). This provides a method for measuring creatinine or creatine. In one embodiment, the measurement method of the present invention comprises the steps of: adding a first reagent containing peroxidase and the reaction accelerating agent of the present invention to a sample which may contain the substance to be measured (sarcosine), followed by warming; adding thereto a second reagent containing a color developing agent and the sarcosine oxidase, followed by warming; and measuring the absorbance of the sample. The first reagent containing peroxidase and the reaction accelerating agent of the present invention may be a single reagent or may be a combination of a plurality of reagents containing the individual components respectively. The second reagent containing a color developing agent and the sarcosine oxidase may be a single reagent or may be a combination of a plurality of reagents containing the individual components respectively. In another embodiment, the measurement method of the present invention comprises the steps of: adding a first reagent containing peroxidase, a color developing agent and the reaction accelerating agent of the present invention to a sample which may contain the substance to be measured, followed by warming; adding thereto a second reagent containing the sarcosine oxidase, followed by warming; and measuring the absorbance of the sample. Again, each component in the reagent may be a single reagent or may be a combination of a plurality of reagents containing the individual components respectively. The measurement may be qualitative or quantitative.

In an alternative embodiment, the measurement method of the present invention comprises the steps of: adding a measurement reagent containing a peroxidase, the reaction accelerating agent of the present invention, a color developing agent and the sarcosine oxidase to a sample which may contain the substance to be measured, followed by warming; and measuring the absorbance of the reagent. The measurement reagent containing peroxidase, the reaction accelerating agent of the present invention, a color developing agent and the oxidase whose reaction is to be accelerated may be a single reagent or may be a combination of a plurality of reagents containing the individual components respectively.

In one embodiment, the present invention provides a method for measuring cholesterol, comprising the step of using a cholesterol oxidase and the reaction accelerating agent of the present invention. This measurement method may additionally comprise, as an upstream step, the step of converting cholesterol ester to cholesterol with cholesterol esterase. In one embodiment, the measurement method of the present invention comprises the steps of: adding a first reagent containing peroxidase and the reaction accelerating agent of the present invention to a sample which may contain the cholesterol, followed by warming; adding thereto a second reagent containing a color developing agent and the cholesterol oxidase, followed by warming; and measuring the absorbance of the sample. The first reagent containing peroxidase and the reaction accelerating agent of the present invention may be a single reagent or may be a combination of a plurality of reagents containing the individual components respectively. The second reagent containing a color developing agent and the cholesterol oxidase may be a single reagent or may be a combination of a plurality of reagents containing the individual components respectively. In another embodiment, the measurement method of the present invention comprises the steps of: adding a first reagent containing peroxidase, a color developing agent and the reaction accelerating agent of the present invention to a sample which may contain the cholesterol, followed by warming; adding thereto a second reagent containing the cholesterol oxidase, followed by warming; and measuring the absorbance of the sample. Still, each component in the reagent may be a single reagent or may be a combination of a plurality of reagents containing the individual components respectively. The measurement may be qualitative or quantitative.

In an alternative embodiment, the measurement method of the present invention comprises the steps of: adding a measurement reagent containing peroxidase, the reaction accelerating agent of the present invention, a color developing agent and the cholesterol oxidase to a sample which may contain the cholesterol, followed by warming; and measuring the absorbance of the reagent. The measurement reagent containing peroxidase, the reaction accelerating agent of the present invention, a color developing agent and the cholesterol oxidase may be a single reagent or may be a combination of a plurality of reagents containing the individual components respectively.

The final concentration of the reaction accelerating agent of the present invention added to the sample solution is not particularly limited and can be in the range of, for example, 0.01 to 200 mM, 0.02 to 150 mM, 0.03 to 100 mM, 0.04 to 80 mM, 0.05 to 60 mM, 0.06 to 50 mM, 0.08 to 40 mM, 0.1 mM to 30 mM, 0.15 to 20 mM, 0.2 to 10 mM, 0.3 to 5 mM, or 0.4 to 3 mM, for example, 0.05 to 10 mM. The final concentration of the reaction accelerating agent of the present invention added to the sample solution is not particularly limited and can be, for example, 0.001 to 5% (w/v), 0.003 to 3% (w/v), 0.005 to 1% (w/v), 0.01 to 0.5% (w/v), 0.02 to 0.3% (w/v), or 0.03 to 0.1% (w/v). The order of addition of the reaction accelerating agent, other enzymes, and reagents is not limited, and these components may be added concurrently or sequentially.

For example, when the substance to be measured is a glycated substrate and the glycated substrate concentration in the sample solution is 0 to 0.5 mM, the final concentration of the amadoriase reaction accelerating agent added thereto can be, for example, 0.01 to 20 mM, for example, 0.02 to 10 mM.

For example, when the substance to be measured is HbA1c and the HbA1c concentration in the sample solution is 0 to 0.5 mM, the final concentration of the amadoriase reaction accelerating agent added thereto can be, for example, 0.01 to 20 mM, for example, 0.02 to 10 mM.

For example, when the substance to be measured is sarcosine and the sarcosine concentration in the sample solution is 0.1 to 2 mg/dL, the final concentration of the sarcosine oxidase reaction accelerating agent added thereto can be, for example, 0.01 to 20 mM, for example, 0.02 to 10 mM. In the present specification, the method in which sarcosine is the substance to be measured encompasses a method comprising, as an upstream step, the step of converting creatinine to creatine with creatinine amidohydrolase (also referred to as creatininase), and converting the creatine to sarcosine with creatine amidinohydrolase (also referred to as creatinase).

For example, when the substance to be measured is cholesterol and the cholesterol concentration in the sample solution is 1 to 1000 mg/dL, the final concentration of the cholesterol oxidase reaction accelerating agent added thereto can be, for example, 0.01 to 20 mM, for example, 0.02 to 10 mM.

In one embodiment, the total reaction time can be 60 minutes or shorter, 30 minutes or shorter, or 20 minutes or shorter, preferably 15 minutes or shorter, preferably approximately (about) 10 minutes. For example, the warming after the addition of the first reagent described above can be performed for 30 minutes or shorter, 20 minutes or shorter, 15 minutes or shorter, or 10 minutes, for example, approximately 5 minutes, and the warming after the addition of the second reagent described above can be performed for 30 minutes or shorter, 20 minutes or shorter, 15 minutes or shorter, or 10 minutes, for example, approximately 5 minutes. The concentration of each component in the measurement reagent with respect to the concentration range of the substance to be measured (e.g., glycated hemoglobin) presumably contained in the sample can be adjusted such that the reaction mediated by the oxidase (e.g., amadoriase) is completed or almost completed. The phrase "reaction is completed" means that the 100% of the substance to be measured (e.g., glycated hemoglobin or a glycated substrate) contained in the sample has reacted. The phrase "reaction is almost completed" means that, for example, 90% or more, 95% or more, 96% or more, 97% or more, or 98% or more, for example, 99% or more, of the substance to be measured (e.g., glycated hemoglobin or a glycated substrate) contained in the sample has reacted.

The measurement wavelength in the absorbance measurement can be selected depending on the color developing agent. The measurement wavelength of the absorbance can be, for example, 340 to 900 nm, 590 to 900 nm, 600 to 751 nm, or 610 to 730 nm. In one embodiment, the measurement may be performed at two measurement wavelengths $A_1$ and $A_2$, and the difference therebetween (also referred to as $A_1-A_2$ or $A_1/A_2$) can be obtained. The two measurement wavelengths $A_1$ and $A_2$ can be any two wavelengths in the range of 590 to 900 nm. For example, A, can be set to the absorption wavelength of a dye, and $A_2$ can be set to a background wavelength and then the difference therebetween $(A_1-A_2)$ can be calculated. In the case of using a phenothiazine derivative dye, the measurement wavelength of the absorbance can be 590 to 730 nm, for example, 610 to 710 nm. In the case of using a phenothiazine derivative dye, the background wavelength can be selected from a region where the phenothiazine derivative dye is rarely absorbed, for example, the range of higher than 710 nm and 900 nm or lower. For example, when $A_1$ is $A_{694}$ and $A_2$ is $A_{751}$, $A_{694}-A_{751}$ may be calculated therefrom. The absorption wavelength may be set to $A_1=A_{654}$. The absorbance measurement may be performed using an automatic analysis apparatus.

The color developing agent is not particularly limited and may preferably be a compound that changes absorbance through the catalytic reaction of peroxidase in the presence of hydrogen peroxide. Examples of the color developing agent include 4-aminoantipyrine, ADOS (N-ethyl-N-(2-hydroxy-3-sulfopropyl)-m-anisidine), ALOS (N-ethyl-N-(2-hydroxy-3-sulfopropyl)aniline), TOOS (N-ethyl-N-(2-hydroxy-3-sulfopropyl)-m-toluidine sodium), DA-67 (10-(carboxymethylaminocarbonyl)-3,7-bis(dimethylamino)-phenothiazine), and DA-64 (N-(carboxymethylaminocarbonyl)-4,4'-bis(dimethylamino)-dipbenylamine). ADOS, ALOS, and TOOS develop color when condensed with 4-aminoantipyrine. DA-64 and DA-67 develop color by mere incorporation alone without the need of 4-aminoantipyrine. In any of the cases, the coloring reaction is catalyzed by peroxidase. Further examples of the color developing agent include, but are not limited to, methylene blue, 10-(acetylaminocarbonyl)-3,7-bis(dimethylamino)phenothiazine, 10-(carboxymethylaminocarbonyl)-3,7-bis(dimethylamino)phenothiazine, 10-(phenylcarbonyl)-3,7-bis(dimethylamino)phenothiazine, 10-(3-(methylcarboxyamino)-hexamethyl-amino)-phenothiazine, 10-((3-(methylcarboxyamino)-4-methyl-phenyl)-amino)-phenothiazine, 10-((3-(methylcarboxyaminomethyl)-phenyl)-methylamino)-phenothiazine, 10-(1-naphthaleneamino)-phenothiazine, 10-(methyl)-phenothiazine, 10-(phenylamino)-phenothiazine, 10-(methylamino)-phenothiazine, azure A, azure B, azure C, toluidine blue O, 1,9-dimethyl-3,7-bis(dimethylamino)phenothiazine salt, methylene green and salts thereof, and leuco forms thereof. The color developing agent can be added such that its final concentration in the reaction solution is 0.001 to 10 mM, for example, 0.005 to 2 mM.

Any amadoriase, sarcosine oxidase, or cholesterol oxidase known in the art can be used as the oxidase, although the oxidase is not limited thereto. For sarcosine oxidases known in the art, see, for example, Patent Literatures 15 to 17. For cholesterol oxidases known in the art, see, for example, Patent Literature 19. The contents of these literatures (documents) are incorporated herein by reference in their entirety. Mutants or equivalents thereof may also be used.

Any amadoriase known in the art can be used as the amadoriase. Examples of the amadoriase include those acting on a glycated substrate such as αFV, αFVH and/or αF6P. See, for example, Patent Literatures 1 to 7 and 8 to 11. Other types of amadoriase known in the art may also be used. Further examples of the amadoriase include A1cOX acting directly on HbA1c, for example, those described in Patent Literatures 12 and 13. Other types of A1cOX having functions equivalent thereto may also be used. Further examples of the amadoriase include amadoriase acting on ε-FK, for example, those described in Patent Literature 20. The contents of these literatures are incorporated herein by reference in their entirety.

For the amadoriase reaction, amadoriase is added to a sample solution which may contain a glycated substrate or HbA1c so that the amadoriase can act on the substrate to produce hydrogen peroxide. In this procedure, the amadoriase reaction accelerating agent of the present invention is also included in the system.

The amadoriase acts on a glycated amino acid, a glycated peptide or a glycated protein having a glycated α- and/or ε-amino group and catalyzes the reaction of producing hydrogen peroxide and α-ketoaldehyde. In this procedure, this reaction is accelerated in the presence of the amadoriase reaction accelerating agent of the present invention in the system. However, the present invention is not bound to any specific mechanism of action.

The amadoriase reaction can be performed in a buffering solution (buffer solution). In the case of performing a pretreatment using a protease, the same or different buffering solution as or from that for the pretreatment reaction can be used in the amadoriase reaction. The pH of the reaction solution is not particularly limited and can be, for example, 3 to 11, 4 to 10, or 5 to 9, for example, 6 to 8. The reaction temperature can be, for example, 10 to 45° C., 10 to 38° C., or 20 to 37° C., for example, 25 to 37° C. The reaction time can be 0.1 to 60 minutes, 0.1 to 30 minutes, 0.1 to 20 minutes, 0.1 to 15 minutes, or 0.1 to 10 minutes, for example, 0.1 to 5 minutes.

The reaction using the sarcosine oxidase can be performed in a buffering solution. In the case of using creatininase and creatinase in an upstream step and converting creatinine to creatine and then to sarcosine, the same or different buffering solution as or from that for the reaction in the upstream step can be used in the reaction using the sarcosine oxidase. The pH of the reaction solution is not particularly limited and can be, for example, 3 to 11, 4 to 10, or 5 to 9, for example, 6 to 8. The reaction temperature can be, for example, 10 to 45° C., 10 to 38° C., or 20 to 37° C., for example, 25 to 37° C. The reaction time can be 0.1 to 60 minutes, 0.1 to 30 minutes, 0.1 to 20 minutes, 0.1 to 15 minutes, or 0.1 to 10 minutes, for example, 0.1 to 5 minutes.

The reaction using the cholesterol oxidase can be performed in a buffering solution. In the case of performing pretreatment using cholesterol esterase, the same or different buffering solution as or from that for the pretreatment reaction can be used in the cholesterol oxidase reaction. The pH of the reaction solution is not particularly limited and can be, for example, 3 to 11, 4 to 10, or 5 to 9, for example, 6 to 8. The reaction temperature can be, for example, 10 to 45° C., 10 to 38° C., or 20 to 37° C., for example, 25 to 37° C. The reaction time can be 0.1 to 60 minutes, 0.1 to 30 minutes, 0.1 to 20 minutes, 0.1 to 15 minutes, or 0.1 to 10 minutes, for example, 0.1 to 5 minutes.

The oxidase (e.g., amadoriase) can be added, for example, at a final concentration of 0.01 to 50 U/mL, 0.1 to 20 U/mL, or 0.2 to 10 U/mL, for example, 0.5 to 10 U/mL, to the sample, although depending on the amount of the substrate (e.g., a glycated substrate) contained in the sample solution. The enzymatic activity "U" of amadoriase against αFV as a substrate can be defined such that the amount of enzyme that produces 1 μmol of hydrogen peroxide in 1 minute with αFV as a substrate is 1 U. The enzymatic activity "U" of amadoriase against αFVH as a substrate can be defined such that the amount of enzyme that produces 1 μmol of hydrogen peroxide in 1 minute with αFVH as a substrate is 1 U. The enzymatic activity "U" of amadoriase against ε-FK as a substrate can be defined such that the amount of enzyme that produces 1 μmol of hydrogen peroxide in 1 minute with ε-FK as a substrate is 1 U. The enzymatic activity "U" of amadoriase against αF6P as a substrate can be defined such that the amount of enzyme that produces 1 μmol of hydrogen peroxide in 1 minute with αF6P as a substrate is 1 U. The enzymatic activity "U" of amadoriase against HbA1c as a substrate can be defined such that the amount of enzyme that produces 1 μmol of hydrogen peroxide in 1 minute with HbA1c as a substrate is 1 U. The enzymatic activity "U" of sarcosine oxidase against sarcosine as a substrate can be defined such that the amount of enzyme that produces 1 μmol of urea in 1 minute with sarcosine as a substrate is 1 U. The enzymatic activity "U" of cholesterol oxidase against cholesterol as a substrate can be defined such that the amount of enzyme that produces 1 μmol of hydrogen peroxide in 1 minute with cholesterol as a substrate is 1 U. In the present specification, the enzymatic activity "U" of the amadoriase is defined such that the amount of enzyme that produces 1 μmol of hydrogen peroxide in 1 minute with HbA1c as a substrate is 1 U, unless otherwise specified.

Any peroxidase known in the art can be used as the peroxidase. The peroxidase catalyzes the oxidation-reduction reaction between hydrogen peroxide and the color developing agent. The color developing agent develops color due to this reaction. The conditions for using the peroxidase are not particularly limited. The pH of the reaction solution, for example, is 5 to 9, and the treatment temperature, for example, is in the range of 10 to 40° C., preferably 25 to 37° C. The treatment time is not particularly limited and can be 0.1 to 60 minutes or 0.1 to 10 minutes, for example, 0.1 to 5 minutes. The peroxidase can be added at a final concentration of 0.01 to 300 KU/L, for example, 0.5 to 50 KU/L, to the reaction solution. The activity "U" of the peroxidase is defined such that the amount of the enzyme (POD) producing 1 mg of purpurogallin in 20 seconds under the following reaction conditions is 1 purpurogallin unit:

Reagent:
A. 5% (W/V) pyrogallol aqueous solution
B. 0.147 M $H_2O_2$ solution (1.67 ml of a 30% (W/V) $H_2O_2$ solution is diluted to 100 ml with distilled water)
C. 0.1 M phosphate buffer solution, pH 6.0 (for reaction mixture and enzyme dilution)
D. 2.0 N $H_2SO_4$ solution
Enzyme solution: an enzyme preparation is dissolved in a 0.1 M phosphate buffer solution, pH 6.0 cooled in ice in advance, and the solution is diluted to 3.0 to 6.0 purpurogallin U/P with the same buffer solution as above and preserved under ice cooling.

Procedures:
1 A reaction mixture of the components given below is prepared in a test tube (32ϕ×200 mm) and preliminarily warmed at 20° C. for approximately 5 minutes.
14.0 ml of distilled water
2.0 ml of an aqueous pyrogallol solution (A)
1.0 ml of an aqueous $H_2O_2$ solution (B)
2.0 ml of a phosphate buffer solution (C)
2 The reaction is started by the addition of 1.0 ml of an enzyme solution.
3 After reaction at 20° C. for precisely 20 seconds, the reaction is terminated by the addition of 1.0 ml of a $H_2SO_4$ solution (D). After the termination of the reaction, the produced purpurogallin is extracted from the mixture with 15 ml of ether. This operation is repeated 5 times, and the extracts are combined. Ether is further added thereto to adjust the whole amount to 100 ml. The absorbance of this solution is measured at 420 nm (OD test).
4 For a blind test, the reaction mixture 1 is left at 20° C. for 20 seconds. Then, 1.0 ml of the $H_2SO_4$ solution (D) is added thereto, followed by mixing. Subsequently, 1.0 ml of an enzyme solution is added thereto for preparation. This solution is subjected to ether extraction and absorbance measurement in the same manner as above (OD blank).
The calculation formula is as follows:

$$U/ml = \Delta OD(OD \text{ test} - OD \text{ blank}) \times \text{Dilution ratio}/$$
$$(0.117 \times 1 \text{ ml})$$
$$= \Delta OD \times 8.547 \times \text{Dilution ratio}$$
$$U/mg = U/ml \times 1/C$$

0.117: absorbance of 1 mg % purpurogallin ether solution at 420 nm
C: enzyme concentration (c mg/ml) at the time of dissolution
1 purpurogallin unit corresponds to 13.5 international units (under reaction conditions of 25° C. with o-dianisidine as a substrate).

The absorbance measurement can be carried out with any spectrophotometer or detection instrument known in the art. The absorbance of the reaction solution indicates the amount of the color developing agent that has developed color. The concentration of the substance to be measured (e.g., HbA1c) in the sample can be determined therefrom. For example, the absorbance of a standard material containing a substrate having a known concentration (e.g., glycated hemoglobin or a glycated substrate having a known concentration) is measured, and the relationship between the concentration and the absorbance can be plotted to prepare a calibration curve. Subsequently, the absorbance of a sample containing a substrate (e.g., glycated hemoglobin or a glycated substrate) of unknown concentration is measured, and the concentration of the substrate (e.g., glycated hemoglobin or a glycated substrate) can be determined from the calibration curve.

In one embodiment, the present invention provides a composition comprising an oxidase reaction accelerating agent. This composition may optionally comprise an oxidase, peroxidase, a buffer, a stabilizer, a color developing agent, a surfactant, and the like. An additional enzyme or reagent for measurement of a marker or a compound may also be added to the composition of the present invention.

In one embodiment, the present invention provides a composition for HbA1c measurement comprising an amadoriase reaction accelerating agent. This composition may optionally comprise amadoriase, peroxidase, a buffer, a stabilizer, a color developing agent, a surfactant, and the like. An additional enzyme or reagent for measurement of a marker other than HbA1c or a compound may also be added to the composition of the present invention.

In one embodiment, the present invention provides a composition for sarcosine measurement comprising a sarcosine oxidase reaction accelerating agent. This composition may optionally comprise creatinine amidohydrolase, creatine amidinohydrolase, sarcosine oxidase, peroxidase, a buffer, a stabilizer, a color developing agent, a surfactant, and the like. Creatine or creatinine can be measured by use of creatinine amidohydrolase, creatine amidinohydrolase, and peroxidase. Thus, in one embodiment, the present invention further provides a composition for creatine or creatinine measurement comprising a sarcosine oxidase reaction accelerating agent, creatinine amidohydrolase, creatine amidinohydrolase, sarcosine oxidase, and peroxidase.

In one embodiment, the present invention provides a composition for cholesterol measurement comprising a cholesterol oxidase reaction accelerating agent. This composition may optionally comprise cholesterol oxidase, cholesterol esterase, peroxidase, a buffer, a stabilizer, a color developing agent, a surfactant, and the like.

Examples of the buffer include N-[tris(hydroxymethyl)methyl]glycine, phosphate, acetate, carbonate, tris(hydroxymethyl)-aminomethane, borate, citrate, dimethylglutamate, Tricine, HEPES, MES, Bis-Tris, ADA, PIPES, ACES, MOPSO, BES, MOPS, TES, DIPSO, TAPSO, POPSO, HEPPSO, EPPS, Tricine, Bicine, TAPS, phthalic acid, and tartaric acid. The composition of the present invention may be appropriately further supplemented, if necessary, a solubilizer, a stabilizer, a reactivity improving agent, an HbA1c denaturant, or the like, such as a surfactant (n-octyl-β-D-glucoside, n-octyl-β-D-thioglucoside, n-dodecyl-β-D-maltoside, n-tetradecyl-β-D-makoside, n-octyl-β-D-maltoside, 1-dodecylpyridinium salt, hexadecyl trimethylammonium salt, tetradecyl trimethylammonium salt, dodecyl trimethylammonium salt, Triton X-100, Bridge 35, Bridge 58, Tween 80, cholate, n-heptyl-β-D-thioglucoside, 3-oxatridecyl-α-D-mannoside, n-nonyl-β-D-thiomaltoside, n-decyl-β-D-maltoside, n-undecyl-β-D-maltoside, trehalose C8, trehalose C10, trehalose C12, trehalose C14, trehalose C16, BIGCHAP, deoxy-BIGCHAP, MEGA- 8, MEGA-9, MEGA-10, hexadecylpyridinium salt, octadecyl trimethylammonium salt, decyl trimethylammonium salt, nonyl trimethylammonium salt, octyl trimethylammonium salt, hexyl trimethylammonium salt, sodium dodecyl sulfate, and the like), a reducing agent (dithiothreitol, mercaptoethanol, L-cysteine, and the like), nitrite, bovine serum albumin, or a saccharide (glycerin, lactose, sucrose, and the like).

When the amadoriase is A1cOX and the glycated substrate is HbA1c, HbA1c may be denatured in advance in order to enhance the reaction efficiency between A1cOX and HbA1c. Denaturation can be performed by surfactant treatment, heat treatment, or treatment with an acid or an alkali. In the case of performing both surfactant addition and heat treatment as the denaturation treatment, the order thereof is arbitrary (not restricted). The heat treatment can be performed using a temperature and a time sufficient for denaturing all or some of HbA1c. The treatment temperature can be, for example, 60° C. or higher, 70° C. or higher, 80° C. or higher, or 90° C. or higher, for example, 98° C. The treatment time can be, for example, 10 seconds or longer, 20 seconds, 30 seconds or longer, 1 minute or longer, or 2 minutes or longer, although depending on the temperature. Examples of the surfactant are as mentioned above, and the surfactant can be added at an appropriate concentration.

In one embodiment, the oxidase reaction accelerating agent of the present invention is a compound represented by the following formula (I):

[Formula 39]

$$R^1-N=N-R^2 \quad (I)$$

wherein
$R^1$ and $R^2$ are each independently an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents, wherein
said substituent(s) is selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, —CO—$NH_2$, —$R^3$, —NH—$R^4$, —NHCO—NH—$R^5$—N=N—$R^6$, —$SO_3X$, —COOX, Y, and Z;
X is selected from the group consisting of —H, —Na, —K, and —Li;
Y is selected from the group consisting of —H, —$SO_3X$, and —COOX;
Z is selected from the group consisting of —H, —$C_{1-6}$ alkyl, —O—$C_{1-6}$ alkyl, and —$SO_3X$;
each X, Y, and Z may be the same or different;
—$R^3$ is —H, or is an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents selected from the group consisting of —F, —Cl, —Br, —I, —At, —$C_1$, alkyl, —$C_{2-6}$ alkenyl, —$C_{2-6}$ alkynyl, =O, —OH, —O—$C_{1-6}$ alkyl, —$CONH_2$, —$NO_2$, —$NH_2$, and —$SO_3X$;
—$R^4$ is an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, —$SO_3X$, —COOX, Y, and Z; and $R^5$ and $R^6$ are each independently an aromatic 5- or 6-membered monocyclic carbocyclic ring or heterocyclic ring containing at least one nitrogen atom, sulfur atom or oxygen atom, or a 9- or 10-membered fused ring containing the aromatic 5- to 6-membered monocyclic carbocyclic ring or heterocyclic ring, wherein the ring may optionally be substituted with one or more substituents selected from the group consisting of —F, —Cl, —Br, —I, —At, —$C_{64}$ alkyl, —$C_{2-6}$ alkenyl, —$C_{2-6}$ alkynyl, =O, —OH, —O—$C_{1-6}$ alkyl, —O—$CH_3$, —$CONH_2$, —$NO_2$, —$NH_2$, —$SO_3X$, —COOX, Y, and Z,
provided that when $R^1$ or $R^2$ is an aromatic 5-membered monocyclic carbocyclic ring or heterocyclic ring containing at least one nitrogen atom, sulfur atom or oxygen atom, the heterocyclic ring is not substituted with —COOX.

Examples of the 5- or 6-membered monocyclic ring include 5- or 6-membered carbocyclic rings and 5- or 6-membered heterocyclic rings. The 9- or 10-membered fused ring may be a fused ring of a heterocyclic ring and a heterocyclic ring, a fused ring of a carbocyclic ring and a heterocyclic ring, or a fused ring of a carbocyclic ring and a carbocyclic ring.

In the case of a 5-membered monocyclic ring, the monocyclic ring may optionally be substituted with 1, 2, 3, or 4 substituents. In the case of a 6-membered monocyclic ring, the monocyclic ring may optionally be substituted with 1, 2, 3, 4 or 5 substituents. In the case of a 9-membered fused ring, the fused ring may optionally be substituted with 1, 2, 3, 4, 5, or 6 substituents. In the case of a 10-membered fused ring, the fused ring may optionally be substituted with 1, 2, 3, 4, 5, 6 or 7 substituents.

Examples of the aromatic monocyclic carbocyclic ring include a benzene ring. Examples of the fused ring of an aromatic carbocyclic ring and carbocyclic ring include a naphthalene ring.

Examples of the 5-membered heterocyclic ring include, but are not limited to, pyrroline, imidazoline, pyrazoline, pyrrolidine, imidazolidine, pyrazolidine, tetrahydrothiophene, tetrahydrofuran, and tetrahydropyrrole.

Examples of the 6-membered heterocyclic ring include, but are not limited to, piperidine, piperazine, morpholine, tetrazine, and oxazine.

Examples of the aromatic 5-membered heterocyclic ring include, but are not limited to, imidazole, pyrazole, oxazole, isoxazole, thiazole, isothiazole, thiophene, oxadiazole, e.g., 1,2,3-oxadiazole, 1,2,4-oxadiazole, 1,2,5-oxadiazole (also referred to as furazan), 1,3,4-oxadiazole, furan, pyrrole (1H-pyrrole, 2H-pyrrole), triazole (1,2,3-triazole, 1,2,4-triazole), tetrazole, pentazole, and thiadiazole.

Examples of the aromatic 6-membered heterocyclic compound include, but are not limited to, pyridine, pyrazine, pyrimidine, pyridazine, and triazine (1,2,3-triazine, 1,2,4-triazine, 1,3,5-triazine).

Examples of the fused ring include, but are not limited to, benzimidazole, benzoxazole, benzisoxazole, 1,3-benzodioxole, benzothiophene, benzo[c]thiophene, benzothiazole, indole (2,3-benzopyrrole), indazole, isoindole, purine, quinoline, isoquinoline, phthalazine, and isobenzofuran having a 9-membered ring.

Examples of the fused ring include, but are not limited to, benzodioxane, 1,4-benzodioxin, naphthyridine, quinoxaline, quinazoline, cinnoline, and pteridine having a 10-membered ring.

Examples of the —$C_{1-6}$ alkyl include methyl, ethyl, propyl (n-propyl, isopropyl), butyl (n-butyl, sec-butyl, isobutyl, tert-butyl), pentyl (n-pentyl, tert-pentyl, neopentyl, isopentyl, sec-pentyl, 3-pentyl), and hexyl (n-hexyl, isohexyl, neohexyl) groups.

Examples of the —$C_{2-6}$ alkenyl include an ethenyl group (vinyl group), a 1-propenyl group, a 2-propenyl group (allyl group), a 1-butenyl group, a 2-butenyl group, a 3-butenyl group, a pentenyl group, and a hexenyl group.

Examples of the —$C_{2-6}$ alkynyl include an ethynyl group, a 1-propynyl group, a 2-propynyl group, a 1-butynyl group, a 2-butynyl group, a 3-butynyl group, a pentynyl group, and a hexynyl group.

The —O—$C_{1-6}$ alkyl may also be referred to as a $C_{1-6}$ alkoxy group and examples thereof include linear or branched alkoxy groups such as methoxy, ethoxy, propoxy, butoxy, pentyloxy, and hexyloxy.

In one embodiment, $R^1$ and $R^2$ are each independently an aromatic 6-membered monocyclic carbocyclic ring, or a 10-membered fused ring containing the aromatic 6-membered monocyclic carbocyclic ring, wherein the ring may optionally be substituted with one or more substituents.

In one embodiment, $R^1$ and $R^2$ are each independently a group selected from the group consisting of

[Formula 40]

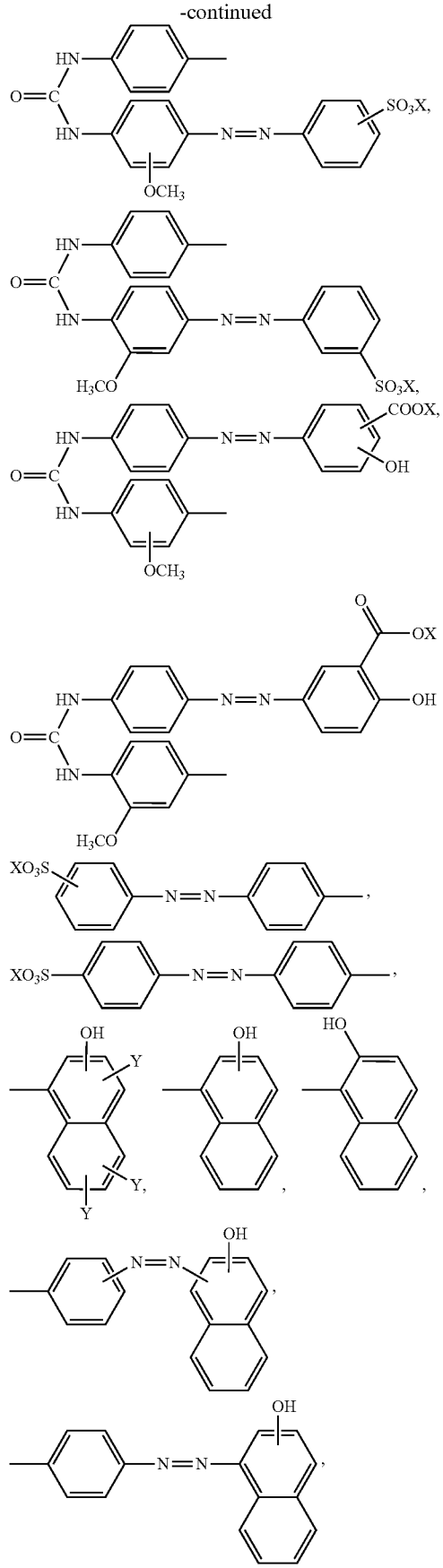
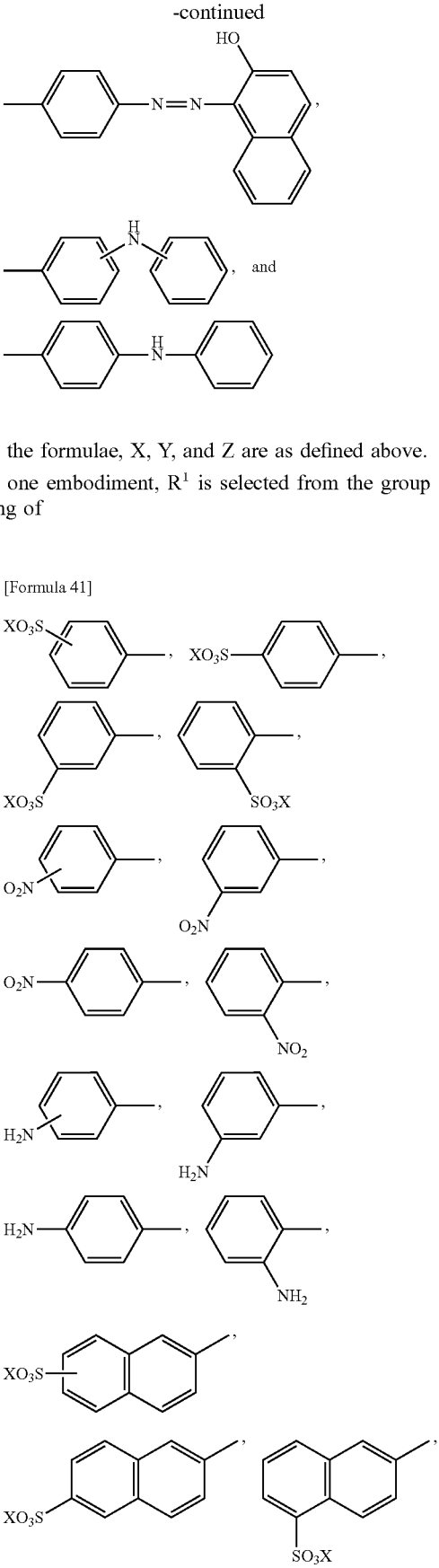
In the formulae, X, Y, and Z are as defined above.
In one embodiment, $R^1$ is selected from the group consisting of
[Formula 41]
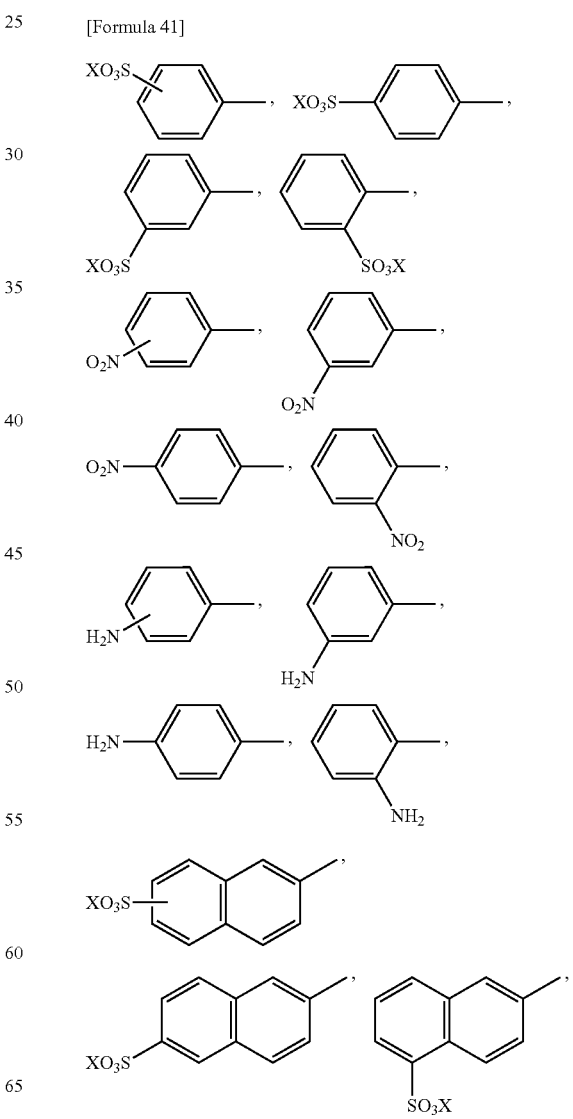

-continued

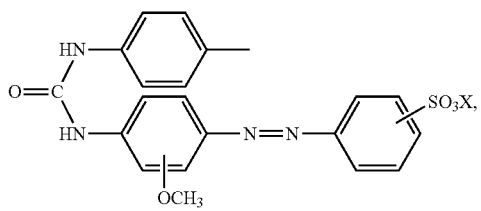

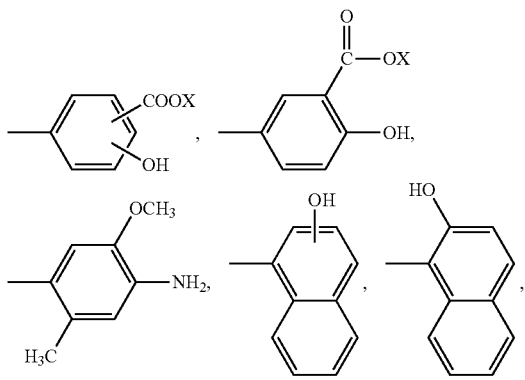

and $R^2$ is selected from the group consisting of

[Formula 42]

-continued

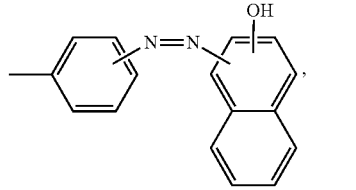

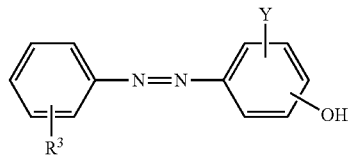

wherein X is as defined above.

In one embodiment, the oxidase reaction accelerating agent of the present invention comprises a compound represented by the following formula:

[Formula 43]

$$\text{(II)}$$

wherein

X is selected from the group consisting of —H, —Na, —K, and —Li;

Y is selected from the group consisting of —H, —SO₃X, and —COOX;

each X and Y may be the same or different;

—$R^3$ is —H or —NHCO—NH—$R^5$—N=N—$R^6$, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —$CONH_2$, —$NO_2$, —$NH_2$, and —$SO_3X$; and $R^5$ and $R^6$ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —O—$CH_3$, —$CONH_2$, —$NO_2$, —$NH_2$, and —$SO_3X$.

In one embodiment, the oxidase reaction accelerating agent of the present invention comprises a compound represented by any of the following formulae:

[Formula 44]

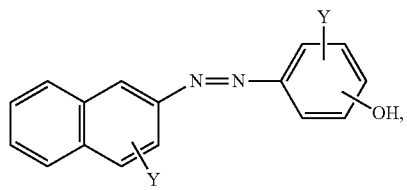

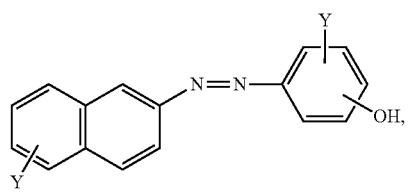

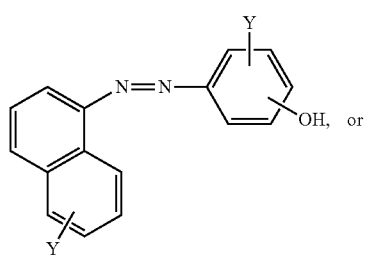

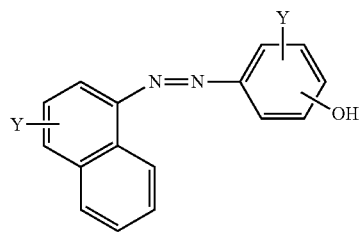

wherein
X is selected from the group consisting of —H, —Na, —K, and —Li;
Y is selected from the group consisting of —H, —$SO_3X$, and —COOX; and
each X and Y may be the same or different.

In one embodiment, the oxidase reaction accelerating agent of the present invention comprises a compound represented by the following formula:

[Formula 45]

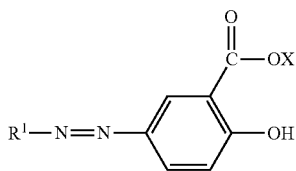

(III)

wherein
$R^1$ is a benzene ring or a naphthalene ring which may optionally be substituted with one or more substituents, wherein
said substituent(s) is selected from the group consisting of —$NO_2$, —$SO_3X$, and

[Formula 46]

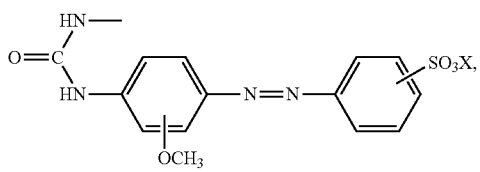

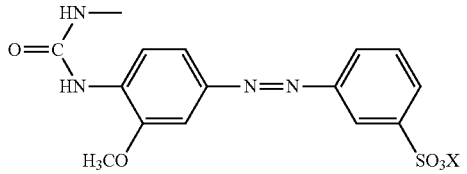

and
X is selected from the group consisting of —H, —Na, —K, and —Li.

In one embodiment, $R^1$ is an aromatic 6-membered monocyclic carbocyclic ring which may optionally be substituted with one or more substituents, and $R^2$ is an aromatic 5-membered monocyclic heterocyclic ring containing at least one nitrogen atom, sulfur atom or oxygen atom wherein said ring may optionally be substituted with one or more substituents.

In one embodiment, $R^2$ is an aromatic 5-membered monocyclic heterocyclic ring containing two nitrogen atoms wherein said ring may optionally be substituted with one or more substituents, and the heterocyclic ring is substituted with

[Formula 47]

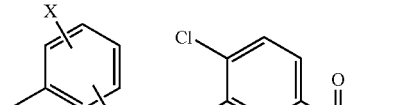

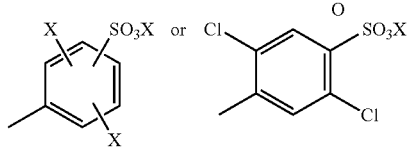

wherein X is as defined above, and each X may be the same or different.

In one embodiment, $R^2$ is

[Formula 48]

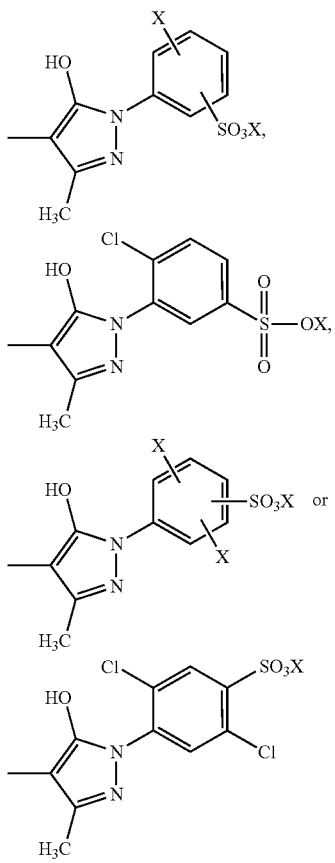

wherein X is as defined above, and each X may be the same or different.

In one embodiment, the oxidase reaction accelerating agent of the present invention is an azobenzene derivative, for example, an azobenzene derivative that exhibits water solubility, for example, a compound having an azobenzene-4-sulfonic acid skeleton.

In one embodiment, the oxidase reaction accelerating agent of the present invention is a compound selected from the group consisting of a compound represented by the following formula:

[Formula 49]

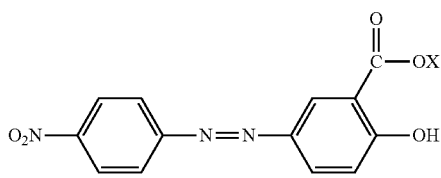

IV wherein X is selected from the group consisting of —H, —Na, —K, and —Li, for example, Mordant Orange 1 (CAS 2243-76-7) represented by the following formula:

[Formula 50]

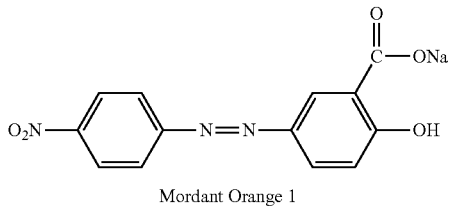

Mordant Orange 1 a compound represented by the following formula:

[Formula 51]

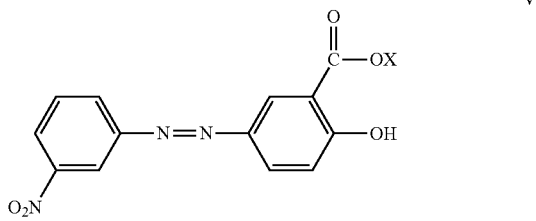

V wherein X is selected from the group consisting of —H, —Na, —K, and —Li, for example, Alizarin Yellow GG (CAS 584-42-9) represented by the following formula:

[Formula 52]

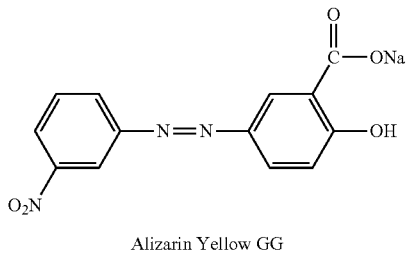

Alizarin Yellow GG a compound represented by the following formula:

[Formula 53]

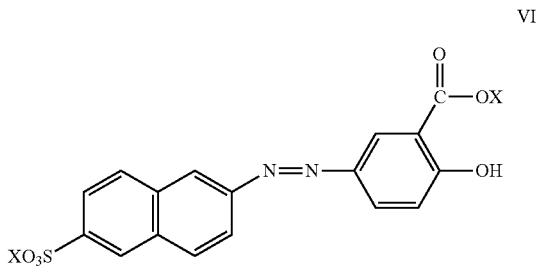

VI wherein X is selected from the group consisting of —H, —Na, —K, and —Li, and each X may be the same or different, for example, Chrome Yellow (CAS6054-97-3) represented by the following formula:

[Formula 54]

Chrome Yellow a compound represented by the following formula:

[Formula 55]

VII wherein X is selected from the group consisting of —H, —Na, —K, and —Li, and each X may be the same or different, for example, Direct Yellow 44 (CAS8005-52-5) represented by the following formula:

[Formula 56]

Direct Yellow 44 a compound represented by the following formula:

[Formula 57]

VIII wherein X is selected from the group consisting of —H, —Na, —K, and —Li, for example, Acid Red 151 (CAS6406-56-0) represented by the following formula:

[Formula 58]

Acid Red 151 a compound represented by the following formula:

[Formula 59]

IX wherein X is selected from the group consisting of —H, —Na, —K, and —Li, for example, Acid Yellow 36 (CAS587-98-4) represented by the following formula:

[Formula 60]

Acid Yellow 36 a compound represented by the following formula:

[Formula 61]

X wherein X is selected from the group consisting of —H, —Na, —K, and —Li, and each X may be the same or different, for example, Xylene Fast Yellow 2G (CAS 6359-98-4) represented by the following formula:

[Formula 62]

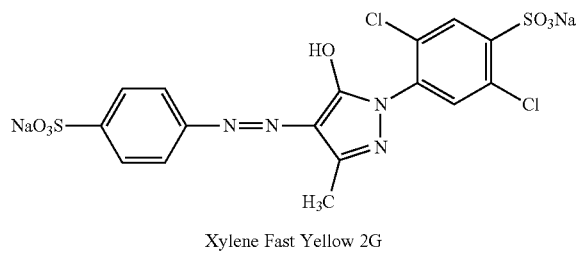

Xylene Fast Yellow 2G and a compound represented by the following formula:

[Formula 63]

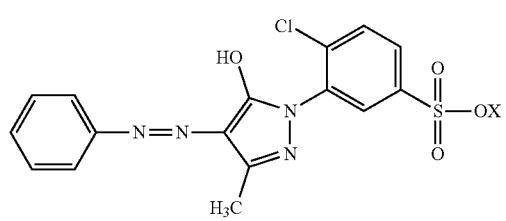

XI wherein X is selected from the group consisting of —H, —Na, —K, and —Li, for example, Acid Yellow 34 (CAS 6359-90-6) represented by the following formula:

[Formula 64]

Acid Yellow 34

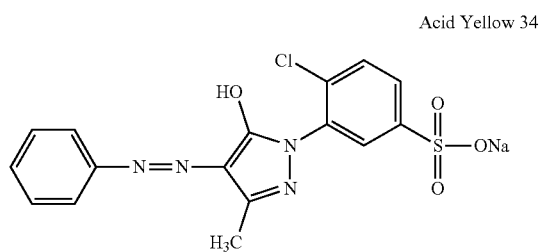

and Disperse Diazo Black 3BF (CAS 6232-57-1) represented by the following formula:

[Formula 65]

Disperse Diazo Black 3BF

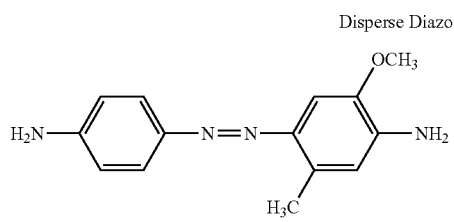

The compound represented by the following formula (Tartrazine, C A S 1934-21-0) is excluded from the reaction accelerating agent of the present invention:

[Formula 66]

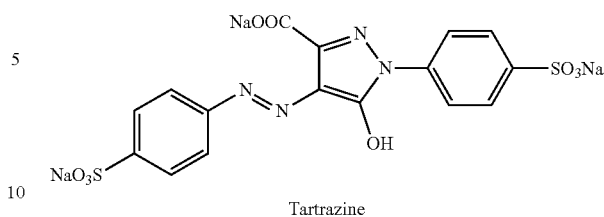

Tartrazine

These compounds may be commercially available products, or salts thereof may be used. Other compounds of formula I may be synthesized by use of a routine approach or may be commercially available products, or salts thereof may be used.

In one embodiment, the oxidase reaction accelerating agent of the present invention is capable of accelerating the reaction of amadoriase. Examples of such reaction accelerating agent (also referred to as an amadoriase reaction accelerating agent) include, but are not limited to, the compounds described above, for example, the compounds of formula I, formula II, and formula III, the compound of formula IV, for example, Mordant Orange 1, the compound of formula V, for example, Alizarin Yellow GG, the compound of formula VI, for example, Chrome Yellow, the compound of formula VII, for example, Direct Yellow 44, the compound of formula VIII, for example, Acid Red 151, the compound of formula IX, for example, Acid Yellow 36, the compound of formula X, for example, Xylene Fast Yellow 2G, the compound of formula XI, for example, Acid Yellow 34 and the compound of formula XII, for example, Disperse Diazo Black 3BF.

In one embodiment, the oxidase reaction accelerating agent of the present invention is capable of accelerating the reaction of sarcosine oxidase. Examples of such reaction accelerating agent (also referred to as a sarcosine oxidase reaction accelerating agent) include, but are not limited to, the compounds described above, for example, the compounds of formula I, formula II, and formula III, the compound of formula IV, for example, Mordant Orange 1, the compound of formula V, for example, Alizarin Yellow GG, the compound of formula VI, for example, Chrome Yellow, the compound of formula VII, for example, Direct Yellow 44, the compound of formula VIII, for example, Acid Red 151, the compound of formula X, for example, Xylene Fast Yellow 2G, and the compound of formula XII, for example, Disperse Diazo Black 3BF.

In one embodiment, the oxidase reaction accelerating agent of the present invention is capable of accelerating the reaction of cholesterol oxidase. Examples of such reaction accelerating agent (also referred to as a cholesterol oxidase reaction accelerating agent) include, but are not limited to, the compounds described above, for example, the compounds of formula I, formula II, and formula m, the compound of formula IV, for example, Mordant Orange 1, the compound of formula V, for example, Alizarin Yellow GG, the compound of formula VI, for example, Chrome Yellow, the compound of formula VII, for example, Direct Yellow 44, the compound of formula VIII, for example, Acid Red 151, the compound of formula IX, for example, Acid Yellow 36, the compound of formula XI, for example, Acid Yellow 34 and the compound of formula XII, for example, Disperse Diazo Black 3BF.

(Example of HbA1c Measurement Method)

Examples of the HbA1c measurement reagent and measurement method of the present invention will be described below. However, the present invention is not limited by these examples.

The following reagents for HbA1c measurement are prepared.

HbA1c standard material
Certified Reference Material for Measurement of HbA1c, JCCRM 423-9b (manufactured by Reference Material Institute for Clinical Chemistry Standards)
Total hemoglobin concentration: 133 g/l,
HbA1c concentration, 3 levels (NGSP values: 5.61%, 7.71%, 10.55%)
First reagent (solution containing peroxidase and leuco dye)
30 mM MOPS-NaOH buffer solution, pH 6.5
15 mM Tris
0.2% (w/v) n-dodecyl-β-D-maltoside (manufactured by Dojindo Laboratories)
4 mM $NaNO_2$
10 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
Second reagent (solution containing A1cOX)
10 mM MOPS-NaOH buffer solution, pH 6.5
5.3 mg/ml CFP-DH4 (A1cOX)

HbA1c is measured according to the following procedures using Bio Majesty JCA-BM1650 (manufactured by JEOL Ltd.). 8 µl of the HbA1c standard material diluted 12.5-fold with ion-exchange water is added to 96 µl of the first reagent, and the mixture is incubated at 37° C. for 5 minutes. Then, 24 µl of the second reagent is added thereto, and the quantitative reaction of hydrogen peroxide resulting from the oxidation of the β-chain amino terminus of HbA1c is allowed to progress at 37° C. for 5 minutes. The absorbance ($A_{694}$ and $A_{751}$) of the reaction solution for light at wavelengths of 694 nm and 751 nm is measured over time for 10 minutes after the mixing of the diluted standard material with the first reagent to determine $A_{694/751}$ ($A_{694}-A_{751}$). The concentration of the HbA1c standard material is plotted on the abscissa against $A_{694/751}$ 10 minutes after the mixing of the diluted standard material with the first reagent on the ordinate to prepare a calibration curve representing the correlation between the HbA1c concentration and $A_{694/751}$.

Next, the same measurement as above is performed using a sample of unknown HbA1c concentration instead of the HbA1c standard material. The HbA1c concentration of the sample is determined using $A_{694/751}$ 10 minutes after the mixing of the diluted sample with the first reagent, and the calibration curve prepared above.

Whether or not the compound accelerates oxidase reaction can be evaluated by comparing the progression of the reaction with the addition of a candidate compound to the system and the progression of the reaction without the addition (of candidate compound).

(Example of Measurement Method Using Sarcosine Oxidase)

Examples of the measurement reagent and the measurement method using sarcosine oxidase will be described below. However, the present invention is not limited by these examples. The enzymatic activity of the sarcosine oxidase is defined such that the enzymatic activity of the sarcosine oxidase producing 1 µmol of urea in 1 minute with sarcosine as a substrate is 1 unit (U).

A. Preparation of Reagent

The following solutions are prepared as reagents for reaction.
1) 0.2 M sarcosine, 100 mM Tris-HCl, 2 mM KCl, 0.05% Triton-X100, pH 7.7
2) 80 U/ml POD solution
3) 0.2% phenol solution
4) 0.2% 4-aminoantipyrine solution
5) 0.3% SDS solution
6) 20 mM Tris-HCl, 1 mM KCl, 0.2% BSA, pH 7.7 (enzyme diluting solution)

Subsequently, these solutions are mixed in the following amounts to prepare an activity measurement solution.
1) 5 ml
2) 1 ml
3) 2 ml
4) 1 ml B. Measurement Method The measurement is performed as follows.
1) 0.95 ml of the activity measurement solution is preincubated at 37° C. for 5 minutes.
2) 0.05 ml of an enzyme solution (adjusted to 0.04 U/ml to 0.16 U/ml with the enzyme diluting solution) is added thereto, followed by mixing.
3) The mixture is reacted at 37° C. for 10 minutes.
4) After the reaction for 10 minutes, the 0.3% SDS solution is mixed therewith.
5) The mixture is left at 25° C. for 10 minutes, followed by the measurement of absorbance at 495 nm (OD sample).

A blank value is measured by mixing the 0.3% SDS solution before the mixing of the enzyme solution OD blank).

(Activity Conversion Expression)

$$U/ml = (ODsample - ODblank) \times 0.95$$

(Example of Measurement Method Using Cholesterol Oxidase)

Examples of the measurement reagent and the measurement method using cholesterol oxidase will be described below. However, the present invention is not limited by these examples. A method for measuring the amount of hydrogen peroxide will be taken as an example of the method for measuring the enzymatic activity of the cholesterol oxidase. In the activity measurement of the cholesterol oxidase given below, cholesterol is used as a substrate unless otherwise specified. The enzymatic titer of the cholesterol oxidase is defined such that the amount of the enzyme producing 1 µmol of hydrogen peroxide in 1 minute when measured with cholesterol as a substrate is 1 U.

A. Preparation of Reagent (1) Reagent 1: Cholesterol Solution 500 mg of cholesterol (manufactured by Wako Pure Chemical Industries, Ltd.) is added to 5.0 ml of Triton X-100 and dissolved by stirring on a heater. To this solution, 90 ml of ion-exchange water is added. Then, the mixture is boiled and then cooled on ice, and 4.0 g of sodium cholate (manufactured by Nacalai Tesque, Inc.) is added thereto and dissolved. Then, the mixture is brought to 100 ml.

(2) Reagent 2: 6.0% Phenol Solution 6.0 g of phenol is dissolved in ion-exchange water into 100 ml.

(3) Reagent 3: 0.15% Peroxidase Solution 150 mg is dissolved in 100 ml of a 0.1 M potassium phosphate buffer (pH 7.0).

(4) Reagent 4: 4-Aminoantipyrine Solution 1.76 g of 4-aminoantipyrine (manufactured by Wako Pure Chemical Industries, Ltd.) is dissolved in ion-exchange water, and the solution is brought to 100 ml.

B. Measurement Method 4.0 ml of reagent 1 and 51 ml of a 0.1 M potassium phosphate buffer solution (pH 7.0) are mixed. Then, 2.0 ml of reagent 2, 2.0 ml of reagent 3, and 1.0 ml of reagent 4 are added thereto in order, followed by mixing. This mixture is aliquoted (dispensed) at 3.0 ml/test tube and preserved under ice cooling. For measurement, the 3.0 ml aliquot is warmed at 37° C. for 5 minutes, and 50 µl of enzyme solution is added thereto, followed by mixing. The absorbance is measured at 500 nm using a spectrophotometer (U-3010, manufactured by Hitachi, Ltd.). The measurement value (ΔODtest) is defined as change in absorbance per minute from 2 minutes later to 4 minutes later at 500 nm. The control solution (ΔODblank) is the same as above with the exception that 50 µl of a 20 mM potassium phosphate buffer solution (pH 7.0) containing 0.2% bovine serum albumin is added instead of the enzyme solution. A value calculated according to the following expression was used as an enzymatic activity value (U/ml).

$$U/ml = \frac{\Delta OD/\min(\Delta ODtest - \Delta ODblank) \times 3.05(ml) \times \text{Dilution ratio}}{13.78 \times 1/2 \times 1.0 \times 0.05(ml)} \quad [\text{Mathematical Formula 1}]$$

13.78: the mmol molecular extinction coefficient ($cm^2$/micromole) under the measurement conditions described above 1/2: the coefficient based on 1 molecule of Quinoneimine dye formed from 2 molecules of $H_2O_2$ produced by the enzymatic reaction.

1.0: light path (cm).

EXAMPLES

The present invention will be described more specifically with reference to the Examples given below. However, the present invention is not limited by these examples. Commercially available products were used as the reagents unless otherwise specified.

[Example 1] Preparation of Plasmid pKK223-3-CFP-DH2 Carrying an Amadoriase Gene

The amino acid sequence of an amadoriase acting on HbA1c (CFP-DH2, see International Publication No. WO 2015/060429) is shown in SEQ ID NO: 1. In order to prepare pKK223-3-CFP-DH2, a pKK223-3 vector having an insert of CFP-DH2 gene (SEQ ID NO: 2), an E. coli JM109 strain comprising pKK223-3-CFP-DH2 was inoculated to 3 ml of LB-amp medium [1% (w/v) Bacto Tryptone, 0.5% (w/v) peptone, 0.5% (w/v) NaCl, 50 µg/ml ampicillin] and shake-cultured at 37° C. for 16 hours to prepare the culture.

The culture was centrifuged at 10,000×g for 1 minute to harvest and a bacterial body was obtained. From this bacterial body, pKK223-3-CFP-DH2 was extracted and purified using GenElute Plasmid Miniprep Kit (manufactured by Sigma-Aldrich Co. LLC) to obtain 2.5 µg of recombinant plasmid pKK223-3-CFP-DH2.

[Example 2] Site-Directed Mutagenesis of pKK223-3-CFP-DH2

PCR reaction was performed under conditions given below with the obtained pKK223-3-CFP-DH2 as a template using synthetic oligonucleotides of SEQ ID NOs: 3 and 4 and KOD-Plus-(manufactured by Toyobo Co., Ltd.).

That is, 5 µl of 10×KOD-Plus-buffer solution, 5 µl of a mixed solution of dNTPs prepared to contain 2 mM each of dNTPs, 2 µl of a 25 mM $MgSO_4$ solution, 50 ng of the templated pKK223-3-CFP-DH2, 15 µmol each of the synthetic oligonucleotides, and 1 unit of KOD-Plus-were mixed, and the whole amount was adjusted to 50 µl with sterilized water. The prepared reaction solution was incubated at 94° C. for 2 minutes, followed by 30 repetitive cycles each involving "94° C. for 15 seconds"–"50° C. for 30 seconds"–"68° C. for 6 minutes", using a thermal cycler (manufactured by Eppendorf AG).

To the obtained reaction solution, a restriction enzyme DpnI (manufactured by NEW ENGLAND BioLabs Inc.) was added, and the mixture was reacted at 37° C. to cleave the template DNA remaining therein. Then, E. coli JM109 was transformed with the resultant and spread on LB-amp agar medium. A grown colony was inoculated to LB-amp medium and shake-cultured, and plasmid DNA was isolated in the same manner as in Example 1. The nucleotide sequence of DNA encoding the amadoriase in the plasmid was determined using a multi-capillary DNA analysis system Applied Biosystems 3130xl Genetic Analyzer (manufactured by Life Technologies Corp.) to obtain a plasmid (pKK223-3-CFP-DH3) carrying the gene of a mutated amadoriase (CFP-DH3, SEQ ID NO: 5) in which arginine at position 64 of the amino acid sequence of SEQ ID NO: 1 is substituted with glycine.

Subsequently, PCR reaction under the aforementioned conditions using pKK223-3-CFP-DH3 as a template, oligonucleotides of SEQ ID NOs: 6 and 7, and KOD-Plus-, the transformation of E. coli JM109, and the sequencing of DNA encoding amadoriase in plasmid DNA carried by a grown colony were carried out. As a result, a plasmid (pKK223-3-CFP-DH4) was obtained, carrying a gene of a mutated amadoriase (CFP-DH4, SEQ ID NO: 8) in which arginine at position 64 is substituted with glycine and leucine at position 110 of the amino acid sequence of SEQ ID NO: 1 is substituted with tyrosine, respectively.

[Example 3] Production and Purification of pKK223-3-CFP-DH4

The E. coli JM109 strain harboring the plasmid (pKK223-3-CFP-DH4) carrying the CFP-DH4 gene was inoculated to 200 ml of LB-amp medium supplemented with IPTG (final concentration: 0.1 mM), and cultured at 25° C. for 16 hours. Each cultured bacterial body thus obtained was washed with a 2 mM potassium phosphate buffer solution (pH 8.0) and then, the bacterial body was suspended in the same buffer solution as above, ultrasonicated, and centrifuged at 20,000×g for 10 minutes to prepare 40 ml of a crude enzyme solution.

A column loaded with Q-Sepharose FF (manufactured by GE Healthcare Japan Corp.) was equilibrated with a 2 mM potassium phosphate buffer solution (pH 8.0). Then, the prepared crude enzyme solution containing CFP-DH4 was applied thereto to allow the amadoriase to bind to the anion-exchange resin. Then, 20 column volumes of 4 mM potassium phosphate buffer solution (pH 8.0) was injected thereto to elute contaminating proteins. Then, the protein bound to the resin was eluted with a 4 mM potassium phosphate buffer solution (pH 8.0) containing 30 mM NaCl, and a fraction exhibiting amadoriase activity was recovered.

Each fraction exhibiting amadoriase activity thus obtained was concentrated with Amicon Ultra Ultracel-30K (manufactured by Millipore Corp.) and purified with HiLoad 26/60 Superdex 200. A 10 mM potassium phosphate buffer solution (pH 6.5) containing 150 mM NaCl was used for the equilibration of the resin and the elution. The purity of each eluted fraction was evaluated by SDS-PAGE, and a fraction free of contaminating proteins was recovered and used as a purified preparation of CFP-DH4.

[Example 4] Measurement of Absorbance when HbA1c Detection Reaction was Completed In this Example, the amount of change in absorbance when an excess amount of A1cOX is used and HbA1c detection reaction was completed is determined.

A reagent for HbA1c measurement having the following composition was prepared, and the measurement of HbA1c was carried out using Bio Majesty JCA-BM1650 (manufactured by JEOL Ltd.).
(Sample)
Blood cells (10.4% HbA1c (NGSP value))
(First reagent-A)
30 mM MOPS-NaOH buffer solution, pH 6.5
15 mM Tris
0.2% (w/v) n-dodecyl-β-D-maltoside (manufactured by Dojindo Laboratories)
4 mM $NaNO_2$
10 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
0.04% (w/v) of the compound of Comparative Example 2 (Wako Pure Chemical Industries, Ltd.), any one compound of the present invention (all from Tokyo Chemical Industry Co., Ltd. except for Acid Yellow 34 from MP Biomedicals, LLC), or compound-free (Comparative Example 1) ion-exchange water as shown in Table 1
(Second Reagent-A)
10 mM MOPS-NaOH buffer solution, pH 6.5
5.3 mg/ml CFP-DH4 (A cOX)

8 μl of the sample diluted 51-fold with ion-exchange water was added to 96 μl of the first reagent-A, and the mixture was incubated at 37° C. for 5 minutes. Then, 24 μl of the second reagent-A was added thereto, and the quantitative reaction of hydrogen peroxide resulting from the oxidation of the β-chain amino terminus of HbA1c was allowed to progress at 37° C. for 5 minutes. The absorbance ($A_{694}$ and $A_{751}$) of the reaction solution for light at wavelengths of 694 nm and 751 nm was measured over time for 10 minutes after the mixing of the diluted sample with the first reagent-A to determine the value subtracting of $A_{751}$ from $A_{694}$, i.e., the value $A_{694/751}$. Subsequently, ΔA was calculated by subtracting, from $A_{694/751}$, the value of (104/128) times $A_{694/751}$ 4.8 minutes after mixing the diluted sample with the first reagent-A. Incidentally, 4.8 minutes after the mixing of the diluted sample with the first reagent-A represents the time immediately before the addition of the second reagent-A. ΔA 9 minutes and 10 minutes after the mixing of the diluted sample with the first reagent ($ΔA_{9min}$ and $ΔA_{10min}$) are shown in Table 1. Further, as an example, the relationship between $A_{694/751}$ and $ΔA_{9min}$ and $ΔA_{10min}$ of Comparative Example 2 is shown in FIG. 1.

TABLE 1

| | $ΔA_{9\ min}$ | $ΔA_{10\ min}$ |
|---|---|---|
| Not added (Comparative Example 1) | 0.009 | 0.009 |
| Tartrazine (Comparative Example 2) | 0.032 | 0.032 |
| Mordant Orange 1 (Present invention 1) | 0.016 | 0.016 |
| Alizarin Yellow GG (Present invention 2) | 0.016 | 0.016 |
| Chrome Yellow (Present invention 3) | 0.024 | 0.024 |
| Direct Yellow 44 (Present invention 4) | 0.017 | 0.017 |
| Acid Red 151 (Present invention 5) | 0.014 | 0.014 |
| Acid Yellow 36 (Present invention 6) | 0.011 | 0.011 |
| Xylene Fast Yellow 2G (Present invention 7) | 0.015 | 0.015 |
| Acid Yellow 34 (Present invention 8) | 0.011 | 0.011 |

As shown in Table 1, no difference between $ΔA_{9min}$ and $ΔA_{10min}$ was observed for the compounds of the present invention and Comparative Examples. In other words, it can be recognized that the quantitative reaction of HbA1c, i.e., the quantitative reaction of hydrogen peroxide resulting from the oxidation of HbA1c, was completed in 10 minutes after the mixing of the diluted sample with the first reagent-A. Accordingly, in Examples 4 and 5, $ΔA_{10min}$ in each Comparative Example or the present invention was defined as ΔA when 100% of the quantitative reaction of HbA1c progressed under each condition ($ΔA_{100\%}$).

[Example 5] Calculation of Effect of Accelerating HbA1c Detection Reaction by the Compound of Present Invention Next, in this Example, the degree of acceleration of HbA1c detection reaction by the compound of the present invention was determined using a small amount of A1cOX.

A reagent for HbA1c measurement having the following composition was prepared, and the measurement of HbA1c was carried out using Bio Majesty JCA-BM1650 (manufactured by JEOL Ltd.).
(Sample)
Blood cells (10.4% HbA1c (NGSP value))
(First reagent)
30 mM MOPS-NaOH buffer solution, pH 6.5
15 mM Tris
0.2% (w/v) n-dodecyl-3-D-maltoside (manufactured by Dojindo Laboratories)
4 mM $NaNO_2$
10 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
0.04% (w/v) of the compound of Comparative Example 2, any one compound of the present invention, or compound-free (Comparative Example 1) ion-exchange water as shown in Table 2
(Second Reagent-B)
10 mM MOPS-NaOH buffer solution, pH 6.5
1.1 mg/ml CFP-DH4 (A cOX)

8 μl of the sample diluted 51-fold with ion-exchange water was added to 96 μl of the first reagent, and the mixture was incubated at 37° C. for 5 minutes. Then, 24 μl of the second reagent-B was added thereto, and the quantitative reaction of hydrogen peroxide resulting from the oxidation of the β-chain amino terminus of HbA1c was allowed to progress at 37° C. for 5 minutes. The absorbance ($A_{664}$ and $A_{751}$) of the reaction solution for light at wavelengths of 694 nm and 751 nm was measured over time for 10 minutes after the mixing of the diluted sample with the first reagent to determine the value of subtraction of $A_{751}$ from $A_{694}$, i.e., the value $A_{694/751}$. Subsequently, ΔA was calculated by subtracting, from $A_{694/751}$, the value of (104/128) times $A_{694/751}$ 4.8 minutes after the mixing of the diluted sample with the first reagent. Incidentally, 5 minutes after the mixing of the diluted sample with the first reagent represents the time immediately before the addition of the second reagent-B.

Next, ΔA calculated in this Example was divided by $ΔA_{100\%}$ defined in Example 4 to calculate the degree of progression of HbA1c detection reaction. The degree of progression of HbA1c detection reaction 7.5 and 10 minutes after the mixing of the diluted sample with the first reagent (in other words, 2.5 and 5 minutes after the addition of the second reagent-B) is shown in Table 2.

TABLE 2

|  | Degree of progression of reaction (%) after 7.5 minutes | Degree of progression of reaction (%) after 10 minutes |
| --- | --- | --- |
| Not added (Comparative Example 1) | 51 | 73 |
| Tartrazine (Comparative Example 2) | 38 | 62 |
| Mordant Orange 1 (Present invention 1) | 80 | 94 |
| Alizarin Yellow GG (Present invention 2) | 76 | 91 |
| Chrome Yellow (Present invention 3) | 53 | 77 |
| Direct Yellow 44 (Present invention 4) | 77 | 96 |
| Acid Red 151 (Present invention 5) | 55 | 80 |
| Acid Yellow 36 (Present invention 6) | 53 | 81 |
| Xylene Fast Yellow 2G (Present invention 7) | 58 | 83 |
| Acid Yellow 34 (Present invention 8) | 75 | 95 |

As shown in Table 2, Mordant Orange 1, Alizarin Yellow GG, Chrome Yellow, Direct Yellow 44, Acid Red 151, Acid Yellow 36, Xylene Fast Yellow 2G, and Acid Yellow 34 were found to have the effect of accelerating the HbA1c detection reaction.

[Example 6] Measurement of Absorbance when Fructosyl Valyl Histidine Detection Reaction Mediated by Fructosyl Peptide Oxidase was Completed In this Example the amount of change in absorbance is determined when the detection reaction of the substrate fructosyl valyl histidine was completed using an excess amount of fructosyl peptide oxidase (FPOX-CET), which is an oxidase.

A reagent for fructosyl valyl histidine measurement having the following composition was prepared, and the measurement of fructosyl valyl histidine using fructosyl peptide oxidase was carried out using Bio Majesty JCA-BM1650 (manufactured by JEOL Ltd.).

(Sample)
32 μM fructosyl valyl histidine (manufactured by Kikkoman Biochemifa Company)
(First Reagent-B)
30 mM MOPS-NaOH buffer solution, pH 7.0
0.2% (v/v) Triton X-100 (manufactured by Wako Pure Chemical Industries, Ltd.)
10 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
0.04% (w/v) of the compound of Comparative Example 2, any one compound of the present invention, or compound-free (Comparative Example 1) ion-exchange water as shown in Table 1
(Second Reagent-C)
10 mM MOPS-NaOH buffer solution, pH 7.0
4.8 U/ml FPOX-CET (manufactured by Kikkoman Biochemifa Company)

8 μl of the sample was added to 96 μl of the first reagent-B, and the mixture was incubated at 37° C. for 5 minutes. Then, 24 μl of the second reagent-C was added thereto, and the quantitative reaction of hydrogen peroxide resulting from the oxidation of fructosyl valyl histidine was allowed to progress at 37° C. for 5 minutes. The absorbance ($A_{694}$ and $A_{751}$) of the reaction solution for light at wavelengths of 694 nm and 751 nm was measured over time for 10 minutes after the mixing of the sample with the first reagent-B to determine the value of subtraction of $A_{751}$ from $A_{694}$, i.e., the value $A_{694/751}$. Subsequently, ΔA was calculated by subtracting, from $A_{674/751}$, the value of (104/128) times $A_{694/751}$ 4.8 minutes after the mixing of the sample with the first reagent-B. Incidentally, 4.8 minutes after the mixing of the sample with the first reagent-B represents the time immediately before the addition of the second reagent-C. ΔA 9 minutes and 10 minutes after the mixing of the diluted sample with the first reagent-B ($ΔA_{9min}$ and $ΔA_{10min}$) are shown in Table 3.

TABLE 3

|  | $ΔA_{9\,min}$ | $ΔA_{10\,min}$ |
| --- | --- | --- |
| Not added (Comparative Example 1) | 0.016 | 0.016 |
| Chrome Yellow (Present invention 3) | 0.064 | 0.064 |
| Direct Yellow 44 (Present invention 4) | 0.043 | 0.043 |
| Xylene Fast Yellow 2G (Present invention 7) | 0.027 | 0.027 |
| Acid Yellow 34 (Present invention 8) | 0.032 | 0.033 |

As shown in Table 3, no difference between $ΔA_{9min}$ and $ΔA_{10min}$ was observed for the compounds of the present invention and Comparative Examples. In other words, it can be recognized that the quantitative reaction of fructosyl valyl histidine, i.e., the quantitative reaction of hydrogen peroxide resulting from the oxidation of fructosyl valyl histidine, was completed in 10 minutes after the mixing of the diluted sample with the first reagent-B. Accordingly, in Examples 6 and 7, $ΔA_{10min}$ in each Comparative Example or the present invention was defined as ΔA when 100% of the quantitative reaction of HbA1c progressed under each condition ($ΔA_{100\%}$).

[Example 7] Calculation of Effect of Accelerating Fructosyl Valyl Histidine Detection Reaction Mediated by Fructosyl Peptide Oxidase by the Compound of Present Invention Next, in this Example, the degree of acceleration of fructosyl valyl histidine detection reaction by the compound of the present invention was determined using a small amount of fructosyl peptide oxidase.

A reagent for fructosyl valyl histidine measurement having the following composition was prepared, and the measurement of fructosyl valyl histidine was carried out using Bio Majesty JCA-BM 1650 (manufactured by JEOL Ltd.).
(Sample)
32 µM fructosyl valyl histidine (manufactured by Kikkoman Biochemifa Company)
(First Reagent-B)
30 mM MOPS-NaOH buffer solution, pH 7.0
0.2% (v/v) Triton X-100 (manufactured by Wako Pure Chemical Industries, Ltd.)
10 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
0.04% (w/v) of the compound of Comparative Example 2, any one compound of the present invention, or compound-free (Comparative Example 1) ion-exchange water as shown in Table 1
(Second Reagent-D)
10 mM MOPS-NaOH buffer solution, pH 7.0
0.48 U/ml FPOX-CET (manufactured by Kikkoman Biochemifa Company)

8 µl of the sample was added to 96 µl of the first reagent-B, and the mixture was incubated at 37° C. for 5 minutes. Then, 24 µl of the second reagent-D was added thereto, and the quantitative reaction of hydrogen peroxide resulting from the oxidation of fructosyl valyl histidine was allowed to progress at 37° C. for 5 minutes. The absorbance ($A_{694}$ and $A_{751}$) of the reaction solution for light at wavelengths of 694 nm and 751 nm was measured over time for 10 minutes after the mixing of the sample with the first reagent-B to determine the value of subtraction of $A_{751}$ from $A_{694}$, i.e., the value $A_{694/751}$. Subsequently, ΔA was calculated by subtracting, from $A_{694/751}$, the value of (104/128) times $A_{694/751}$ 4.8 minutes after the mixing of the sample with the first reagent-B. Incidentally, 5 minutes after the mixing of the sample with the first reagent-B represents the time immediately before the addition of the second reagent-D.

Next, ΔA calculated in this Example was divided by $ΔA_{1000\%}$ defined in Example 6 to calculate the degree of progression of fructosyl valyl histidine detection reaction. The degree of progression of fructosyl valyl histidine detection reaction 7.5 and 10 minutes after the mixing of the sample with the first reagent-B (in other words, 2.5 and 5 minutes after the addition of the second reagent-D) is shown in Table 4.

TABLE 4

|  | Degree of progression of reaction (%) after 7.5 minutes | Degree of progression of reaction (%) after 10 minutes |
| --- | --- | --- |
| Not added (Comparative Example 1) | 57 | 81 |

TABLE 4-continued

|  | Degree of progression of reaction (%) after 7.5 minutes | Degree of progression of reaction (%) after 10 minutes |
| --- | --- | --- |
| Chrome Yellow (Present invention 3) | 62 | 86 |
| Direct Yellow 44 (Present invention 4) | 66 | 88 |
| Xylene Fast Yellow 2G (Present invention 7) | 63 | 96 |
| Acid Yellow 34 (Present invention 8) | 62 | 86 |

As shown in Table 4, Chrome Yellow, Direct Yellow 44, Xylene Fast Yellow 2G, and Acid Yellow 34 were found to have the effect of accelerating the fructosyl valyl histidine detection reaction.

[Example 8] Measurement of Absorbance when Fructosyl Valine Detection Reaction Mediated by Fructosyl Amino Acid Oxidase was Completed In this Example, the amount of change in absorbance is determined when the detection reaction of the substrate fructosyl valine was completed using an excess amount of fructosyl amino acid oxidase (FAOD-E), which is an oxidase.

A reagent for fructosyl valine measurement having the following composition was prepared, and the measurement of fructosyl valine using fructosyl amino acid oxidase was carried out using Bio Majesty JCA-BM 1650 (manufactured by JEOL Ltd.).
(Sample)
32 µM fructosyl valine (manufactured by Kikkoman Biochemifa Company)
(First Reagent-C)
30 mM MOPS-NaOH buffer solution, pH 8.0
0.2% (v/v) NYMEEN F-215 (manufactured by NOF Corp.)
10 U/ml peroxidase PEO-301 (Toyobo Co., Ltd.)
0.023 mM 10-(carboxymethylaminocarbonyl)-3,7-bis(dimethylamino)phenothiazine sodium
(DA-67, manufactured by Wako Pure Chemical Industries, Ltd.)
0.04% (w/v) of the compound of Comparative Example 2, any one compound of the present invention, or compound-free (Comparative Example 1) ion-exchange water as shown in Table 1
(Second Reagent-E)
10 mM MOPS-NaOH buffer solution, pH 8.0
21.4 U/ml FAOD-E (manufactured by Kikkoman Biochemifa Company)

8 µl of the sample was added to 96 µl of the first reagent-C, and the mixture was incubated at 37° C. for 5 minutes. Then, 24 µl of the second reagent-E was added thereto, and the quantitative reaction of hydrogen peroxide resulting from the oxidation of fructosyl valine was allowed to progress at 37° C. for 5 minutes. The absorbance ($A_6$% and $A_{751}$) of the reaction solution for light at wavelengths of 694 nm and 751 nm was measured over time for 10 minutes after the mixing of the sample with the first reagent-C to determine the value of subtraction of $A_{751}$ from $A_{694}$, i.e., the value $A_{694/751}$. Subsequently, ΔA was calculated by subtracting, from $A_{694/751}$, the value of (104/128) times $A_{694/751}$ 4.8 minutes after the mixing of the sample with the first reagent-C. Incidentally, 4.8 minutes after the mixing of the sample with the first reagent-C represents the time immediately before the addition of the second reagent-E. ΔA 9 minutes and 10 minutes after the mixing of the diluted sample with the first reagent-C (ΔA$_{9min}$ and ΔA$_{10min}$) are shown in Table 5.

TABLE 5

|  | ΔA$_{9\,min}$ | ΔA$_{10\,min}$ |
|---|---|---|
| Not added (Comparative Example 1) | 0.023 | 0.024 |
| Mordant Orange 1 (Present invention 1) | 0.049 | 0.051 |
| Alizarin Yellow GG (Present invention 2) | 0.044 | 0.046 |
| Chrome Yellow (Present invention 3) | 0.066 | 0.067 |
| Disperse Diazo Black 3BF (Present invention 9) | 0.062 | 0.061 |

As shown in Table 5, no difference between ΔA$_{9min}$ and ΔA$_{10min}$ was observed for the compounds of the present invention and Comparative Examples. In other words, it can be recognized that the quantitative reaction of fructosyl valine, i.e., the quantitative reaction of hydrogen peroxide resulting from the oxidation of fructosyl valine, was completed in 10 minutes after the mixing of the diluted sample with the first reagent-C. Accordingly, in Examples 8 and 9, ΔA$_{10min}$ in each Comparative Example or the present invention was defined as ΔA when 100% of the quantitative reaction of HbA1c progressed under each condition (ΔA$_{100\%}$).

[Example 9] Calculation of Effect of Accelerating Fructosyl Valine Detection Reaction Mediated by Fructosyl Amino Acid Oxidase by the Compound of Present Invention Next, in this Example, the degree of acceleration of fructosyl valine detection reaction by the compound of the present invention was determined using a small amount of fructosyl amino acid oxidase.

A reagent for fructosyl valine measurement having the following composition was prepared, and the measurement of fructosyl valine was carried out using Bio Majesty JCA-BM1650 (manufactured by JEOL Ltd.).
(Sample)
32 μM fructosyl valine (manufactured by Kikkoman Biochemifa Company)
(First Reagent-C)
30 mM MOPS-NaOH buffer solution, pH 8.0
0.2% (v/v) NYMEEN F-215 (manufactured by NOF Corp.)
10 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
0.04% (w/v) of the compound of Comparative Example 2, any one compound of the present invention, or compound-free (Comparative Example 1) ion-exchange water as shown in Table 1
(Second Reagent-F)
10 mM MOPS-NaOH buffer solution, pH 8.0
2.14 U/ml FAOD-E (manufactured by Kikkoman Biochemifa Company)

8 μl of the sample was added to 96 μl of the first reagent-C, and the mixture was incubated at 37° C. for 5 minutes. Then, 24 μl of the second reagent-F was added thereto, and the quantitative reaction of hydrogen peroxide resulting from the oxidation of fructosyl valine was allowed to progress at 37° C. for 5 minutes. The absorbance (A$_{694}$ and A$_{751}$) of the reaction solution for light at wavelengths of 694 nm and 751 nm was measured over time for 10 minutes after the mixing of the sample with the first reagent-C to determine the value of subtraction of A$_{751}$ from A$_{694}$, i.e., the value A$_{694/751}$. Subsequently, ΔA was calculated by subtracting, from A$_{694/751}$, the value of (104/128) times A$_{694/751}$ 4.8 minutes after the mixing of the sample with the first reagent-C. Incidentally, 5 minutes after the mixing of the sample with the first reagent-C represents the time immediately before the addition of the second reagent-F.

Next, ΔA calculated in this Example was divided by ΔA$_{100\%}$ defined in Example 8 to calculate the degree of progression of fructosyl valine detection reaction. The degree of progression of fructosyl valine detection reaction 7.5 and 10 minutes after the mixing of the sample with the first reagent-C (in other words, 2.5 and 5 minutes after the addition of the second reagent-F) is shown in Table 6.

TABLE 6

|  | Degree of progression of reaction (%) after 7.5 minutes | Degree of progression of reaction (%) after 10 minutes |
|---|---|---|
| Not added (Comparative Example 1) | 29 | 48 |
| Mordant Orange 1 (Present invention 1) | 37 | 59 |
| Alizarin Yellow GG (Present invention 2) | 38 | 62 |
| Chrome Yellow (Present invention 3) | 43 | 68 |
| Disperse Diazo Black 3BF (Present invention 9) | 86 | 89 |

As shown in Table 6, Mordant Orange 1, Alizarin Yellow GG, Chrome Yellow, and Disperse Diazo Black 3BF were found to have the effect of accelerating fructosyl valine detection reaction.

[Example 10] Measurement of Absorbance when Sarcosine Detection Reaction Mediated by Sarcosine Oxidase was Completed In this Example, the amount of change in absorbance is determined when the detection reaction of the substrate sarcosine (N-methylglycine) was completed using an excess amount of sarcosine oxidase (SOD-TE), which is an oxidase.

A reagent for sarcosine measurement having the following composition was prepared, and the measurement of sarcosine using sarcosine oxidase was carried out using Bio Majesty JCA-BM 1650 (manufactured by JEOL Ltd.).
(Sample)
32 μM sarcosine (manufactured by Wako Pure Chemical Industries, Ltd.)
(First Reagent-D)
30 mM MOPS-NaOH buffer solution, pH 8.0
0.2% (v/v) NP-10 (manufactured by HELM)
10 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
0.04% (w/v) of the compound of Comparative Example 2, any one compound of the present invention, or compound-free (Comparative Example 1) ion-exchange water as shown in Table 1

(Second Reagent-G)
10 mM MOPS-NaOH buffer solution, pH 8.0
123 U/ml SOD-TE (manufactured by Kikkoman Biochemifa Company)

8 µl of the sample was added to 96 µl of the first reagent-D, and the mixture was incubated at 37° C. for 5 minutes. Then, 24 µl of the second reagent-G was added thereto, and the quantitative reaction of hydrogen peroxide resulting from the oxidation of sarcosine was allowed to progress at 37° C. for 5 minutes. The absorbance ($A_{694}$ and $A_{751}$) of the reaction solution for light at wavelengths of 694 nm and 751 nm was measured over time for 10 minutes after the mixing of the sample with the first reagent-D to determine the value of subtraction of $A_{751}$ from $A_{694}$, i.e., the value $A_{694/751}$. Subsequently, ΔA was calculated by subtracting, from $A_{694/751}$, the value of (104/128) times A % s 4.8 minutes after the mixing of the sample with the first reagent-D. Incidentally, 4.8 minutes after the mixing of the sample with the first reagent-D represents the time immediately before the addition of the second reagent-G. ΔA 9 minutes and 10 minutes after the mixing of the diluted sample with the first reagent-D ($ΔA_{9min}$ and $ΔA_{10min}$) are shown in Table 7.

TABLE 7

|  | $ΔA_{9\ min}$ | $ΔA_{10\ min}$ |
|---|---|---|
| Not added (Comparative Example 1) | 0.082 | 0.083 |
| Mordant Orange 1 (Present invention 1) | 0.327 | 0.328 |
| Alizarin Yellow GG (Present invention 2) | 0.197 | 0.197 |
| Chrome Yellow (Present invention 3) | 0.186 | 0.186 |
| Direct Yellow 44 (Present invention 4) | 0.315 | 0.315 |
| Acid Red 151 (Present invention 5) | 0.212 | 0.212 |
| Xylene Fast Yellow 2G (Present invention 7) | 0.158 | 0.158 |
| Disperse Diazo Black 3BF (Present invention 9) | 0.156 | 0.156 |

As shown in Table 7, no difference between $ΔA_{9min}$ and $ΔA_{10min}$ was observed for the compounds of the present invention and Comparative Examples. In other words, it can be recognized that the quantitative reaction of sarcosine, i.e., the quantitative reaction of hydrogen peroxide resulting from the oxidation of sarcosine, was completed in 10 minutes after the mixing of the diluted sample with the first reagent-D. Accordingly, in Examples 10 and 11, $ΔA_{10min}$ in each Comparative Example or the present invention was defined as ΔA when 100% of the quantitative reaction of sarcosine progressed under each condition ($ΔA_{100\%}$).

[Example 11] Calculation of Effect of Accelerating Sarcosine Detection Reaction Mediated by Sarcosine Oxidase by the Compound of Present Invention Next, in this Example, the degree of acceleration of sarcosine detection reaction by the compound of the present invention was determined using a small amount of sarcosine oxidase.

A reagent for sarcosine measurement having the following composition was prepared, and the measurement of sarcosine was carried out using Bio Majesty JCA-BM1650 (manufactured by JEOL Ltd.).

(Sample)
32 µM sarcosine (manufactured by Wako Pure Chemical Industries, Ltd.)
(First reagent-D)
30 mM MOPS-NaOH buffer solution, pH 8.0
0.2% (v/v) NP-10 (manufactured by HELM)
10 U/ml peroxidase PEO-301 (Toyobo Co., Ltd.)
0.023 mM 10-(carboxymethylaminocarbonyl)-3,7-bis(dimethylamino)phenothiazine sodium
(DA-67, manufactured by Wako Pure Chemical Industries, Ltd.)
0.04% (w/v) of the compound of Comparative Example 2, any one compound of the present invention, or compound-free (Comparative Example 1) ion-exchange water as shown in Table 1
(Second Reagent-H)
10 mM MOPS-NaOH buffer solution, pH 8.0
12.3 U/ml SOD-TE (manufactured by Kikkoman Biochemifa Company)

8 µl of the sample was added to 96 Cl of the first reagent-D, and the mixture was incubated at 37° C. for 5 minutes. Then, 24 µl of the second reagent-H was added thereto, and the quantitative reaction of hydrogen peroxide resulting from the oxidation of sarcosine was allowed to progress at 37° C. for 5 minutes. The absorbance ($A_{694}$ and $A_{751}$) of the reaction solution for light at wavelengths of 694 nm and 751 nm was measured over time for 10 minutes after the mixing of the sample with the first reagent-D to determine the value of subtraction of $A_{751}$ from $A_{694}$, i.e., the value $A_{694/751}$. Subsequently, ΔA was calculated by subtracting, from $A_{694/751}$, the value of (104/128) times $A_{694/751}$ 4.8 minutes after the mixing of the sample with the first reagent-D. Incidentally, 5 minutes after the mixing of the sample with the first reagent-D represents the time immediately before the addition of the second reagent-H.

Next, ΔA calculated in this Example was divided by $ΔA_{100\%}$ defined in Example 10 to calculate the degree of progression of sarcosine detection reaction. The degree of progression of sarcosine detection reaction 7.5 and 10 minutes after the mixing of the sample with the first reagent-D (in other words, 2.5 and 5 minutes after the addition of the second reagent-H) is shown in Table 8.

TABLE 8

|  | Degree of progression of reaction (%) after 7.5 minutes | Degree of progression of reaction (%) after 10 minutes |
|---|---|---|
| Not added (Comparative Example 1) | 60 | 82 |
| Mordant Orange 1 (Present invention 1) | 67 | 88 |
| Alizarin Yellow GG (Present invention 2) | 64 | 86 |
| Chrome Yellow (Present invention 3) | 65 | 87 |
| Direct Yellow 44 (Present invention 4) | 68 | 89 |
| Acid Red 151 (Present invention 5) | 68 | 89 |
| Xylene Fast Yellow 2G (Present invention 7) | 64 | 86 |
| Disperse Diazo Black 3BF (Present invention 9) | 63 | 84 |

As shown in Table 8, Mordant Orange 1, Alizarin Yellow GG, Chrome Yellow, Direct Yellow 44, Acid Red 151, Xylene Fast Yellow 2G, and Disperse Diazo Black 3BF were found to have the effect of accelerating sarcosine detection reaction.

[Example 12] Measurement of Absorbance when Cholesterol Detection Reaction Mediated by Cholesterol Oxidase was Completed In this Example the amount of change in absorbance is determined when the detection reaction for the substrate cholesterol was completed using an excess amount of cholesterol oxidase (CHO-CE), which is an oxidase.

A reagent for cholesterol measurement having the following composition was prepared, and the measurement of cholesterol using cholesterol oxidase was carried out using Bio Majesty JCA-BM 1650 (manufactured by JEOL Ltd.).
(Sample)
32 μM cholesterol (manufactured by Wako Pure Chemical Industries, Ltd.)
5.0% (v/v) Triton X-100 (manufactured by Wako Pure Chemical Industries, Ltd.)
4.0% (w/v) sodium cholate (manufactured by Wako Pure Chemical Industries, Ltd.)
(First Reagent-E)
30 mM MOPS-NaOH buffer solution, pH 7.0
10 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
0.04% (w/v) of the compound of Comparative Example 2, any one compound of the present invention, or compound-free (Comparative Example 1) ion-exchange water as shown in Table 1
(Second Reagent-I)
10 mM MOPS-NaOH buffer solution, pH 7.0
11.6 U/ml CHO-CE (manufactured by Kikkoman Biochemifa Company)

8 μl of the sample was added to 96 μl of the first reagent-E, and the mixture was incubated at 37° C. for 5 minutes. Then, 24 μl of the second reagent-I was added thereto, and the quantitative reaction of hydrogen peroxide resulting from the oxidation of cholesterol was allowed to progress at 37° C. for 5 minutes. The absorbance ($A_{694}$ and $A_{751}$) of the reaction solution for light at wavelengths of 694 nm and 751 nm was measured over time for 10 minutes after the mixing of the sample with the first reagent-E to determine the value of subtraction of $A_{751}$ from $A_{694}$, i.e., the value $A_{694/751}$. Subsequently, ΔA was calculated by subtracting, from $A_{694/751}$, the value of (104/128) times $A_{694/751}$ 4.8 minutes after the mixing of the sample with the first reagent-E. Incidentally, 4.8 minutes after the mixing of the sample with the first reagent-E represents the time immediately before the addition of the second reagent-I. ΔA 9 minutes and 10 minutes after the mixing of the diluted sample with the first reagent-E ($ΔA_{9min}$ and $ΔA_{10min}$) are shown in Table 9.

TABLE 9

|  | $ΔA_{9\,min}$ | $ΔA_{10\,min}$ |
| --- | --- | --- |
| Not added (Comparative Example 1) | 0.022 | 0.022 |
| Mordant Orange 1 (Present invention 1) | 0.041 | 0.041 |
| Alizarin Yellow GG (Present invention 2) | 0.039 | 0.039 |

TABLE 9-continued

|  | $ΔA_{9\,min}$ | $ΔA_{10\,min}$ |
| --- | --- | --- |
| Chrome Yellow (Present invention 3) | 0.071 | 0.072 |
| Acid Red 151 (Present invention 5) | 0.036 | 0.036 |
| Acid Yellow 36 (Present invention 6) | 0.033 | 0.033 |
| Acid Yellow 34 (Present invention 8) | 0.033 | 0.033 |
| Disperse Diazo Black 3BF (Present invention 9) | 0.028 | 0.032 |

As shown in Table 9, no difference between $ΔA_{9min}$ and $ΔA_{10min}$ was observed for the compounds of the present invention and Comparative Examples. In other words, it can be recognized that the quantitative reaction of cholesterol, i.e., the quantitative reaction of hydrogen peroxide resulting from the oxidation of cholesterol, was completed in 10 minutes after the mixing of the diluted sample with the first reagent-E. Accordingly, in Examples 12 and 13, $ΔA_{10min}$ in each Comparative Example or the present invention was defined as ΔA when 100% of the quantitative reaction of cholesterol progressed under each condition ($ΔA_{100\%}$).

[Example 13] Calculation of Effect of Accelerating Cholesterol Detection Reaction Mediated by Cholesterol Oxidase by the Compound of Present Invention Next, in this Example, the degree of acceleration of cholesterol detection reaction by the compound of the present invention was determined using a small amount of cholesterol oxidase.

A reagent for cholesterol measurement having the following composition was prepared, and the measurement of cholesterol was carried out using Bio Majesty JCA-BM 650 (manufactured by JEOL Ltd.).
(Sample)
32 μM cholesterol (manufactured by Wako Pure Chemical Industries, Ltd.)
5.0% (v/v) Triton X-100 (manufactured by Wako Pure Chemical Industries, Ltd.)
4.0% (w/v) sodium cholate (manufactured by Wako Pure Chemical Industries, Ltd.)
(First reagent-E)
30 mM MOPS-NaOH buffer solution, pH 7.0
10 U/ml peroxidase PEO-301 (Toyobo Co., Ltd.)
0.023 mM 10-(carboxymethylaminocarbonyl)-3,7-bis(dimethylamino)phenothiazine sodium (DA-67, manufactured by Wako Pure Chemical Industries, Ltd.)
0.04% (w/v) of the compound of Comparative Example 2, any one compound of the present invention, or compound-free (Comparative Example 1) ion-exchange water as shown in Table 1
(Second Reagent-J)
10 mM MOPS-NaOH buffer solution, pH 7.0
2.31 U/ml CHO-CE (manufactured by Kikkoman Biochemifa Company)

8 μl of the sample was added to 96 μl of the first reagent-E, and the mixture was incubated at 37° C. for 5 minutes. Then, 24 μl of the second reagent-J was added thereto, and the quantitative reaction of hydrogen peroxide resulting from the oxidation of cholesterol was allowed to progress at 37° C. for 5 minutes. The absorbance ($A_{694}$ and $A_{751}$) of the reaction solution for light at wavelengths of 694 nm and 751 nm was measured over time for 10 minutes after the mixing of the sample with the first reagent-E to determine the value of subtraction of $A_{751}$ from $A_{694}$, i.e., the value $A_{694/751}$. Subsequently, ΔA was calculated by subtracting, from $A_{694/751}$, the value of (104/128) times $A_{694/751}$ 4.8 minutes after the mixing of the sample with the first reagent-E. Incidentally, 5 minutes after the mixing of the sample with the first reagent-E represents the time immediately before the addition of the second reagent-J.

Next, ΔA calculated in this Example was divided by $ΔA_{100\%}$ defined in Example 12 to calculate the degree of progression of cholesterol detection reaction. The degree of progression of cholesterol detection reaction 7.5 and 10 minutes after the mixing of the sample with the first reagent-E (in other words, 2.5 and 5 minutes after the addition of the second reagent-J) is shown in Table 10.

TABLE 10

|  | Degree of progression of reaction (%) after 7.5 minutes | Degree of progression of reaction (%) after 10 minutes |
|---|---|---|
| Not added (Comparative Example 1) | 65 | 88 |
| Mordant Orange 1 (Present invention 1) | 74 | 94 |
| Alizarin Yellow GG (Present invention 2) | 73 | 93 |
| Chrome Yellow (Present invention 3) | 67 | 91 |
| Acid Red 151 (Present invention 5) | 74 | 94 |
| Acid Yellow 36 (Present invention 6) | 73 | 92 |
| Acid Yellow 34 (Present invention 8) | 72 | 92 |
| Disperse Diazo Black 3BF (Present invention 9) | 66 | 97 |

As shown in Table 10, Mordant Orange 1, Alizarin Yellow GG, Chrome Yellow, Acid Red 151, Acid Yellow 36, Acid Yellow 34, and Disperse Diazo Black 3BF were found to have the effect of accelerating cholesterol detection reaction.

Incidentally, the reaction accelerating agent of the present invention may also accelerate enzymatic reaction catalyzed by peroxidase. However, under the conditions of the present Examples, an excess amount of peroxidase is added to the system and it is believed that hydrogen peroxide resulting from the enzymatic reaction of the various types of oxidases is immediately degraded by the peroxidase. Therefore, it is believed that the above results of reaction acceleration are mainly due to acceleration of the enzymatic reaction of the various types of oxidases by the reaction accelerating agent of the present invention.

INDUSTRIAL APPLICABILITY

By using the oxidase reaction accelerating agent of the present invention it is possible to decrease the amount of an oxidase formulated into a reagent for clinical diagnosis such as a HbA1c measurement reagent, a GA measurement reagent, a sarcosine measurement reagent, or a cholesterol measurement reagent. Furthermore, use of the oxidase reaction accelerating agent of the present invention enables shortening the reaction time and enhancing detection sensitivity.

BRIEF DESCRIPTION OF SEQUENCE LISTING

SEQ ID NO: 1—Amino acid sequence of CFP-DH2
SEQ ID NO: 2—Nucleotide sequence of CFP-DH2 gene
SEQ ID NO: 3—Primer for R64G introduction
SEQ ID NO: 4—Primer for R64G introduction
SEQ ID NO: 5—Amino acid sequence of CFP-DH3
SEQ ID NO: 6—Primer for L110Y introduction
SEQ ID NO: 7—Primer for L110Y introduction
SEQ ID NO: 8—Amino acid sequence of CFP-DH4

All publications, patents and patent applications cited herein are incorporated herein by reference in their entirety.

The invention claimed is:

1. A method comprising contacting an oxidase and a substrate for the oxidase with an oxidase reaction accelerating agent represented by the following formula (I):

[Formula 1]

$R^1$—N=N—$R^2$ (I)

wherein $R^1$ and $R^2$ are each independently an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents, wherein said substituent(s) is selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —CONH$_2$, —NO$_2$, —NH$_2$, —CO—NH$_2$, —$R^3$, —NH—$R^4$, —NHCO—NH—$R^5$—N=N—$R^6$, —SO$_3$X, —COOX, Y, and Z;

X is selected from the group consisting of —H, —Na, —K, and —Li;

Y is selected from the group consisting of —H, —SO$_3$X, and —COOX;

Z is selected from the group consisting of —H, —$C_{1-6}$ alkyl, —O—$C_{1-6}$ alkyl, and —SO$_3$X;

each X, Y, and Z may be the same or different;

—$R^3$ is —H, or is an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —CONH$_2$, —NO$_2$, —NH$_2$, and —SO$_3$X;

—$R^4$ is an aromatic 5- or 6-membered monocyclic carbocyclic ring or heterocyclic ring containing at least one nitrogen atom, sulfur atom or oxygen atom, or a 9- or 10-membered fused ring containing the aromatic 5- or 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —CONH$_2$, —NO$_2$, —NH$_2$, —SO$_3$X, —COOX, Y, and Z; and —$R^5$ and —$R^6$ are each independently an aromatic 5- or 6-membered monocyclic carbocyclic ring or heterocyclic ring containing at least one nitrogen atom, sulfur atom or oxygen atom, or a 9- or 10-membered fused ring containing the aromatic 5- to 6-membered monocyclic carbocyclic ring or heterocyclic ring, wherein the ring may optionally be substituted with one or more substituents selected from the group consisting of —F, —Cl, —Br, —I, —At, —$C_{1-6}$ alkyl, —$C_{2-6}$ alkenyl, —$C_{2-6}$ alkynyl, =O, —OH, —O—$C_{1-6}$ alkyl, —O—CH$_3$, —CONH$_2$, —NO$_2$, —NH$_2$, —SO$_3$X, —COOX, Y, and Z, provided that when $R^1$ or $R^2$ is an aromatic 5-membered monocyclic carbocyclic ring or heterocyclic ring containing at least one nitrogen atom, sulfur atom or oxygen atom, the heterocyclic ring is not substituted with —COOX, wherein when $R^1$ or $R^2$ is

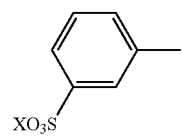

then $R^2$ or $R^1$, respectively, is not

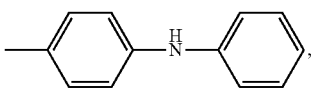

wherein the compound represented by the following formula is excluded from the oxidase reaction accelerating agent of formula (I):

[Formula 66]

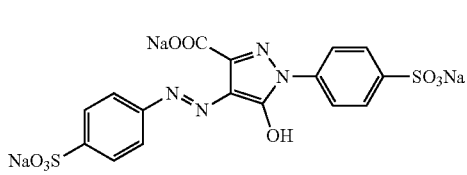

Tartrazine, wherein, when $R^1$ or $R^2$ is

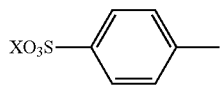

and $R^2$ or $R'$, respectively, is,

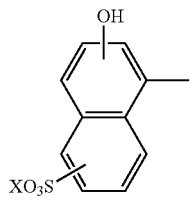

then the oxidase is an oxidase selected from the group consisting of sarcosine oxidase, and cholesterol oxidase;
wherein, when $R^1$ or $R^2$ is

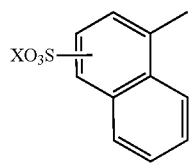

and $R^2$ or $R'$, respectively, is

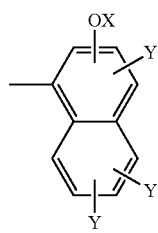

and wherein the Y which may be at positions 2, 3 or 4 of the 1-naphthyl group is H and the two Y groups which may be at positions 5, 6, 7 or 8 of the 1-naphthyl group are both —SO$_3$X, then the oxidase is an oxidase selected from the group consisting of sarcosine oxidase, and cholesterol oxidase;

wherein, when $R^1$ or $R^2$ is

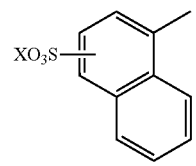

and $R^2$ or $R'$, respectively, is

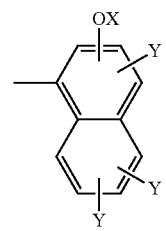

and wherein the Y which may be at positions 2, 3 or 4 of the 1-naphthyl group is —SO$_3$X and one of the Y groups which may be at positions 5, 6, 7 or 8 of the 1-naphthyl group is H and the other Y group which may be at positions 5, 6, 7 or 8 of the 1-naphthyl group is —SO$_3$X, then the oxidase is an oxidase selected from the group consisting of sarcosine oxidase, and cholesterol oxidase;

wherein, when the oxidase reaction accelerating agent is represented by the following formula:

[Formula 11]

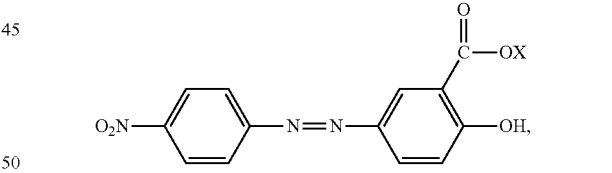

IV then the oxidase is an oxidase selected from the group consisting of amadoriase, sarcosine oxidase, and cholesterol oxidase,
wherein, when $R^1$ or $R^2$ is

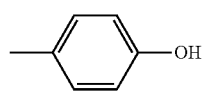

and $R^2$ or $R'$, respectively is an aromatic 6-membered monocyclic carbocyclic ring substituted with —COOX, then the oxidase is an oxidase selected from the group consisting of amadoriase and sarcosine oxidase; and wherein when the compound represented by Formula (I) is

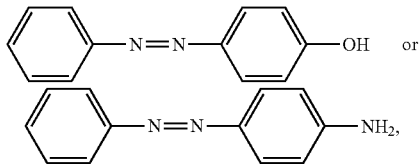

then the oxidase is selected from the group consisting of amadoriase, sarcosine oxidase, and cholesterol oxidase.

2. The method according to claim 1, wherein regarding the reaction accelerating agent represented by formula (I), $R^1$ and $R^2$ are each independently an aromatic 6-membered monocyclic carbocyclic ring, or a 10-membered fused ring containing the aromatic 6-membered monocyclic carbocyclic ring, wherein the ring may optionally be substituted with one or more substituents or wherein regarding the reaction accelerating agent represented by formula (I), $R^1$ and $R^2$ are each independently selected from the group consisting of

[Formula 2]

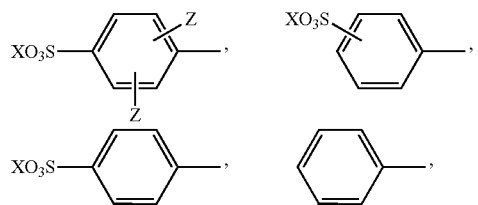

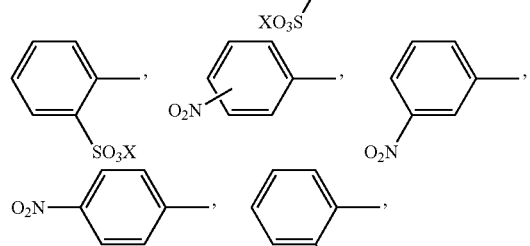

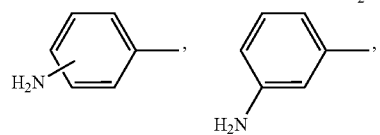

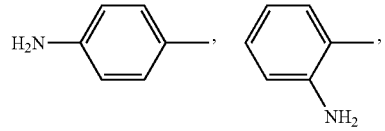

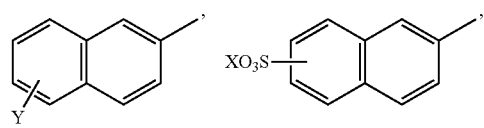

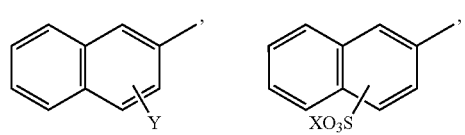

-continued

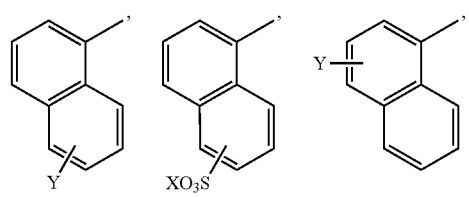

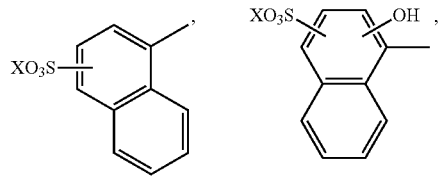

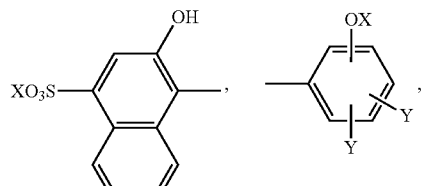

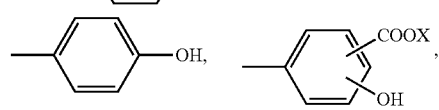

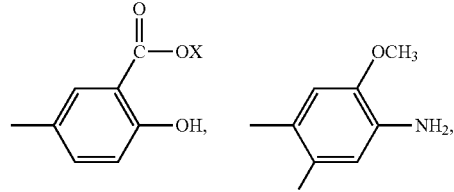

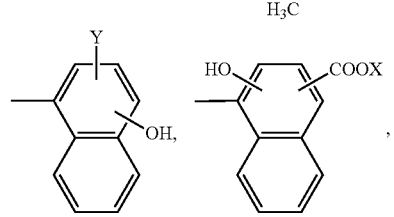

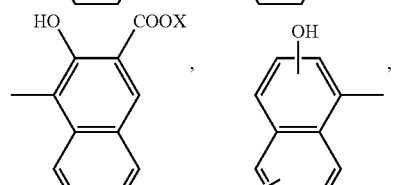

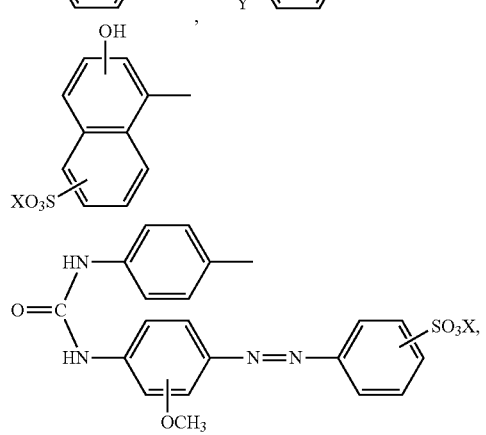

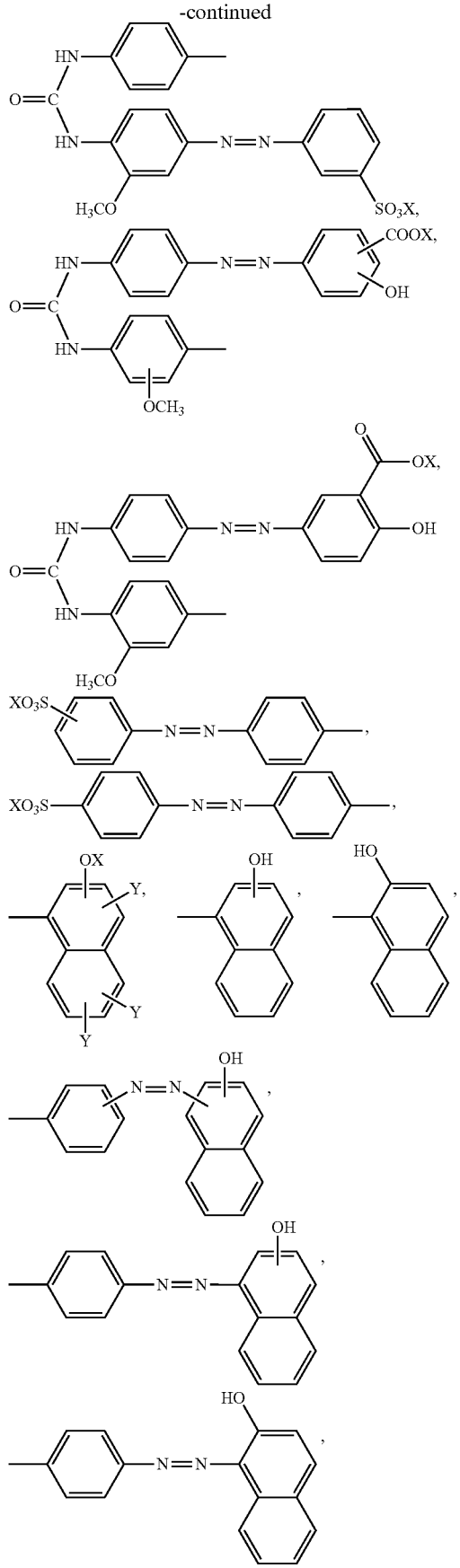
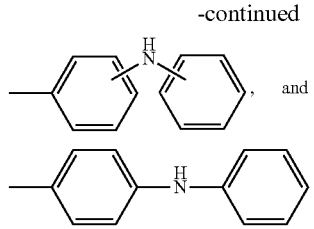
wherein X, Y, and Z are as defined in claim 1.
3. The method according to claim 1, wherein regarding the reaction accelerating agent represented by formula (I), $R^1$ is selected from the group consisting of
[Formula 3]
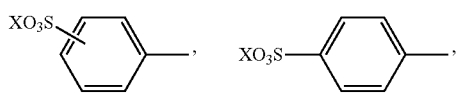
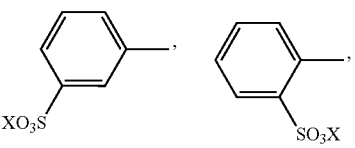
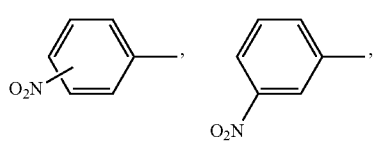
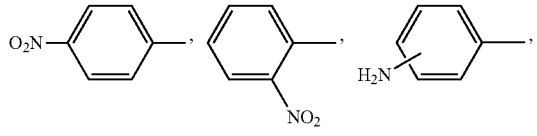
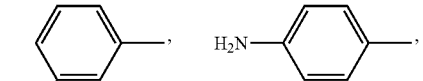
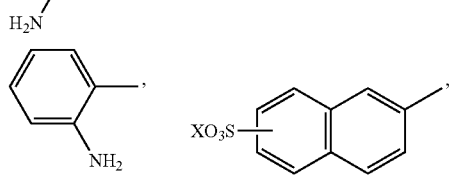
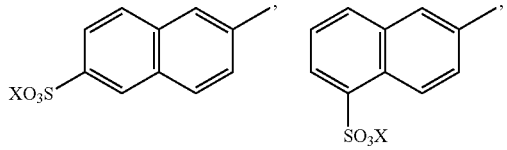
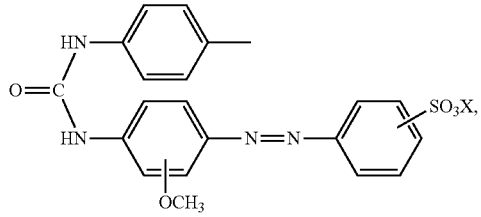

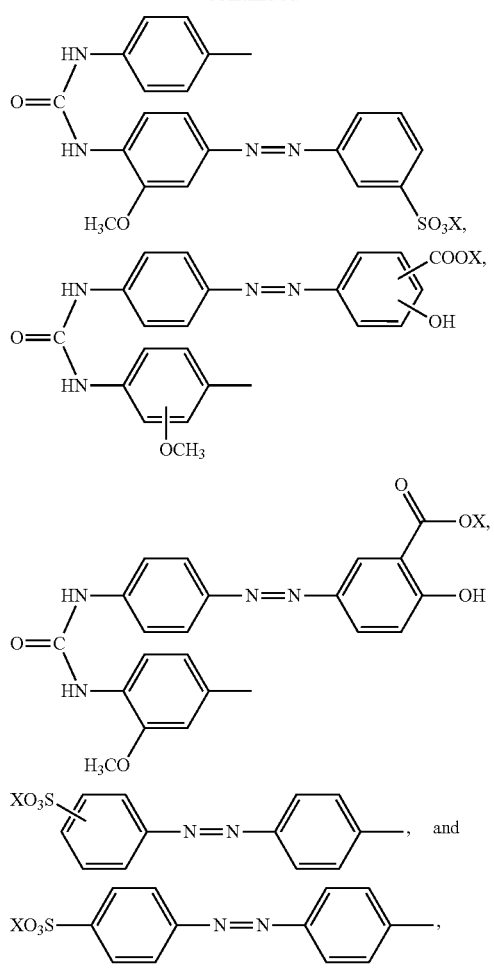

and R¹ is selected from the group consisting of

[Formula 4]

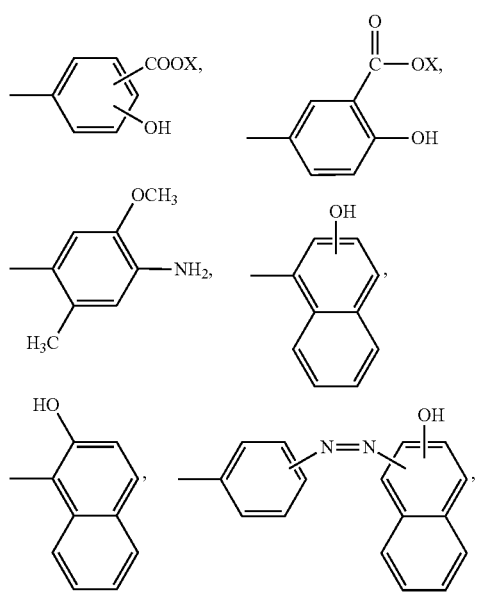

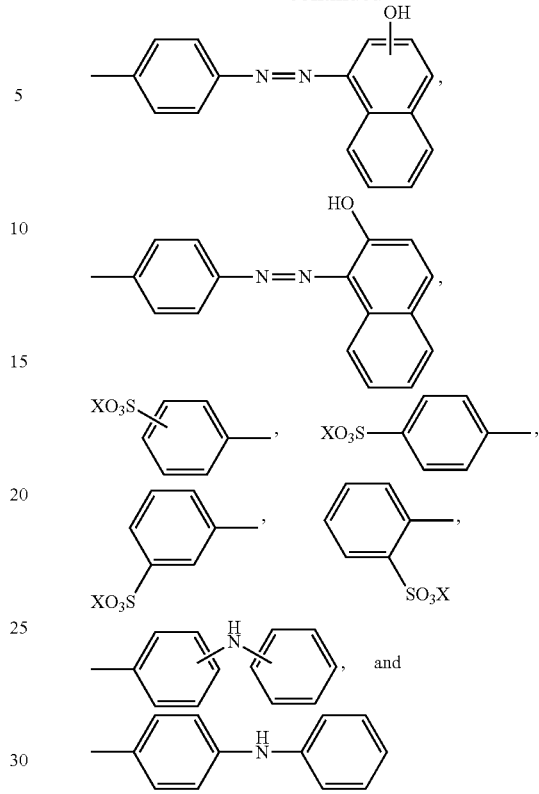

wherein X is as defined in claim 1.

4. The method according to claim 1, wherein the reaction accelerating agent represented by formula (I) is a reaction accelerating agent represented by the following formula:

[Formula 5]

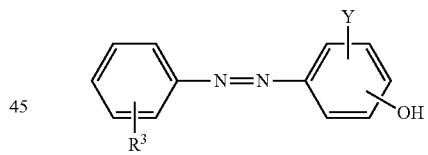

(II)

wherein
Y is selected from the group consisting of —H, —SO₃X, and —COOX;
X is selected from the group consisting of —H, —Na, —K, and —Li;
each X and Y may be the same or different;
R³ is —H or —NHCO—NH—R⁵—N═N—R⁶, or is an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C₁₋₆ alkyl, —C₂₋₆ alkenyl, —C₂₋₆ alkynyl, ═O, —OH, —O—C₁₋₆ alkyl, —CONH₂, —NO₂, —NH₂, and —SO₃X; and
—R⁵ and —R⁶ are each independently an aromatic 6-membered monocyclic carbocyclic ring, or a 10-membered fused ring containing the carbocyclic ring, wherein the ring may optionally be substituted with one or more substituents selected from the group consisting of —F, —Cl, —Br, —I, —At, —C$_{1-6}$ alkyl, —C$_{2-6}$ alkenyl, —C$_{2-6}$ alkynyl, =O, —OH, —O—C$_{1-6}$ alkyl, —O—CH$_3$, —CONH$_2$, —NO$_2$, —NH$_2$, and —SO$_3$X.

5. The method according to claim 1, wherein the reaction accelerating agent represented by formula (I) is a reaction accelerating agent represented by any of the following formulae:

[Formula 6]

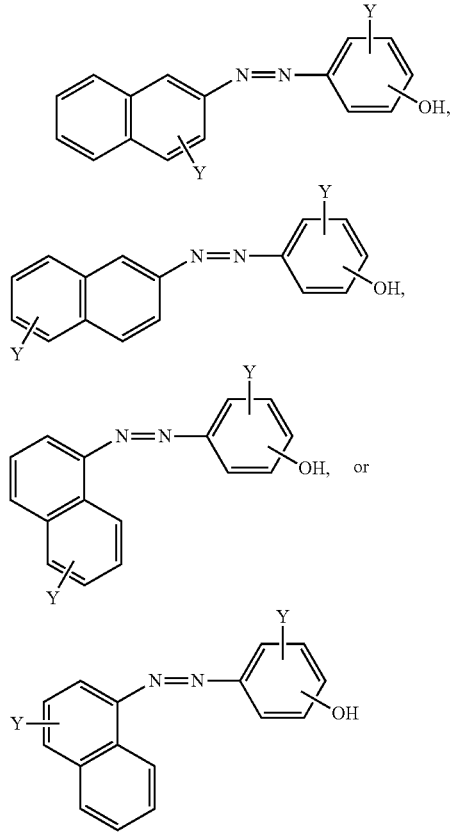

wherein
X is selected from the group consisting of —H, —Na, —K, and —Li;
Y is selected from the group consisting of —H, —SO$_3$X, and —COOX; and
each X and Y may be the same or different.

6. The method according to claim 1, wherein the reaction accelerating agent represented by formula (I) is a reaction accelerating agent represented by the following formula:

[Formula 7]

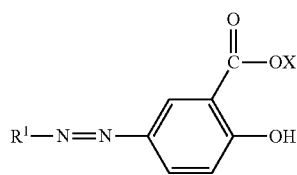

(III)

wherein
R$^1$ is a benzene ring or a naphthalene ring which may optionally be substituted with one or more substituents, wherein
said substituent(s) is selected from the group consisting of —NO$_2$, —SO$_3$X, and

[Formula 8]

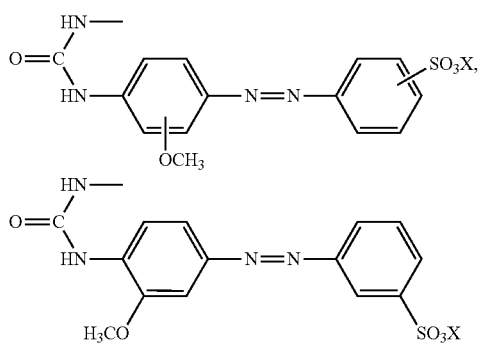

and
X is selected from the group consisting of —H, —Na, —K, and —Li.

7. The method according to claim 1, wherein R$^2$ is an aromatic 5-membered monocyclic heterocyclic ring containing two nitrogen atoms wherein said ring may optionally be substituted with one or more substituents, and the heterocyclic ring is substituted with

[Formula 9]

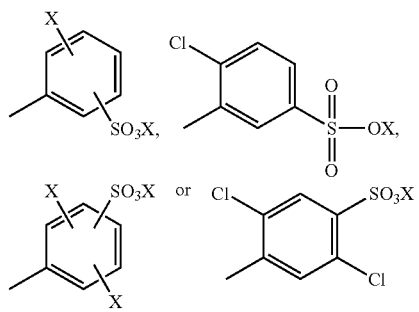

wherein X is as defined in claim 1, and each X may be the same or different or
wherein R$^1$ is

[Formula 10]

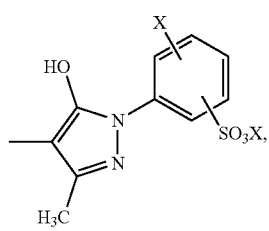

-continued

[Chemical structures shown]

wherein X is as defined in claim 1, and each X may the same or different.

8. The method according to claim 1, wherein the compound represented by formula (I) is selected from the group consisting of a compound represented by the following formula:

[Formula 11]

IV

[Chemical structure shown]

wherein X is selected from the group consisting of —H, —Na, —K, and —Li, a compound represented by the following formula:

[Formula 12]

V

[Chemical structure shown]

wherein X is selected from the group consisting of —H, —Na, —K, and —Li, a compound represented by the following formula:

[Formula 13]

VI

[Chemical structure shown]

wherein X is selected from the group consisting of —H, —Na, —K, and —Li, and each X may be the same or different, a compound represented by the following formula:

[Formula 14]

VII

[Chemical structure shown]

wherein X is selected from the group consisting of —H, —Na, —K, and —Li, and each X may be the same or different, a compound represented by the following formula:

[Formula 15]

VIII

[Chemical structure shown]

wherein X is selected from the group consisting of —H, —Na, —K, and —Li, a compound represented by the following formula:

[Formula 17]

X

[Chemical structure shown]

wherein X is selected from the group consisting of —H, —Na, —K, and —Li, and each X may be the same or different, a compound represented by the following formula:

[Formula 18]

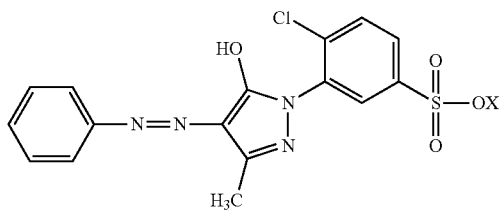

wherein X is selected from the group consisting of —H, —Na, —K, and —Li, and a compound represented by the following formula:

[Formula 19]

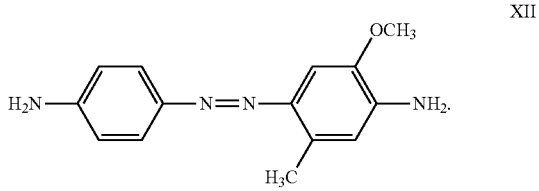

9. The method according to claim 1, wherein the oxidase is an oxidase selected from the group consisting of amadoriase, sarcosine oxidase, and cholesterol oxidase.

* * * * *